(12) United States Patent
Wu et al.

(10) Patent No.: US 11,795,488 B2
(45) Date of Patent: Oct. 24, 2023

(54) METHODS FOR ENZYMATIC PEPTIDE LIGATION

(71) Applicant: NANYANG TECHNOLOGICAL UNIVERSITY, Singapore (SG)

(72) Inventors: Bin Wu, Singapore (SG); Renliang Yang, Singapore (SG); Yee Hwa Wong, Singapore (SG); Julien Lescar, Singapore (SG); Chuan Fa Liu, Singapore (SG); James P Tam, Singapore (SG); Kien Truc Giang Nguyen, Singapore (SG); Ziqi Long, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 478 days.

(21) Appl. No.: 16/336,023

(22) PCT Filed: Sep. 12, 2017

(86) PCT No.: PCT/SG2017/050458
§ 371 (c)(1),
(2) Date: Mar. 22, 2019

(87) PCT Pub. No.: WO2018/056899
PCT Pub. Date: Mar. 29, 2018

(65) Prior Publication Data
US 2019/0218586 A1  Jul. 18, 2019

(30) Foreign Application Priority Data

Sep. 23, 2016 (SG) .......................... 10201607951V

(51) Int. Cl.
C12P 21/02 (2006.01)
C12N 9/00 (2006.01)
C07K 14/415 (2006.01)

(52) U.S. Cl.
CPC ............ *C12P 21/02* (2013.01); *C07K 14/415* (2013.01); *C12N 9/93* (2013.01)

(58) Field of Classification Search
None
See application file for complete search history.

(56) References Cited

FOREIGN PATENT DOCUMENTS

| WO | 2015/163818 | 10/2015 |
| WO | 2017/049362 | 3/2017 |
| WO | 2017/054044 | 4/2017 |

OTHER PUBLICATIONS

Ivana Saska et al (An Asparaginyl Endopeptidase Mediates in Vivo Protein Backbone Cyclization) The Journal of Biological Chemistry vol. 282, No. 40, pp. 29721-29728, Oct. 5, 2007. (Year: 2007).*

Supplementary European Search Report corresponding to European Application No. EP 17853546.4, 7 pages, dated Mar. 23, 2020.
Altschul et al., "Basic Local Alignment Search Tool," *Journal of Molecular Biology*, 215:403-410, 1990.
Altschul et al., "Gapped BLAST and PSI-BLAST: a new generation of protein database search programs," *Nucleic Acids Research*, 25(17):3389-3402, 1997.
Bernath-Levin et al., "Peptide Macrocyclization by a Bifunctional Endoprotease," *Chemistry & Biology*, 22:571-582, 2015, (13 pages).
Chen et al., "Cloning, Isolation, and Characterization of Mammalian Legumain, an Asparaginyl Endopeptidase," *The Journal of Biological Chemistry*, 272(12):8090-8098, 1997. (10 pages).
Chen et al., "A general strategy for the evolution of bond-forming enzymes using yeast display," *PNAS*, 108(28):11399-11404, 2011.
Dall et al., "Mechanistic and structural studies on legumain explain its zymogenicity, distinct activation pathways, and regulation," *PNAS*, 110(27):10940-10945, 2013.
Dall et al., "Structure and function of legumain in health and disease," *Biochimie*, 122:126-150, 2016.
Dall et al., "Structure and Mechanism of an Aspartimide-Dependent Peptide Ligase in Human Legumain," *Angewandte Chemie International Edition*, 54:2917-2921, 2015.
Guimaraes et al., "Site-specific C-terminal and internal loop labeling of proteins using sortase-mediated reactions," *Nature Protocols*, 8(9):1787-1799, 2013.
Harris et al., "Efficient backbone cyclization of linear peptides by a recombinant asparaginyl endopeptidase," *Nature Communications*, 6(10199):1-10, 2015.
Ishii, "Legumain: Asparaginyl Endopeptidase," *Methods in Enzymology*, 244:604-615, 1994.
Nguyen et al., "Butelase I: A Versatile Ligase for Peptide and Protein Macrocyclization," *Journal of the American Chemical Society*, 137:15398-15401, 2015.
Nguyen et al., "Butelase I is an Asx-specific ligase enabling peptide macrocyclization and synthesis," *Nature Chemical Biology*, 10(9):732-738, 2014, (42 pages).
Nguyen et al., "Site-Specific N-Terminal Labeling of Peptides and Proteins using Butelase I and Thiodepsipeptide," *Angewandte Chemie International Edition*, 54:15694-15698, 2015.
Saska et al., "An Asparaginyl Endopeptidase Mediates in Vivo Protein Backbone Cyclization," *The Journal of Biological Chemistry*, 282(40):29721-29728, 2007, (9 pages).

(Continued)

*Primary Examiner* — Kagnew H Gebreyesus
(74) *Attorney, Agent, or Firm* — Seed IP Law Group LLP

(57) ABSTRACT

The present invention relates to a method of ligating a first peptide via its C-terminus to the N-terminus of a second peptide, wherein the reaction is catalyzed by an asparagine/aspartate (Asx) peptide ligase OaAEPI Cys247Ala having the amino acid sequence of SEQ ID NO: 1. Further encompassed are a method of preparing a dimer, oligomer, or multimer of one or more peptides of interest and a method of modifying or tagging the surface of a target cell by one or more peptides of interest. Also encompassed in the invention are the ligated peptides and/or tagged target cells obtainable according to any of the methods, the peptide ligase OaAEPI Cys247Ala having the amino acid sequence of SEQ ID NO: 1, as well as kits comprising said peptide ligase.

12 Claims, 52 Drawing Sheets

Specification includes a Sequence Listing.

(56) References Cited

OTHER PUBLICATIONS

Swee et al., "Sortase-mediated modification of αDEC205 affords optimization of antigen presentation and immunization against a set of viral epitopes," *PNAS*, 110(4):1428-1433, 2013.

Theile et al., "Site-specific N-terminal labeling of proteins using sortase-mediated reactions," *Nature Protocols*, 8(9):1800-1807, 2013, (9 pages).

Wagner et al., "Bispecific antibody generated with sortase and click chemistry has broad antiinfluenza virus activity," *PNAS*, 111(47):16820-16825, 2014.

Witte et al., "Production of unnaturally linked chimeric proteins using a combination of sortase-catalyzed transpeptidation and click chemistry," *Nature Protocols*, 8(9):1808-1819, 2013.

Yang et al., "Engineering a Catalytically Efficient Recombinant Protein Ligase," *Journal of the American Chemical Society*, 139:5351-5358, 2017.

Zhao et al., "Structural analysis of asparaginyl endopeptidase reveals the activation mechanism and a reversible intermediate maturation stage," *Cell Research*, 24(3):344-358, 2014.

\* cited by examiner a b f

WT, 10MIN

AEP WT, 1H

Gly, 10 min

Gly, 1 h

Ser, 10 min

Ser, 1 h

Thr, 10 min

Thr, 1 h

Met, 10 min

Met, 1 h

Val, 10 min

Val, 1 h

Leu, 10 min

Leu, 1 h

Ile, 10 min

Ile, 1 h a b c d

GLYRRGRLYRRNXL (J1-J20: NGL, NAL, NTL, NSL, NYL, NCL, NEL, NPL, NLL, NIL, NNL, NWL, NRL, NHL, NDL, NVL, NML, NKL, NQL, NFL, total 20 peptides)

GLYRRGRLYRRNGX (J21-L16: NGG, NGA, NGT, NGS, NGY, NGC, NGE, NGP, NGI, NGN, NGW, NGR, NGH, NGD, NGV, NGM, NGK, NGQ, NGF total 19 peptides, NGL is the same peptide as the first plot-J1)

GL PVSTKPVATRDAL cyclization for 5 min, when replacing the Asn in NAL sequence with Asp in DAL sequence. The ligation is less efficient but still robust enough.

XLYRRGRLYRRNAL (L1-L20: VL, ML, GL, RL, QL, WL, EL, PL, DL, TL, SL, AL, IL, NL, KL, CL, YL, HL, FL, LL)

a

One Step Homodimerization
Scaffold based dimerization strategy

Ub-AA-NGL+2-mer linker   Ub (50 uM), AEP 0.5 uM, 1 h b

Two-step, heterodimerization strategy

'Ub-linker' intermediate as an example

| | | | |
|---|---|---|---|
| Ub-linker (uM) | 50 | 50 | 50 |
| Ub-AA-NGL (uM) | 0 | 100 | 200 |
| AEP (uM) | 0 | 0.5 | 0.5 |

— ub2
— Ub-Linker
— Ub-AA-NGL d

Schematic Illustration of protein ultra-oligomer strategy e f g h i a b

M = Molecular weight
1 = SNAP-NGL protein control
2 = SNAP-NGL added to RAW cells, no ligase, cells after wash    5 = same as 2, using HEK cells
3 = SNAP-NGL added to RAW cells, with ligase, wash solution    6 = same as 3, using HEK cells
4 = SNAP-NGL added to RAW cells, with ligase, cells after wash    7 = same as 4, using HEK cells c

SEQUENCE LISTING

<160> NUMBER OF SEQ ID NOS: 19

<210> SEQ ID NO 1
<211> LENGTH: 474
<212> TYPE: PRT
<213> ORGANISM: Ovaloparmena affinis

<400> SEQUENCE: 1

```
Met Val Arg Tyr Leu Ala Gly Ala Val Leu Leu Val Val Leu Ser
1               5                   10                  15

Val Ala Ala Val Ser Gly Ala Arg Asp Gly Asp Tyr Leu His Leu
            20                  25                  30

Pro Ser Glu Val Ser Arg Phe Phe Arg Pro Gln Glu Thr Asn Asp Asp
            35                  40                  45

His Gly Glu Asp Ser Val Gly Thr Arg Trp Ala Val Leu Ile Ala Gly
        50                  55                  60

Ser Lys Gly Tyr Ala Asn Tyr Arg His Gln Ala Gly Val Cys His Ala
65                  70                  75                  80

Tyr Gln Ile Leu Lys Arg Gly Gly Leu Lys Asp Glu Asn Ile Val Val
                85                  90                  95

Phe Met Tyr Asp Asp Ile Ala Tyr Asn Glu Ser Asn Pro Arg Pro Gly
            100                 105                 110

Val Ile Ile Asn Ser Pro His Gly Ser Asp Val Tyr Ala Gly Val Pro
            115                 120                 125

Lys Asp Tyr Thr Gly Glu Glu Val Asn Ala Lys Asn Phe Leu Ala Ala
            130                 135                 140

Ile Leu Gly Asn Lys Ser Ala Ile Thr Gly Gly Ser Gly Lys Val Val
145                 150                 155                 160

Asp Ser Gly Pro Asn Asp His Ile Phe Ile Tyr Tyr Thr Asp His Gly
                165                 170                 175

Ala Ala Gly Val Ile Gly Met Pro Ser Lys Pro Tyr Leu Tyr Ala Asp
            180                 185                 190

Glu Leu Asn Asp Ala Leu Lys Lys Lys His Ala Ser Gly Thr Tyr Lys
            195                 200                 205

Ser Leu Val Phe Tyr Leu Glu Ala Cys Glu Ser Gly Ser Met Phe Glu
    210                 215                 220

Gly Ile Leu Pro Glu Asp Leu Asn Ile Tyr Ala Leu Thr Ser Thr Asn
225                 230                 235                 240

Thr Thr Glu Ser Ser Trp Ala Tyr Tyr Cys Pro Ala Gln Glu Asn Pro
                245                 250                 255

Pro Pro Pro Glu Tyr Asn Val Cys Leu Gly Asp Leu Phe Ser Val Ala
            260                 265                 270

Trp Leu Glu Asp Ser Asp Val Gln Asn Ser Trp Tyr Glu Thr Leu Asn
        275                 280                 285

Gln Gln Tyr His His Val Asp Lys Arg Ile Ser His Ala Ser His Ala
    290                 295                 300

Thr Gln Tyr Gly Asn Leu Lys Leu Gly Glu Glu Gly Leu Phe Val Tyr
305                 310                 315                 320

Met Gly Ser Asn Pro Ala Asn Asp Asn Tyr Thr Ser Leu Asp Gly Asn
                325                 330                 335

Ala Leu Thr Pro Ser Ser Ile Val Val Asn Gln Arg Asp Ala Asp Leu
            340                 345                 350

Leu His Leu Trp Glu Lys Phe Arg Lys Ala Pro Glu Gly Ser Ala Arg
            355                 360                 365
```

```
Lys Glu Glu Ala Gln Thr Gln Ile Phe Lys Ala Met Ser His Arg Val
    370                 375                 380

His Ile Asp Ser Ser Ile Lys Leu Ile Gly Lys Leu Leu Phe Gly Ile
385                 390                 395                 400

Glu Lys Cys Thr Glu Ile Leu Asn Ala Val Arg Pro Ala Gly Gln Pro
                405                 410                 415

Leu Val Asp Asp Trp Ala Cys Leu Arg Ser Leu Val Gly Thr Phe Glu
            420                 425                 430

Thr His Cys Gly Ser Leu Ser Glu Tyr Gly Met Arg His Thr Arg Thr
        435                 440                 445

Ile Ala Asn Ile Cys Asn Ala Gly Ile Ser Glu Glu Gln Met Ala Glu
    450                 455                 460

Ala Ala Ser Gln Ala Cys Ala Ser Ile Pro
465                 470
```

```
<210> SEQ ID NO 2
<211> LENGTH: 18
<212> TYPE: PRT
<213> ORGANISM: Ovaloparmena affinis
<220> FEATURE:
<221> NAME/KEY: MISC_FEATURE
<222> LOCATION: (1)..(1)
<223> OTHER INFORMATION: Xaa corresponds to position 247 of SEQ ID NO:1
      and is Gly, Ala, Ser, or Cys.
<220> FEATURE:
<221> NAME/KEY: MISC_FEATURE
<222> LOCATION: (2)..(2)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (6)..(6)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (7)..(7)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (8)..(8)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (9)..(9)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (10)..(10)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (16)..(16)
<223> OTHER INFORMATION: Xaa is any amino acid, preferably any amino
      acid that does not disrupt the structural fold of the remaining
      conserved amino acids
<220> FEATURE:
<221> NAME/KEY: MISC_FEATURE
<222> LOCATION: (17)..(17)
<223> OTHER INFORMATION: Xaa corresponds to position 263 of SEQ ID NO:1
      and is any amino acid, preferably any amino acid that does not
      disrupt the structural fold of the remaining conserved amino acids
```

<400> SEQUENCE: 2

Xaa Xaa Tyr Cys Pro Xaa Xaa Xaa Xaa Pro Pro Glu Tyr Xaa
1               5                   10                  15

Xaa Cys

<210> SEQ ID NO 3
<211> LENGTH: 474
<212> TYPE: PRT
<213> ORGANISM: Ovaloparmena affinis

<400> SEQUENCE: 3

Met Val Arg Tyr Leu Ala Gly Ala Val Leu Leu Val Leu Ser
1               5                   10                  15

Val Ala Ala Val Ser Gly Ala Arg Asp Gly Asp Tyr Leu His Leu
            20                  25                  30

Pro Ser Glu Val Ser Arg Phe Phe Arg Pro Gln Glu Thr Asn Asp Asp
            35                  40                  45

His Gly Glu Asp Ser Val Gly Thr Arg Trp Ala Val Leu Ile Ala Gly
        50                  55                  60

Ser Lys Gly Tyr Ala Asn Tyr Arg His Gln Ala Gly Val Cys His Ala
65                  70                  75                  80

Tyr Gln Ile Leu Lys Arg Gly Gly Leu Lys Asp Glu Asn Ile Val Val
                85                  90                  95

Phe Met Tyr Asp Asp Ile Ala Tyr Asn Glu Ser Asn Pro Arg Pro Gly
            100                 105                 110

Val Ile Ile Asn Ser Pro His Gly Ser Asp Val Tyr Ala Gly Val Pro
            115                 120                 125

Lys Asp Tyr Thr Gly Glu Glu Val Asn Ala Lys Asn Phe Leu Ala Ala
        130                 135                 140

Ile Leu Gly Asn Lys Ser Ala Ile Thr Gly Gly Ser Gly Lys Val Val
145                 150                 155                 160

Asp Ser Gly Pro Asn Asp His Ile Phe Ile Tyr Tyr Thr Asp His Gly
                165                 170                 175

Ala Ala Gly Val Ile Gly Met Pro Ser Lys Pro Tyr Leu Tyr Ala Asp
            180                 185                 190

Glu Leu Asn Asp Ala Leu Lys Lys Lys His Ala Ser Gly Thr Tyr Lys
        195                 200                 205

Ser Leu Val Phe Tyr Leu Glu Ala Cys Glu Ser Gly Ser Met Phe Glu
210                 215                 220

Gly Ile Leu Pro Glu Asp Leu Asn Ile Tyr Ala Leu Thr Ser Thr Asn
225                 230                 235                 240

Thr Thr Glu Ser Ser Trp Cys Tyr Tyr Cys Pro Ala Gln Glu Asn Pro
                245                 250                 255

Pro Pro Pro Glu Tyr Asn Val Cys Leu Gly Asp Leu Phe Ser Val Ala
            260                 265                 270

Trp Leu Glu Asp Ser Asp Val Gln Asn Ser Trp Tyr Glu Thr Leu Asn
        275                 280                 285

Gln Gln Tyr His His Val Asp Lys Arg Ile Ser His Ala Ser His Ala
    290                 295                 300

Thr Gln Tyr Gly Asn Leu Lys Leu Gly Glu Glu Gly Leu Phe Val Tyr
305                 310                 315                 320

Met Gly Ser Asn Pro Ala Asn Asp Asn Tyr Thr Ser Leu Asp Gly Asn
                325                 330                 335

-continued

```
Ala Leu Thr Pro Ser Ser Ile Val Val Asn Gln Arg Asp Ala Asp Leu
                340                 345                 350

Leu His Leu Trp Glu Lys Phe Arg Lys Ala Pro Glu Gly Ser Ala Arg
            355                 360                 365

Lys Glu Glu Ala Gln Thr Gln Ile Phe Lys Ala Met Ser His Arg Val
        370                 375                 380

His Ile Asp Ser Ser Ile Lys Leu Ile Gly Lys Leu Leu Phe Gly Ile
385                 390                 395                 400

Glu Lys Cys Thr Glu Ile Leu Asn Ala Val Arg Pro Ala Gly Gln Pro
                405                 410                 415

Leu Val Asp Asp Trp Ala Cys Leu Arg Ser Leu Val Gly Thr Phe Glu
            420                 425                 430

Thr His Cys Gly Ser Leu Ser Glu Tyr Gly Met Arg His Thr Arg Thr
        435                 440                 445

Ile Ala Asn Ile Cys Asn Ala Gly Ile Ser Glu Glu Gln Met Ala Glu
    450                 455                 460

Ala Ala Ser Gln Ala Cys Ala Ser Ile Pro
465                 470

<210> SEQ ID NO 4
<211> LENGTH: 462
<212> TYPE: PRT
<213> ORGANISM: Clitoria ternatea

<400> SEQUENCE: 4

Ile Arg Asp Asp Phe Leu Arg Leu Pro Ser Gln Ala Ser Lys Phe Phe
1               5                   10                  15

Gln Ala Asp Asp Asn Val Glu Gly Thr Arg Trp Ala Val Leu Val Ala
                20                  25                  30

Gly Ser Lys Gly Tyr Val Asn Tyr Arg His Gln Ala Asp Val Cys His
            35                  40                  45

Ala Tyr Gln Ile Leu Lys Lys Gly Gly Leu Lys Asp Glu Asn Ile Ile
        50                  55                  60

Val Phe Met Tyr Asp Asp Ile Ala Tyr Asn Glu Ser Asn Pro His Pro
65                  70                  75                  80

Gly Val Ile Ile Asn His Pro Tyr Gly Ser Asp Val Tyr Lys Gly Val
                85                  90                  95

Pro Lys Asp Tyr Val Gly Glu Asp Ile Asn Pro Pro Asn Phe Tyr Ala
            100                 105                 110

Val Leu Leu Ala Asn Lys Ser Ala Leu Thr Gly Thr Gly Ser Gly Lys
        115                 120                 125

Val Leu Asp Ser Gly Pro Asn Asp His Val Phe Ile Tyr Tyr Thr Asp
    130                 135                 140

His Gly Gly Ala Gly Val Leu Gly Met Pro Ser Lys Pro Tyr Ile Ala
145                 150                 155                 160

Ala Ser Asp Leu Asn Asp Val Leu Lys Lys Lys His Ala Ser Gly Thr
                165                 170                 175

Tyr Lys Ser Ile Val Phe Tyr Val Glu Ser Cys Glu Ser Gly Ser Met
            180                 185                 190

Phe Asp Gly Leu Leu Pro Glu Asp His Asn Ile Tyr Val Met Gly Ala
        195                 200                 205

Ser Asp Thr Gly Glu Ser Ser Trp Val Thr Tyr Cys Pro Leu Gln His
    210                 215                 220

Pro Ser Pro Pro Pro Glu Tyr Asp Val Cys Val Gly Asp Leu Phe Ser
225                 230                 235                 240
```

```
Val Ala Trp Leu Glu Asp Cys Asp Val His Asn Leu Gln Thr Glu Thr
                245                 250                 255

Phe Gln Gln Gln Tyr Glu Val Val Lys Asn Lys Thr Ile Val Ala Leu
            260                 265                 270

Ile Glu Asp Gly Thr His Val Val Gln Tyr Gly Asp Val Gly Leu Ser
        275                 280                 285

Lys Gln Thr Leu Phe Val Tyr Met Gly Thr Asp Pro Ala Asn Asp Asn
    290                 295                 300

Asn Thr Phe Thr Asp Lys Asn Ser Leu Gly Thr Pro Arg Lys Ala Val
305                 310                 315                 320

Ser Gln Arg Asp Ala Asp Leu Ile His Tyr Trp Glu Lys Tyr Arg Arg
                325                 330                 335

Ala Pro Glu Gly Ser Ser Arg Lys Ala Glu Ala Lys Lys Gln Leu Arg
            340                 345                 350

Glu Val Met Ala His Arg Met His Ile Asp Asn Ser Val Lys His Ile
        355                 360                 365

Gly Lys Leu Leu Phe Gly Ile Glu Lys Gly His Lys Met Leu Asn Asn
    370                 375                 380

Val Arg Pro Ala Gly Leu Pro Val Val Asp Asp Trp Asp Cys Phe Lys
385                 390                 395                 400

Thr Leu Ile Arg Thr Phe Glu Thr His Cys Gly Ser Leu Ser Glu Tyr
                405                 410                 415

Gly Met Lys His Met Arg Ser Phe Ala Asn Leu Cys Asn Ala Gly Ile
            420                 425                 430

Arg Lys Glu Gln Met Ala Glu Ala Ser Gln Ala Cys Val Ser Ile
        435                 440                 445

Pro Asp Asn Pro Trp Ser Ser Leu His Ala Gly Phe Ser Val
    450                 455                 460

<210> SEQ ID NO 5
<211> LENGTH: 488
<212> TYPE: PRT
<213> ORGANISM: Coffea canephora

<400> SEQUENCE: 5

Met Met Arg Tyr Ala Thr Ala Ala Leu Leu Leu Ala Leu Ser Ile
1               5                   10                  15

Ile Ala Val Ala Glu Ala Arg Asp Asn Phe Leu Lys Leu Pro Ser Glu
            20                  25                  30

Ile Ala Asp Phe Phe His Pro Lys Glu Arg Ser Asp Ala Gly Gly Asp
        35                  40                  45

Ser Val Gly Thr Arg Trp Ala Val Leu Ile Ala Gly Ser Asn Gly Tyr
    50                  55                  60

Trp Asn Tyr Arg His Gln Ala Asp Val Cys His Ala Tyr Gln Ile Leu
65                  70                  75                  80

Lys Arg Gly Gly Leu Lys Asp Glu Asn Ile Val Val Phe Met Tyr Asp
                85                  90                  95

Asp Ile Ala Tyr Asn Glu Glu Asn Pro Arg Pro Gly Val Ile Ile Asn
            100                 105                 110

Ser Pro His Gly Ala Asp Val Tyr Gln Gly Val Pro Lys Asp Tyr Thr
        115                 120                 125

Gly Asp Asp Val Asn Ala Lys Asn Phe Leu Ala Ala Ile Leu Gly Asp
    130                 135                 140

Lys Thr Ala Ile Thr Gly Gly Ser Gly Lys Val Val Asp Ser Gly Pro
```

-continued

```
            145                 150                 155                 160
Asn Asp His Ile Phe Ile Tyr Tyr Thr Asp His Gly Gly Pro Gly Val
                165                 170                 175

Leu Gly Thr Pro Ser Gly Pro Tyr Leu Tyr Ala Asp Leu Asn Glu
            180                 185                 190

Val Leu Lys Lys His Ala Ser Gly Thr Tyr Lys Ser Leu Val Phe
        195                 200                 205

Tyr Leu Glu Ala Cys Glu Ser Gly Ser Ile Phe Glu Gly Leu Leu Pro
210                 215                 220

Glu Asp Leu Asn Ile Tyr Ala Thr Thr Ala Ser Asn Ala Glu Glu Ser
225                 230                 235                 240

Ser Trp Gly Thr Tyr Cys Pro Gly Glu Tyr Pro Ser Pro Pro Glu
                245                 250                 255

Tyr Glu Thr Cys Leu Gly Asp Leu Tyr Ser Val Ala Trp Met Glu Asp
                260                 265                 270

Ser Glu Ile His Asn Leu His Thr Glu Thr Leu Lys Gln Gln Tyr His
            275                 280                 285

Leu Val Lys Lys Arg Thr Ser Ser Asn Ser Ala Tyr Gly Ser His
        290                 295                 300

Val Met Gln Tyr Gly Asp Leu Lys Leu Ser Leu Glu Asp Leu Phe Leu
305                 310                 315                 320

Tyr Met Gly Thr Asn Pro Ala Asn Asp Asn Tyr Thr Phe Val Asp Glu
                325                 330                 335

Asn Ser Leu Arg Pro Ser Ser Lys Ala Val Asn Gln Arg Asp Ala Asp
            340                 345                 350

Leu Leu His Phe Trp Asp Lys Phe Arg Lys Ala Pro Glu Gly Ser Ala
        355                 360                 365

Arg Lys Val Glu Ala Gln Lys Gln Val Val Glu Ala Met Ser His Arg
        370                 375                 380

Met His Ile Asp Asn Ser Val Lys Leu Ile Gly Lys Leu Leu Phe Gly
385                 390                 395                 400

Ile Glu Lys Gly Ser Glu Ile Leu Asn Ser Val Arg Pro Ala Gly His
                405                 410                 415

Pro Leu Ala Asp Asp Trp Asp Cys Leu Lys Ser Leu Val Arg Thr Phe
                420                 425                 430

Glu Thr His Cys Gly Ser Leu Ser Gln Tyr Gly Met Lys His Met Arg
            435                 440                 445

Ser Ile Ala Asn Ile Cys Asn Ala Gly Ile Lys Lys Asp Gln Met Ala
        450                 455                 460

Glu Ala Ala Gln Ala Cys Val Ser Leu Pro Ser Asn Ser Trp Ser
465                 470                 475                 480

Ser Leu His Arg Gly Phe Ser Ala
            485

<210> SEQ ID NO 6
<211> LENGTH: 491
<212> TYPE: PRT
<213> ORGANISM: Daucus carota subsp. sativus

<400> SEQUENCE: 6

Met Val Arg Tyr Leu Ala Gly Ala Val Ala Leu Leu Val Val Ser
1               5                  10                  15

Ile Ser Ala Val Val Glu Ser Arg Arg Asp Ile Val Gly Asp Val Leu
            20                  25                  30
```

```
Lys Leu Pro Ser Glu Val Ser Ser Phe Phe Arg Pro Val Ala Glu Glu
             35                  40                  45

Glu Asp Ser Val Gly Thr Arg Trp Ala Val Leu Ile Ala Gly Ser Asn
 50                  55                  60

Gly Tyr Trp Asn Tyr Arg His Gln Ala Asp Ile Cys His Ala Tyr Gln
 65                  70                  75                  80

Leu Leu Arg Arg Gly Val Lys Glu Glu Asn Ile Val Val Phe Met
                 85                  90                  95

Tyr Asp Asp Ile Ala Tyr Asp Glu Glu Asn Pro Arg Pro Gly Val Ile
                100                 105                 110

Ile Asn Ser Pro His Gly Ser Asp Val Tyr Lys Gly Val Pro Lys Asp
                115                 120                 125

Tyr Thr Gly Glu Asp Val Thr Val Asn Asn Val Phe Ala Ala Ile Leu
            130                 135                 140

Gly Asp Lys Ser Ala Thr Thr Gly Gly Ser Gly Lys Val Val Asp Ser
145                 150                 155                 160

Gly Pro Asn Asp His Ile Phe Ile Tyr Tyr Ser Asp His Gly Gly Pro
                    165                 170                 175

Gly Val Leu Gly Met Pro Thr Asn Pro Tyr Met Tyr Ala Gly Asp Leu
                180                 185                 190

Val Asp Val Leu Lys Lys Lys His Ala Ser Gly Thr Tyr Lys Ser Met
            195                 200                 205

Val Phe Tyr Leu Glu Ala Cys Glu Ser Gly Ser Ile Phe Glu Gly Leu
            210                 215                 220

Leu Pro Glu Gly Leu Asn Ile Tyr Ala Thr Thr Ala Ser Asn Ala Tyr
225                 230                 235                 240

Glu Ser Ser Trp Gly Thr Tyr Cys Pro Gly Glu Tyr Pro Ser Pro Pro
                245                 250                 255

Pro Glu Tyr Glu Thr Cys Leu Gly Asp Leu Tyr Ser Val Ala Trp Met
                260                 265                 270

Glu Asp Ser Asp Ile His Asn Leu Arg Thr Glu Thr Leu Arg Gln Gln
            275                 280                 285

Tyr Gln Gln Val Lys Lys Arg Thr Ser Asn Asp Asn Ser Gly Trp Gly
290                 295                 300

Ser His Val Met Gln Tyr Gly Asp Leu Lys Leu Ser Thr Glu Glu Leu
305                 310                 315                 320

Phe Met Tyr Met Gly Thr Asn Pro Ala Asn Asp Asn Phe Thr Phe Val
                325                 330                 335

Asp Asp Asn Ser Leu Arg Leu Ser Ser Lys Ala Val Asn Gln Arg
            340                 345                 350

Asp Ala Asp Leu Leu His Phe Trp Asp Lys Tyr Arg Lys Ala Pro Glu
            355                 360                 365

Gly Ser Asp Arg Lys Ile Ala Ala Gln Lys Gln Phe Ser Glu Ala Met
370                 375                 380

Ser His Arg Met His Leu Asp Asn Ser Ile Gln Leu Ile Gly Lys Leu
385                 390                 395                 400

Leu Phe Gly Ile Asp Thr Ala Ser Glu Val Leu Thr Thr Val Arg Pro
                405                 410                 415

Ser Gly Gln Pro Leu Val Asp Asp Trp Leu Cys Leu Lys Lys Leu Val
                420                 425                 430

Arg Thr Phe Glu Thr Tyr Cys Gly Ser Leu Ser Gln Tyr Gly Met Lys
            435                 440                 445

His Met Arg Ser Ile Ala Asn Ile Cys Asn Ala Gly Ile Ser Glu Glu
```

```
                450            455             460
Gln Met Ser Glu Ala Ser Ala Gln Ala Cys Val Thr Phe Pro Ser Asn
465                 470                 475                 480

Pro Trp Ser Ser Val Asn Lys Gly Phe Thr Ala
                485                 490

<210> SEQ ID NO 7
<211> LENGTH: 486
<212> TYPE: PRT
<213> ORGANISM: Corchorus capsularis

<400> SEQUENCE: 7

Met Thr Arg Leu Val Ala Gly Val Ile Leu Leu Leu Ser Val Thr
1               5                   10                  15

Gly Ile Val Ser Ala Gly Arg Asp Ala Thr Gly Asp Val Leu Arg Leu
                20                  25                  30

Pro Ser Glu Ala Ser Arg Phe Phe Arg Pro Ser Asp Asp Glu Val
                35                  40                  45

Gly Thr Arg Trp Ala Val Leu Ile Ala Gly Ser Asn Gly Tyr Trp Asn
            50                  55                  60

Tyr Arg His Gln Ala Asp Val Cys His Ala Tyr Gln Leu Leu Lys Lys
65                  70                  75                  80

Gly Gly Leu Lys Asp Glu Asn Ile Ile Val Phe Met Tyr Asp Asp Ile
                    85                  90                  95

Ala Tyr Asn Tyr Glu Asn Pro Arg Gln Gly Ile Ile Ile Asn Ser Pro
                100                 105                 110

His Gly Asp Asp Val Tyr Gln Gly Val Pro Lys Asp Tyr Thr Gly Glu
            115                 120                 125

Glu Val Thr Val His Asn Phe Leu Ala Ala Ile Leu Gly Asn Lys Thr
130                 135                 140

Ala Ile Thr Gly Gly Ser Gly Lys Val Val Asp Ser Gly Pro Asn Asp
145                 150                 155                 160

His Ile Phe Ile Tyr Tyr Thr Asp His Gly Gly Pro Gly Val Leu Gly
                165                 170                 175

Met Pro Thr Tyr Pro Tyr Leu Tyr Ala Asp Glu Leu Ile Asp Thr Leu
                180                 185                 190

Lys Lys Lys His Ala Ser Gly Thr Tyr Lys Ser Leu Val Phe Tyr Leu
                195                 200                 205

Glu Ala Cys Glu Ser Gly Ser Ile Phe Glu Gly Leu Leu Pro Glu Gly
210                 215                 220

Leu Asn Ile Tyr Ala Thr Thr Ala Ser Asn Ala Asp Glu Ser Ser Trp
225                 230                 235                 240

Gly Thr Tyr Cys Pro Gly Glu Tyr Pro Ser Pro Pro Glu Tyr Glu
                245                 250                 255

Thr Cys Leu Gly Asp Leu Tyr Ser Val Ala Trp Met Glu Asp Ser Asp
                260                 265                 270

Leu His Asn Leu Arg Thr Glu Thr Leu His Gln Gln Tyr Glu Leu Val
            275                 280                 285

Lys Arg Arg Thr Leu Asn Gly Asn Ser Ala Tyr Gly Ser His Val Met
            290                 295                 300

Gln Tyr Gly Asp Val Gly Leu Ala Lys Glu His Leu Phe Leu Tyr Leu
305                 310                 315                 320

Gly Thr Asn Pro Ala Asn Asp Asn Phe Thr Phe Ile Asp Glu Asn Ser
                325                 330                 335
```

```
Leu Gln Pro Pro Ala Lys Ala Val Asn Gln Arg Asp Ala Asp Leu Val
                340                 345                 350

His Phe Trp Asp Lys Tyr Arg Lys Ala Pro Asp Gly Ser Ala Arg Lys
            355                 360                 365

Val Glu Ala Gln Lys Gln Val Val Glu Ala Met Ser His Arg Met His
        370                 375                 380

Val Asp Asn Ser Ile Gln Leu Ile Gly Lys Leu Leu Phe Gly Ile Glu
385                 390                 395                 400

Arg Gly Ala Asp Val Leu Lys Thr Val Arg Pro Ala Gly Gln Pro Leu
                405                 410                 415

Val Asp Asp Trp Lys Cys Leu Lys Ser Met Val Arg Thr Phe Glu Thr
            420                 425                 430

His Cys Gly Ser Leu Ala Gln Tyr Gly Met Lys His Met Arg Ser Ile
        435                 440                 445

Ala Asn Ile Cys Asn Ala Gly Ile Gln Thr Glu Gln Ile Ala Glu Ala
        450                 455                 460

Ser Ala Gln Ala Cys Val Ser Ile Pro Ser Gly Gln Trp Ser Ser Ile
465                 470                 475                 480

Gln Lys Gly Phe Ser Ala
                485

<210> SEQ ID NO 8
<211> LENGTH: 486
<212> TYPE: PRT
<213> ORGANISM: Corchorus olitorius

<400> SEQUENCE: 8

Met Thr Arg Leu Val Ala Gly Val Ile Leu Leu Leu Ser Val Thr
1               5                   10                  15

Gly Ile Ala Ser Ala Gly Arg Asp Ala Thr Gly Asp Val Leu Arg Leu
            20                  25                  30

Pro Ser Glu Ala Ser Arg Phe Phe Arg Pro Ser Asp Asp Asp Glu Val
        35                  40                  45

Gly Thr Arg Trp Ala Val Leu Ile Ala Gly Ser Asn Gly Tyr Trp Asn
    50                  55                  60

Tyr Arg His Gln Ala Asp Val Cys His Ala Tyr Gln Leu Leu Lys Lys
65                  70                  75                  80

Gly Gly Leu Lys Asp Glu Asn Ile Ile Val Phe Met Tyr Asp Asp Ile
                85                  90                  95

Ala Phe Asn Tyr Glu Asn Pro Arg Gln Gly Ile Ile Ile Asn Ser Pro
            100                 105                 110

His Gly Asp Asp Val Tyr Gln Asp Val Pro Lys Asp Tyr Thr Gly Glu
        115                 120                 125

Glu Val Thr Val His Asn Phe Leu Ala Ala Ile Leu Gly Asn Lys Thr
    130                 135                 140

Ala Ile Lys Gly Gly Ser Gly Lys Val Val Asp Ser Gly Pro Asn Asp
145                 150                 155                 160

His Ile Phe Ile Tyr Tyr Thr Asp His Gly Gly Pro Gly Val Leu Gly
                165                 170                 175

Met Pro Thr Tyr Pro Tyr Leu Tyr Ala Asp Glu Leu Ile Asp Thr Leu
            180                 185                 190

Lys Lys Lys His Ala Ser Gly Thr Tyr Lys Ser Leu Val Phe Tyr Leu
        195                 200                 205

Glu Ala Cys Glu Ser Gly Ser Ile Phe Glu Gly Leu Leu Pro Glu Gly
    210                 215                 220
```

```
Leu Asn Ile Tyr Ala Thr Thr Ala Ser Asn Ala Asp Glu Ser Ser Trp
225                 230                 235                 240

Gly Thr Tyr Cys Pro Gly Glu Tyr Pro Ser Pro Pro Glu Tyr Glu
            245                 250                 255

Thr Cys Leu Gly Asp Leu Tyr Ser Val Ala Trp Met Glu Asp Ser Asp
            260                 265                 270

Leu His Asn Leu Arg Thr Glu Thr Leu His Gln Gln Tyr Glu Leu Val
            275                 280                 285

Lys Arg Arg Thr Leu Asn Gly Asn Ser Ala Tyr Gly Ser His Val Met
            290                 295                 300

Gln Tyr Gly Asp Val Gly Leu Ala Lys Glu His Leu Phe Leu Tyr Leu
305                 310                 315                 320

Gly Thr Asn Pro Ala Asn Asp Asn Phe Thr Phe Ile Asp Glu Asn Ser
            325                 330                 335

Leu Gln Pro Pro Ala Lys Ala Val Asn Gln Arg Asp Ala Asp Leu Val
            340                 345                 350

His Phe Trp Asp Lys Tyr Arg Lys Ala Pro Asp Gly Ser Val Arg Lys
            355                 360                 365

Val Glu Ala Gln Lys Gln Val Val Glu Ala Met Ser His Arg Met His
370                 375                 380

Val Asp Asn Ser Ile Gln Leu Ile Gly Lys Leu Leu Phe Gly Ile Glu
385                 390                 395                 400

Arg Gly Ala Asp Val Leu Lys Thr Val Arg Pro Ala Gly Gln Pro Leu
            405                 410                 415

Val Asp Asp Trp Lys Cys Leu Lys Ser Met Val Arg Thr Phe Glu Thr
            420                 425                 430

His Cys Gly Ser Leu Ala Gln Tyr Gly Met Lys His Met Arg Ser Ile
            435                 440                 445

Ala Asn Ile Cys Asn Ala Gly Ile Gln Thr Glu Gln Met Ala Glu Ala
            450                 455                 460

Ser Ser Gln Ala Cys Val Ser Ile Pro Ser Gly Gln Trp Ser Ser Ile
465                 470                 475                 480

Gln Lys Gly Phe Ser Ala
            485

<210> SEQ ID NO 9
<211> LENGTH: 493
<212> TYPE: PRT
<213> ORGANISM: Jatropha curcas

<400> SEQUENCE: 9

Met Thr Arg Leu Ala Thr Gly Val Ile Leu Leu Leu Ala Leu Cys
1               5                   10                  15

Val Val Ser Ser Ala Gly Ser Arg Asp Ile Val Gly Asp Val Leu Arg
                20                  25                  30

Leu Pro Ser Glu Ala Ser Arg Phe Phe Arg Pro Gly Gly Ala His Val
            35                  40                  45

Ala Lys Glu Asp Asp Ser Thr Gly Thr Arg Trp Ala Ile Leu Ile Ala
50                  55                  60

Gly Ser Asn Gly Tyr Trp Asn Tyr Arg His Gln Ala Asp Val Cys His
65                  70                  75                  80

Ala Tyr Gln Leu Leu Lys Lys Gly Gly Leu Lys Asp Glu Asn Ile Ile
                85                  90                  95

Val Phe Met Tyr Asp Asp Ile Ala Phe Asn Lys Glu Asn Pro Arg Pro
```

```
            100                 105                 110
Gly Val Ile Ile Asn Asn Pro Tyr Gly Glu Asp Val Tyr Lys Gly Val
        115                 120                 125

Pro Lys Asp Tyr Thr Gly Glu Asp Val Asn Val Asn Asn Phe Phe Ala
130                 135                 140

Ala Ile Leu Gly Asn Lys Thr Ala Ile Thr Gly Gly Ser Gly Lys Val
145                 150                 155                 160

Val Asp Ser Gly Pro Asn Asp His Ile Phe Ile Tyr Tyr Thr Asp His
                165                 170                 175

Gly Gly Pro Gly Val Leu Gly Met Pro Thr Asn Pro Tyr Leu Tyr Ala
            180                 185                 190

Asn Asp Leu Ile Asp Val Leu Ile Lys Lys His Ala Ser Gly Thr Tyr
        195                 200                 205

Lys Ser Leu Val Phe Tyr Leu Glu Ala Cys Glu Ser Gly Ser Ile Phe
    210                 215                 220

Glu Gly Leu Leu Pro Glu Gly Leu Asn Ile Tyr Ala Thr Thr Ala Ala
225                 230                 235                 240

Asn Ala Glu Glu Ser Ser Trp Gly Thr Tyr Cys Pro Gly Glu Tyr Pro
                245                 250                 255

Ser Pro Pro Pro Glu Tyr Glu Thr Cys Leu Gly Asp Leu Tyr Ser Val
            260                 265                 270

Ala Trp Met Glu Asp Ser Asp Val His Asn Leu Gln Thr Glu Thr Leu
        275                 280                 285

Arg Gln Gln Tyr Gln Leu Val Lys Arg Arg Thr Ala Asn Gly Asn Ser
    290                 295                 300

Ala Tyr Gly Ser His Val Met Gln Tyr Gly Asp Val Gly Leu Ser Lys
305                 310                 315                 320

Asp Asn Leu Phe Leu Tyr Met Gly Thr Asn Pro Ala Asn Glu Asn Tyr
                325                 330                 335

Thr Phe Val Asp Glu Asn Ser Leu Arg Pro Pro Ser Lys Ala Val Asn
            340                 345                 350

Gln Arg Asp Ala Asp Leu Val His Phe Trp Asp Lys Tyr Arg Lys Ala
        355                 360                 365

Pro Asp Gly Ser Thr Arg Lys Ile Gln Ala Gln Lys Gln Phe Val Glu
    370                 375                 380

Ala Met Ser His Arg Met His Leu Asp His Ser Met Lys Leu Ile Gly
385                 390                 395                 400

Lys Leu Leu Phe Gly Ile Gly Lys Gly Ser Glu Val Leu Asn Ala Ile
                405                 410                 415

Arg Pro Ala Gly Gln Pro Leu Val Asp Asp Trp Val Cys Leu Lys Thr
            420                 425                 430

Leu Val Arg Thr Phe Glu Thr His Cys Gly Ser Leu Ser Gln Tyr Gly
        435                 440                 445

Met Lys His Met Arg Ser Leu Ala Asn Leu Cys Asn Ala Gly Ile Arg
    450                 455                 460

Glu Asp Gln Met Ala Glu Ala Ser Ala Gln Ala Cys Val Ser Ile Pro
465                 470                 475                 480

Ser Gly Pro Trp Ser Ser Leu His Lys Gly Phe Ser Ala
                485                 490
```

<210> SEQ ID NO 10
<211> LENGTH: 494
<212> TYPE: PRT
<213> ORGANISM: Malus hupehensis

<400> SEQUENCE: 10

```
Met Thr Arg Leu Ala Ser Ala Val Val Leu Leu Phe Leu Ala Ser Val
1               5                   10                  15

Leu Ala Ser Ala Ala Gly Ser Arg Asp Leu Ile Gly Asp Val Leu Arg
            20                  25                  30

Leu Pro Ser Glu Ala Ser Arg Phe Phe Gly Arg Gly Asp Asp Ala Pro
            35                  40                  45

Asp Gln Gln Asp Asp Gly Thr Val Gly Thr Arg Trp Ala Val Leu Ile
        50                  55                  60

Ala Gly Ser Asn Gly Tyr Trp Asn Tyr Arg His Gln Ala Asp Ile Cys
65                  70                  75                  80

His Ala Tyr Gln Leu Leu Lys Lys Gly Gly Leu Lys Asp Glu Asn Ile
                85                  90                  95

Val Val Phe Met Tyr Asp Asp Ile Ala Tyr Asn Glu Glu Asn Pro Arg
            100                 105                 110

Gln Gly Val Ile Ile Asn Ser Pro His Gly Ser Asp Val Tyr Glu Gly
            115                 120                 125

Val Pro Lys Asp Tyr Thr Gly Glu Asp Val Thr Val Asn Asn Phe Phe
130                 135                 140

Ala Ala Ile Leu Gly Asn Lys Thr Ala Leu Thr Gly Gly Ser Gly Lys
145                 150                 155                 160

Val Val Asp Ser Gly Pro Asn Asp His Ile Phe Ile Tyr Tyr Thr Asp
                165                 170                 175

His Gly Gly Pro Gly Ile Leu Gly Met Pro Thr Ser Pro Tyr Ile Tyr
            180                 185                 190

Ala Asn Asp Leu Ile Glu Val Leu Lys Lys Lys His Ala Ala Gly Thr
        195                 200                 205

Tyr Arg Ser Leu Val Phe Tyr Leu Glu Ala Cys Glu Ser Gly Ser Ile
        210                 215                 220

Phe Glu Gly Leu Leu Pro Glu Gly Leu Asn Ile Phe Ala Thr Thr Ala
225                 230                 235                 240

Ser Asn Ala Glu Glu Ser Ser Trp Gly Thr Tyr Cys Pro Gly Glu Tyr
            245                 250                 255

Pro Ser Pro Pro Glu Tyr Asp Thr Cys Leu Gly Asp Leu Tyr Ser
            260                 265                 270

Val Ala Trp Met Glu Asp Ser Asp Val His Asn Leu Arg Ser Glu Thr
        275                 280                 285

Leu His Gln Gln Tyr Glu Leu Val Lys Thr Arg Ala Ala Asn Asp Asn
        290                 295                 300

Ser Gly Ser Gly Ser His Val Met Gln Tyr Gly Asp Val Gly Leu Ser
305                 310                 315                 320

Lys Asn Asn Leu Phe Val Tyr Met Gly Thr Asn Pro Ala Asn Asp Asn
                325                 330                 335

Tyr Thr Phe Leu Gly Glu Asn Ser Leu Arg Pro Ser Ser Lys Ala Val
            340                 345                 350

Asn Gln Arg Asp Ala Asp Leu Leu His Phe Trp His Lys Tyr Arg Lys
        355                 360                 365

Ala Pro Glu Gly Ser Ala Arg Lys Ile Gln Ala Gln Lys Asp Phe Val
        370                 375                 380

Glu Ala Met Ser His Arg Met His Ile Asp Gln Thr Met Lys Leu Ile
385                 390                 395                 400

Gly Lys Leu Leu Phe Gly Ile Glu Lys Gly Pro Gln Val Leu Asn Ala
```

```
                        405                 410                 415
Val Arg Pro Ala Gly Gln Pro Leu Val Asp Asp Trp Asp Cys Leu Lys
                420                 425                 430

Thr Met Val Arg Ser Phe Glu Thr His Cys Gly Ser Leu Ser Gln Tyr
            435                 440                 445

Gly Met Lys His Met Arg Ser Leu Ala Asn Ile Cys Asn Ala Gly Met
        450                 455                 460

Thr Gln Glu Gln Met Ala Glu Ala Ser Ala Gln Ala Cys Val Ser Ala
465                 470                 475                 480

Pro Ser Gly Arg Trp Ser Ser Leu His Arg Gly Phe Ser Ala
                485                 490

<210> SEQ ID NO 11
<211> LENGTH: 494
<212> TYPE: PRT
<213> ORGANISM: Pyrus x bretschneideri

<400> SEQUENCE: 11

Met Thr Arg Phe Ala Gly Ala Val Val Leu Phe Leu Ala Ser Val
1               5                   10                  15

Leu Ala Ser Ala Ala Gly Ser Arg Asp Leu Ile Gly Asp Val Leu Arg
                20                  25                  30

Leu Pro Ser Glu Ala Ser Arg Phe Phe Gly Arg Gly Asp Asp Ala Pro
            35                  40                  45

Asp Gln Gln Asp Asp Gly Thr Val Gly Thr Arg Trp Ala Val Leu Ile
50                  55                  60

Ala Gly Ser Asn Gly Tyr Trp Asn Tyr Arg His Gln Ala Asp Ile Cys
65                  70                  75                  80

His Ala Tyr Gln Leu Leu Lys Lys Gly Gly Leu Lys Asp Glu Asn Ile
                85                  90                  95

Val Val Phe Met Tyr Asp Asp Ile Ala Tyr Asn Glu Glu Asn Pro Arg
            100                 105                 110

Gln Gly Val Ile Ile Asn Asn Pro Gln Gly Ser Asp Val Tyr Glu Gly
        115                 120                 125

Val Pro Lys Asp Tyr Thr Gly Glu Asp Val Thr Val Asn Asn Phe Phe
130                 135                 140

Ala Ala Ile Leu Gly Asn Lys Thr Ala Leu Thr Gly Gly Ser Gly Lys
145                 150                 155                 160

Val Val Asp Ser Gly Pro Asn Asp His Ile Phe Ile Tyr Tyr Thr Asp
                165                 170                 175

His Gly Gly Pro Gly Val Leu Gly Met Pro Thr Ser Pro Tyr Ile Tyr
            180                 185                 190

Ala Asn Asp Leu Ile Glu Val Leu Lys Lys Lys His Ala Ala Gly Thr
        195                 200                 205

Tyr Lys Ser Leu Val Phe Tyr Leu Glu Ala Cys Glu Ser Gly Ser Ile
210                 215                 220

Phe Glu Gly Leu Leu Pro Glu Gly Leu Asn Ile Phe Ala Thr Thr Ala
225                 230                 235                 240

Ser Asn Ala Glu Glu Ser Ser Trp Gly Thr Tyr Cys Pro Gly Glu Tyr
                245                 250                 255

Pro Ser Pro Pro Pro Glu Tyr Glu Thr Cys Leu Gly Asp Leu Tyr Ser
            260                 265                 270

Val Ala Trp Met Glu Asp Ser Asp Ile His Asn Leu Arg Ser Glu Thr
        275                 280                 285
```

```
Leu His Gln Gln Tyr Glu Leu Val Lys Thr Arg Thr Ala Asn Asp Asn
    290                 295                 300

Tyr Gly Phe Gly Ser His Val Met Gln Tyr Gly Asp Val Gly Leu Ser
305                 310                 315                 320

Lys Asn Asn Leu Phe Val Tyr Met Gly Thr Asn Pro Ala Asn Asp Asn
                    325                 330                 335

Tyr Thr Phe Leu Gly Glu Asn Ser Leu Arg Pro Ser Ser Lys Ala Val
                340                 345                 350

Asn Gln Arg Asp Ala Asp Leu Leu His Phe Trp His Lys Tyr Arg Lys
            355                 360                 365

Ala Pro Glu Gly Ser Ala Arg Lys Val Gln Ala Gln Lys Asp Phe Val
370                 375                 380

Glu Ala Met Ser His Arg Met His Ile Asp Gln Thr Met Lys Leu Ile
385                 390                 395                 400

Gly Lys Leu Leu Phe Gly Ile Glu Lys Gly Pro Gln Val Leu Asn Ala
                405                 410                 415

Val Arg Pro Ala Gly Gln Pro Leu Val Asp Asp Trp Asp Cys Leu Lys
            420                 425                 430

Thr Met Val Arg Ser Phe Glu Thr His Cys Gly Ser Leu Ser Gln Tyr
                435                 440                 445

Gly Met Lys His Met Arg Ser Leu Ala Asn Ile Cys Asn Ala Gly Met
450                 455                 460

Thr Gln Glu Gln Met Ala Glu Ala Ser Ala Gln Ala Cys Val Ser Ala
465                 470                 475                 480

Pro Ser Ser Arg Trp Ser Ser Leu His Arg Gly Phe Ser Ala
                485                 490
```

<210> SEQ ID NO 12
<211> LENGTH: 537
<212> TYPE: PRT
<213> ORGANISM: artificial sequence
<220> FEATURE:
<223> OTHER INFORMATION: Synthetic Sequence
<400> SEQUENCE: 12

```
Met Gly Met Ala His His His His His His Met Gln Ile Phe Val Lys
1               5                   10                  15

Thr Leu Thr Gly Lys Thr Ile Thr Leu Glu Val Glu Pro Ser Asp Thr
                20                  25                  30

Ile Glu Asn Val Lys Ala Lys Ile Gln Asp Lys Glu Gly Ile Pro Pro
            35                  40                  45

Asp Gln Gln Arg Leu Ile Phe Ala Gly Lys Gln Leu Glu Asp Gly Arg
        50                  55                  60

Thr Leu Ser Asp Tyr Asn Ile Gln Lys Glu Ser Thr Leu His Leu Val
65                  70                  75                  80

Leu Arg Leu Arg Gly Gly Ala Arg Asp Gly Asp Tyr Leu His Leu Pro
                85                  90                  95

Ser Glu Val Ser Arg Phe Phe Arg Pro Gln Glu Thr Asn Asp Asp His
                100                 105                 110

Gly Glu Asp Ser Val Gly Thr Arg Trp Ala Val Leu Ile Ala Gly Ser
            115                 120                 125

Lys Gly Tyr Ala Asn Tyr Arg His Gln Ala Gly Val Cys His Ala Tyr
130                 135                 140

Gln Ile Leu Lys Arg Gly Gly Leu Lys Asp Glu Asn Ile Val Val Phe
145                 150                 155                 160
```

```
Met Tyr Asp Asp Ile Ala Tyr Asn Glu Ser Asn Pro Arg Pro Gly Val
                165                 170                 175
Ile Ile Asn Ser Pro His Gly Ser Asp Val Tyr Ala Gly Val Pro Lys
            180                 185                 190
Asp Tyr Thr Gly Glu Glu Val Asn Ala Lys Asn Phe Leu Ala Ala Ile
        195                 200                 205
Leu Gly Asn Lys Ser Ala Ile Thr Gly Gly Ser Gly Lys Val Val Asp
    210                 215                 220
Ser Gly Pro Asn Asp His Ile Phe Ile Tyr Tyr Thr Asp His Gly Ala
225                 230                 235                 240
Ala Gly Val Ile Gly Met Pro Ser Lys Pro Tyr Leu Tyr Ala Asp Glu
                245                 250                 255
Leu Asn Asp Ala Leu Lys Lys Lys His Ala Ser Gly Thr Tyr Lys Ser
            260                 265                 270
Leu Val Phe Tyr Leu Glu Ala Cys Glu Ser Gly Ser Met Phe Glu Gly
        275                 280                 285
Ile Leu Pro Glu Asp Leu Asn Ile Tyr Ala Leu Thr Ser Thr Asn Thr
    290                 295                 300
Thr Glu Ser Ser Trp Cys Tyr Tyr Cys Pro Ala Gln Glu Asn Pro Pro
305                 310                 315                 320
Pro Pro Glu Tyr Asn Val Cys Leu Gly Asp Leu Phe Ser Val Ala Trp
                325                 330                 335
Leu Glu Asp Ser Asp Val Gln Asn Ser Trp Tyr Glu Thr Leu Asn Gln
            340                 345                 350
Gln Tyr His His Val Asp Lys Arg Ile Ser His Ala Ser His Ala Thr
        355                 360                 365
Gln Tyr Gly Asn Leu Lys Leu Gly Glu Glu Gly Leu Phe Val Tyr Met
    370                 375                 380
Gly Ser Asn Pro Ala Asn Asp Asn Tyr Thr Ser Leu Asp Gly Asn Ala
385                 390                 395                 400
Leu Thr Pro Ser Ser Ile Val Val Asn Gln Arg Asp Ala Asp Leu Leu
                405                 410                 415
His Leu Trp Glu Lys Phe Arg Lys Ala Pro Glu Gly Ser Ala Arg Lys
            420                 425                 430
Glu Glu Ala Gln Thr Gln Ile Phe Lys Ala Met Ser His Arg Val His
        435                 440                 445
Ile Asp Ser Ser Ile Lys Leu Ile Gly Lys Leu Leu Phe Gly Ile Glu
    450                 455                 460
Lys Cys Thr Glu Ile Leu Asn Ala Val Arg Pro Ala Gly Gln Pro Leu
465                 470                 475                 480
Val Asp Asp Trp Ala Cys Leu Arg Ser Leu Val Gly Thr Phe Glu Thr
                485                 490                 495
His Cys Gly Ser Leu Ser Glu Tyr Gly Met Arg His Thr Arg Thr Ile
            500                 505                 510
Ala Asn Ile Cys Asn Ala Gly Ile Ser Glu Glu Gln Met Ala Glu Ala
        515                 520                 525
Ala Ser Gln Ala Cys Ala Ser Ile Pro
    530                 535

<210> SEQ ID NO 13
<211> LENGTH: 10
<212> TYPE: PRT
<213> ORGANISM: artificial sequence
<220> FEATURE:
<223> OTHER INFORMATION: Synthetic Sequence
```

<400> SEQUENCE: 13

Met Gly Met Ala His His His His His His
1               5                   10

<210> SEQ ID NO 14
<211> LENGTH: 76
<212> TYPE: PRT
<213> ORGANISM: artificial sequence
<220> FEATURE:
<223> OTHER INFORMATION: Synthetic Sequence

<400> SEQUENCE: 14

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 15
<211> LENGTH: 450
<212> TYPE: PRT
<213> ORGANISM: Ovaloparmena affinis

<400> SEQUENCE: 15

Ala Arg Gly Asp Tyr Leu His Leu Pro Ser Glu Val Ser Arg Phe Phe
1               5                   10                  15

Arg Pro Gln Glu Thr Asn Asp Asp His Gly Glu Asp Ser Val Gly Thr
            20                  25                  30

Arg Trp Ala Val Leu Ile Ala Gly Ser Lys Gly Tyr Ala Asn Tyr Arg
        35                  40                  45

His Gln Ala Gly Val Cys His Ala Tyr Gln Ile Leu Lys Arg Gly Gly
    50                  55                  60

Leu Lys Asp Glu Asn Ile Val Val Phe Met Tyr Asp Asp Ile Ala Tyr
65                  70                  75                  80

Asn Glu Ser Asn Pro Arg Pro Gly Val Ile Ile Asn Ser Pro His Gly
            85                  90                  95

Ser Asp Val Tyr Ala Gly Val Pro Lys Asp Tyr Thr Gly Glu Glu Val
            100                 105                 110

Asn Ala Lys Asn Phe Leu Ala Ala Ile Leu Gly Asn Lys Ser Ala Ile
        115                 120                 125

Thr Gly Gly Ser Gly Lys Val Val Asp Ser Gly Pro Asn Asp His Ile
    130                 135                 140

Phe Ile Tyr Tyr Thr Asp His Gly Ala Ala Gly Val Ile Gly Met Pro
145                 150                 155                 160

Ser Lys Pro Tyr Leu Tyr Ala Asp Glu Leu Asn Asp Ala Leu Lys Lys
            165                 170                 175

Lys His Ala Ser Gly Thr Tyr Lys Ser Leu Val Phe Tyr Leu Glu Ala
            180                 185                 190

Cys Glu Ser Gly Ser Met Phe Glu Gly Ile Leu Pro Glu Asp Leu Asn
        195                 200                 205

Ile Tyr Ala Leu Thr Ser Thr Asn Thr Thr Glu Ser Ser Trp Cys Tyr

-continued

```
              210                 215                 220

Tyr Cys Pro Ala Gln Glu Asn Pro Pro Pro Glu Tyr Asn Val Cys
225                 230                 235                 240

Leu Gly Asp Leu Phe Ser Val Ala Trp Leu Glu Asp Ser Asp Val Gln
                245                 250                 255

Asn Ser Trp Tyr Glu Thr Leu Asn Gln Gln Tyr His His Val Asp Lys
                260                 265                 270

Arg Ile Ser His Ala Ser His Ala Thr Gln Tyr Gly Asn Leu Lys Leu
                275                 280                 285

Gly Glu Glu Gly Leu Phe Val Tyr Met Gly Ser Asn Pro Ala Asn Asp
290                 295                 300

Asn Tyr Thr Ser Leu Asp Gly Asn Ala Leu Thr Pro Ser Ser Ile Val
305                 310                 315                 320

Val Asn Gln Arg Asp Ala Asp Leu Leu His Leu Trp Glu Lys Phe Arg
                325                 330                 335

Lys Ala Pro Glu Gly Ser Ala Arg Lys Glu Ala Gln Thr Gln Ile
                340                 345                 350

Phe Lys Ala Met Ser His Arg Val His Ile Asp Ser Ser Ile Lys Leu
                355                 360                 365

Ile Gly Lys Leu Leu Phe Gly Ile Glu Lys Cys Thr Glu Ile Leu Asn
370                 375                 380

Ala Val Arg Pro Ala Gly Gln Pro Leu Val Asp Asp Trp Ala Cys Leu
385                 390                 395                 400

Arg Ser Leu Val Gly Thr Phe Glu Thr His Cys Gly Ser Leu Ser Glu
                405                 410                 415

Tyr Gly Met Arg His Thr Arg Thr Ile Ala Asn Ile Cys Asn Ala Gly
                420                 425                 430

Ile Ser Glu Glu Gln Met Ala Glu Ala Ser Gln Ala Cys Ala Ser
                435                 440                 445

Ile Pro
    450

<210> SEQ ID NO 16
<211> LENGTH: 38
<212> TYPE: DNA
<213> ORGANISM: artificial sequence
<220> FEATURE:
<223> OTHER INFORMATION: primer used for mutagenesis

<400> SEQUENCE: 16
caccaccgaa agcagctggg cctactattg cccggcgc                              38

<210> SEQ ID NO 17
<211> LENGTH: 14
<212> TYPE: PRT
<213> ORGANISM: artificial sequence
<220> FEATURE:
<223> OTHER INFORMATION: Peptide template used for characterizing
      recognition sequence specificity of Quicklase
<220> FEATURE:
<221> NAME/KEY: MISC_FEATURE
<222> LOCATION: (1)..(1)
<223> OTHER INFORMATION: Xaa is any amino acid. In each screen, only one
      of the residue is modified. The default amino acid at Xaa1
      position is Gly, at Xaa2 position is Leu, and at Xaa3 position is
      Gly, and at the Xaa4 position is Leu, in this screen.
<220> FEATURE:
<221> NAME/KEY: MISC_FEATURE
<222> LOCATION: (2)..(2)
<223> OTHER INFORMATION: Xaa is any amino acid. In each screen, only one
      of the residue is modified. The default amino acid at Xaa1
```

```
       position is Gly, at Xaa2 position is Leu, and at Xaa3 position is
       Gly, and at the Xaa4 position is Leu, in this screen.
<220> FEATURE:
<221> NAME/KEY: MISC_FEATURE
<222> LOCATION: (13)..(13)
<223> OTHER INFORMATION: Xaa is any amino acid. In each screen, only one
       of the residue is modified. The default amino acid at Xaa1
       position is Gly, at Xaa2 position is Leu, and at Xaa3 position is
       Gly, and at the Xaa4 position is Leu, in this screen.
<220> FEATURE:
<221> NAME/KEY: MISC_FEATURE
<222> LOCATION: (14)..(14)
<223> OTHER INFORMATION: Xaa is any amino acid. In each screen, only one
       of the residue is modified. The default amino acid at Xaa1
       position is Gly, at Xaa2 position is Leu, and at Xaa3 position is
       Gly, and at the Xaa4 position is Leu, in this screen.

<400> SEQUENCE: 17

Xaa Xaa Tyr Arg Arg Gly Arg Leu Tyr Arg Arg Asn Xaa Xaa
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 18

Gly Leu Pro Val Ser Thr Lys Pro Val Ala Thr Arg Asn Gly Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 19

Gly Leu Pro Val Ser Thr Lys Pro Val Ala Thr Arg Asn His Val
1               5                   10                  15
```

METHODS FOR ENZYMATIC PEPTIDE LIGATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is Corrected_SequenceListing_690148_522USPC.txt. The text file is 54.8 KB, was created on Aug. 23, 2021, and is being submitted electronically via EFS-Web.

CROSS-REFERENCE TO RELATED APPLICATION

This application makes reference to and claims the benefit of priority of the Singapore Patent Application No. 10201607951V filed on 23 Sep. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to Asx-specific peptide ligases, methods of enzymatically ligating peptides using said ligases and the thus generated peptides and peptide-containing complexes.

BACKGROUND OF THE INVENTION

Unlike proteases that are abundantly found in nature, peptide ligases are relatively rare. The first asparagine/aspartate (Asx) peptide ligase reported was butelase 1, purified from the cyclotide-producing plant *Clitoria ternatea* (Nguyen, G. K., et al., Nat Chem Biol, 2014. 10(9): p. 732-8). Compared to bacterial sortase which is commonly used to catalyze transpeptidation reactions in vitro, butelase 1 shows exceptionally high efficiency in catalyzing both peptide and protein ligation reactions, opening a wide range of applications in biotechnology, protein engineering, chemoenzymatic synthesis and protein labeling. Recently an asparaginyl endopeptidase (AEP) evolutionary related to butelase 1 named OaAEP1b, also having the ability to link the N- and C-termini of peptidyl substrates, was isolated from the plant *Oldenlandia affinis* and expressed using *E. coli* in an active form following activation at acidic pH. Both butelase 1 and OaAEP1b use the amino acid(s) Asx at the ligation site and have 65% amino-acid sequence identity. However, the reported catalytic efficiency of OaAEP1b is markedly lower than butelase 1 (Harris, K. S., et al., Nat Commun, 2015. 6: p. 10199). In addition, the structural and catalytic mechanisms underlying this family of protein ligases were poorly understood. Therefore, there is still need in the art for new developments that overcome the drawbacks of existing techniques, in particular new methods that allow efficient peptide ligation.

SUMMARY OF THE INVENTION

The present invention satisfies the aforementioned need in the art by providing the methods described herein.

In a first aspect, the present invention relates to a method of generating a peptide of Formula (I)

$$P^1\text{-Asx-Xaa}^1\text{-Xaa}^2\text{-}P^2 \qquad (I),$$

by ligating a first peptide of Formula (II)

$$P^1\text{-Asx-Xaa}^3\text{-Leu-COOH/CONH}_2 \qquad (II)$$

to a second peptide of Formula (III)

$$H_2N\text{-Xaa}^1\text{-Xaa}^2\text{-}P^2 \qquad (III),$$

wherein $P^1$ and $P^2$ are each independently any peptide, modified or unmodified, and optionally can combine such that the peptides of formula (II) and (III) are the termini of the same peptide; Asx is Asp or Asn; $Xaa^1$ is any naturally occurring amino acid; $Xaa^2$ is any naturally occurring amino acid with the exception of Pro, preferably Leu or Ile; and $Xaa^3$ is any naturally occurring amino acid, preferably selected from the group consisting of His, Ala, Ser, Cys, Asn, Gly, Arg, Met, Lys, Gln, Leu, and Glu, by enzymatically cleaving the bond between "Asx" and "$Xaa^3$" in the first peptide of Formula (II) and ligating the fragment $P^1$-Asx of the first peptide via its C-terminus to the N-terminus of the second peptide of Formula (III) to form a ligated peptide of Formula (I), wherein the enzymatic cleavage and ligation reaction is catalyzed by a peptide ligase having the activity of OaAEP1 Cys247Ala (SEQ ID NO:1, also termed "Quicklase" hereinafter) under conditions suitable for said cleavage and ligation reaction.

In various embodiments, the first and second peptides are the termini of the same peptide (i.e. $P^1$ and $P^2$ combine to form a single core peptide sequence) such that the method cyclizes said peptide.

In various embodiments, the peptide ligase having the activity of OaAEP1 Cys247Ala (SEQ ID NO:1) comprises or consists of:

(a) the amino acid sequence set forth in SEQ ID NO:1;
(b) an amino acid sequence that shares at least 65%, preferably at least 75%, even more preferably at least 85%, most preferably at least 95% sequence identity with, or at least 80%, preferably at least 90%, more preferably at least 95% sequence homology with the amino acid sequence as set forth in SEQ ID NO:1, provided that said peptide ligase comprises the amino acid sequence set forth in SEQ ID NO:2 at the positions corresponding to residues 247-264 of SEQ ID NO:1;
(c) a functional fragment of (a) or (b); or
(d) an amino acid sequence containing either (a) or (b) or (c) as its essential component, with the proviso that said peptide ligase is not the wild-type OaAEP1 having the amino acid sequence set forth in SEQ ID NO:3 or butelase 1 having the amino acid sequence set forth in SEQ ID NO:4.

In various embodiments, the peptide ligase having the activity of OaAEP1 Cys247Ala (SEQ ID NO:1) comprises or consists of:

(a) the amino acid sequence set forth in SEQ ID NO:1;
(b) the amino acid sequence set forth in SEQ ID NO:5;
(c) the amino acid sequence set forth in SEQ ID NO:6;
(d) the amino acid sequence set forth in SEQ ID NO:7;
(e) the amino acid sequence set forth in SEQ ID NO:8;
(f) the amino acid sequence set forth in SEQ ID NO:9;
(g) the amino acid sequence set forth in SEQ ID NO:10; or
(h) the amino acid sequence set forth in SEQ ID NO:11.

In various embodiments, the first and/or second peptide further comprises a labeling moiety.

In various embodiments, the labeling moiety is an affinity tag, therapeutic agent, detectable label, or scaffold molecule.

In various embodiments, the first and/or second peptide may be coupled to a solid support material.

In various embodiments, the first and/or second peptide is a cellular surface protein such that the method results in the modification or tagging of the cellular surface protein and in result the cellular surface as such.

In a second aspect, the present invention relates to a method of preparing a dimer, oligomer, or multimer of one or more peptides of interest, the method comprising the steps of:

(a) providing one or more peptides of interest having C-terminal Asx-Xaa$^3$-Leu-COOH/CONH$_2$ residues and a scaffold molecule having two or more copies of N-terminal H$_2$N-Xaa$^1$-Xaa$^2$ residues or, alternatively, providing one or more peptides of interest having N-terminal H$_2$N-Xaa$^1$-Xaa$^2$ residues and a scaffold molecule having two or more copies of C-terminal Asx-Xaa$^3$-Leu-COOH/CONH$_2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1);

(c) preparing a mixture of the one or more peptides of interest, the scaffold molecule, and the peptide ligase having the activity of OaAEP1 Cys247Ala (SEQ ID NO:1);

(d) subjecting the mixture to conditions that allow the peptide ligase having the activity of OaAEP1 Cys247Ala (SEQ ID NO:1) to catalyze the ligation of the one or more peptides of interest to the scaffold molecule.

In a third aspect, the present invention relates to a method of modifying or tagging the surface of a target cell by one or more peptides of interest, the method comprising the steps of:

(a) providing the one or more peptides of interest having C-terminal Asx-Xaa$^3$-Leu-COOH/CONH$_2$ residues and/or having N-terminal H$_2$N-Xaa$^1$-Xaa$^2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1);

(c) contacting the target cell with the one or more peptides of interest and the peptide ligase having the activity of OaAEP1 Cys247Ala (SEQ ID NO:1);

(d) subjecting the target cell to conditions that allow the peptide ligase having the activity of OaAEP1 Cys247Ala (SEQ ID NO:1) to catalyze the ligation of the one or more peptides of interest to a cellular surface protein of the target cell.

In various embodiments, the method further comprises removing the unligated one or more peptides from the target cell after step (d).

In various embodiments, the one or more peptides of interest comprise a labeling moiety, as already described above.

In various embodiments, the target cell recombinantly expresses a surface polypeptide having N-terminal H$_2$N-Xaa$^1$-Xaa$^2$ residues or C-terminal Asx-Xaa$^3$-Leu-COON residues for ease of tagging by the peptide of interest.

In various embodiments of all afore-described aspects of the invention, (a) Asx is Asn or Asp; and/or
(b) Xaa$^1$ is all naturally occurring amino acids; and/or
(c) Xaa$^2$ is Leu or Ile; and/or
(d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e. (a) and (b), (a) and (c), (a) and (d), (b) and (c), (b) and (d), or three or more features are met, i.e. (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly.

In a fourth aspect, the invention relates to the ligated peptides and/or tagged target cells obtainable according to any of the methods of the invention.

In a fifth aspect, the invention relates to the peptide ligase OaAEP1 Cys247Ala having the amino acid sequence of SEQ ID NO:1 and other peptide ligases having the activity thereof, as described above, as well as kits comprising any of said peptide ligases, in particular OaAEP1 Cys247Ala (SEQ ID NO:1).

In still another aspect, the present invention relates to the use of a peptide ligase having the activity of OaAEP1 Cys247Ala (SEQ ID NO:1) for the ligation of two peptides, as described herein.

It is understood that all embodiments disclosed herein in relation to one aspect of the invention, are similarly applicable to all other aspects of the invention.

BRIEF DESCRIPTION OF THE DRAWINGS

The invention will be better understood with reference to the detailed description when considered in conjunction with the non-limiting examples and the accompanying drawings.

FIG. 3 shows a crystal structure of OaAEP1 in its zymogenic form. (a) Overall "front" view of the OaAEP1 structure represented as "cartoon" (with α-helices as ribbons and β-strands as arrows) with the catalytic core domain colored in green, the pro-domain in purple. The flexible linker spanning residues 325-343 (not visible) is depicted as dashed line and residues 344-347 that are trapped in the OaAEP1 active site are depicted as sticks. The molecular surface views in panels (b) and (c) were obtained by separating the core domain from the cap domain and rotating by an angle of 90° in opposite directions respectively (indicated by arrows). (d) The OaAEP1 inactive dimer is stabilized via intermolecular interactions provided by the cap region. Residues 344-347 that are bound in the active site are depicted as sticks and labeled.

Compared to human legumain, these linker residues are bound at the catalytic center in an orientation similar to peptide based legumain inhibitors. From this comparative view, the putative channel that accommodates the incoming amine could be identified on the core domain surface. The orientation of an incoming substrate poised to undergo the ligation reaction is indicated by an arrow along the channel at the protein surface (see text). (e) The hlegum molecular surface is shown in the same orientation as OaAEP1 with the peptide Ac-Tyr-Val-Ala-Asp-CMK (sticks) covalently bound to the active site Cys189 (from PDB code: 4AWA). Here, the incoming amine channel is completely blocked, explaining the lack of significant ligase activity. (f) A cartoon highlight the two critical structural features related to the substrates binding and catalytic activities of OaAEP1 Cys247Ala. P1 binding site is responsible for efficient cleavage, and P2 binding site is related to efficient protein ligation.

Figure 4:
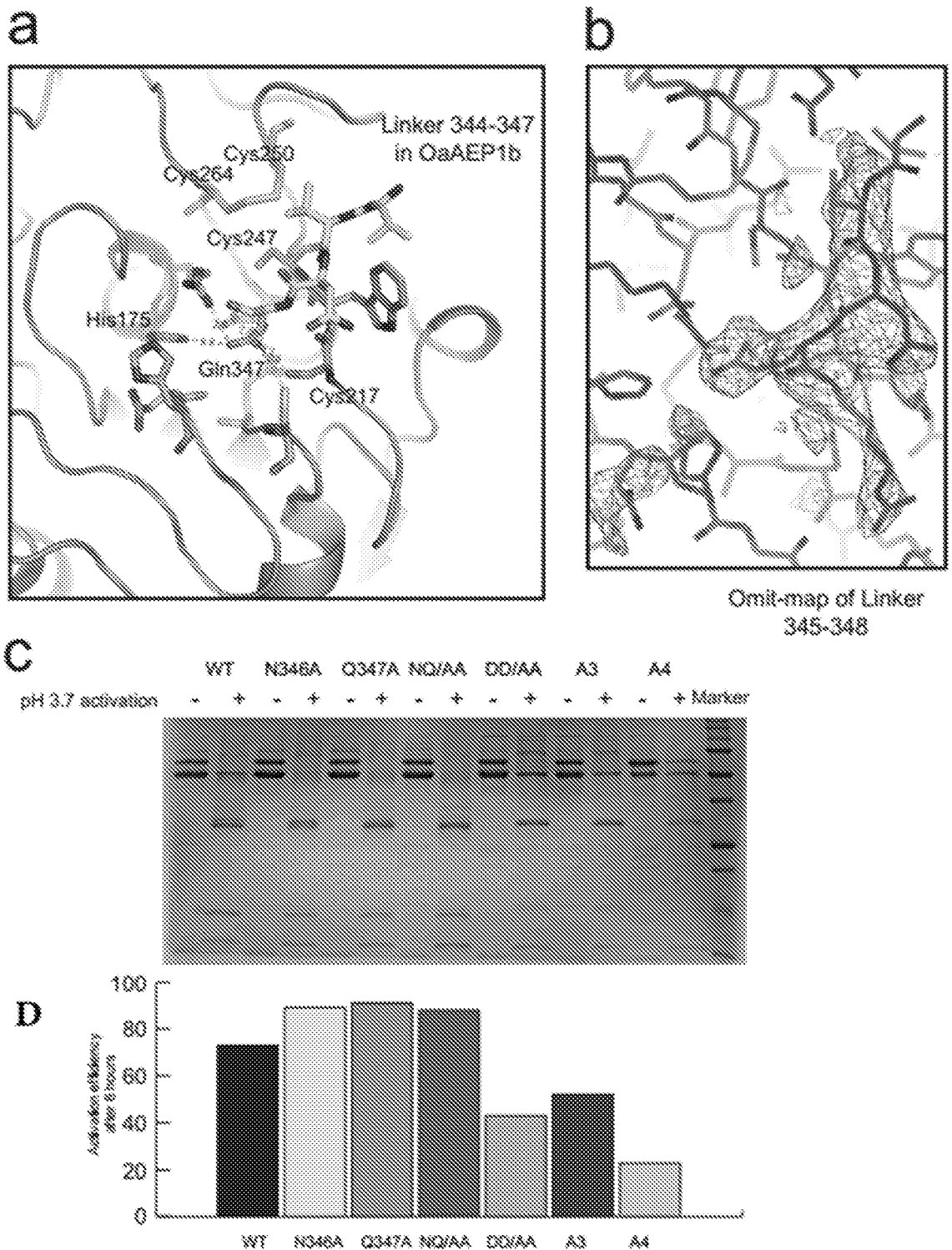

FIG. 4 shows the OaAEP1 active-site and the activation segment. (a) Close-up view of the OaAEP1 active site with active site residues discussed in the text displayed as sticks and labeled: The canonical AEP catalytic pair His175 and Cys217 and the linker residues 344-347 bound at the catalytic center are depicted as sticks. Also shown the disulfide bond formed by Cys250 and Cys264 (conserved in butelase 1), which forms an open amine incoming channel and the "gate-keeper" Cys247 a major determinant for the ligase activity. Hydrogen bonds formed by P1 residue Gln347 which is bound in the S1 pocket are depicted by dashed lines and interatomic distances are displayed in Å. Panel (b) displays an electron density map with the segment 344-347 of the polypeptide omitted from the phase calculation and contoured at 3σ level. (c) Residual activation of OaAEP1 mutants following site-directed mutagenesis targeting the activation segment 346-351. Enzymatic behavior of linker mutants: Single or double mutations of Asn346, Gln347, Asp349 and Asp351 demonstrated moderate loss of self-cleavage induced activation. Triple mutant A3 (Asn346Ala, Asp349Ala and Asp351Ala) and quadruple mutant A4 (Asn346, Gln347, Asp349 and Asp351) have more severe loss of function phenotype, indicating the site of activation could be any residue with this stretch of linker. (d) An histogram of activation efficiency after 6 hours is shown for the linker mutants. Asp349 and Asp351 could be the more preferred cleavage site, while Asn346 and Gln347 are potential cleavage sites as well.

Figure 5:
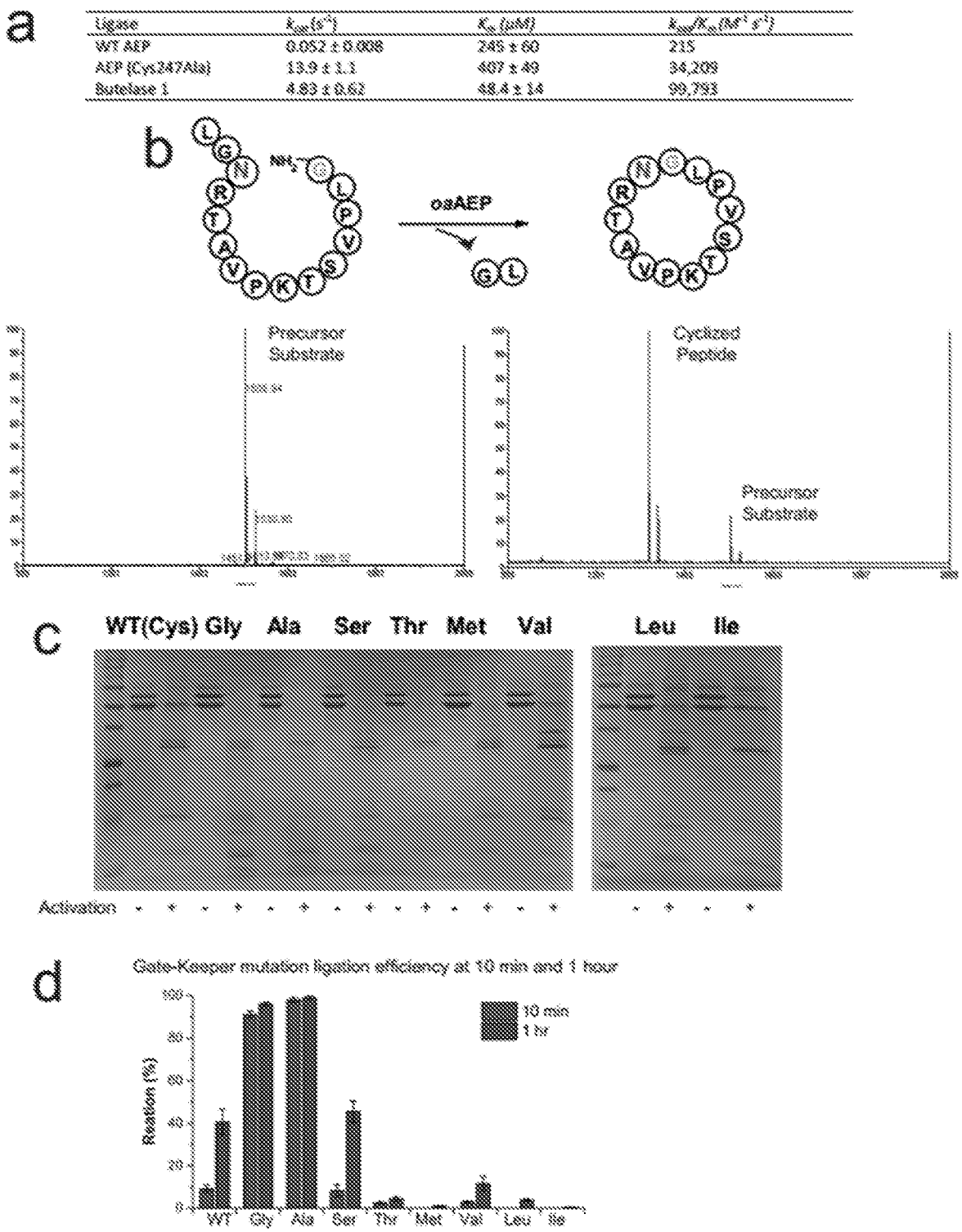

FIG. 5 shows comparison of peptide cyclization activity of WT OaEP1b, Cys247Ala and butelase 1 and the influence of the gate-keeper on ligase activity. (a) Kinetic parameters for the cyclization of "GLPVSTKPVATRNGL" (SEQ ID NO: 18) by WT OaEP1b, Cys247Ala and butelase 1. MS analysis of the reaction is given in panel (b). (c) Role of the gate-keeper in OaAEP1 activation. (d) Comparison of cyclization efficiency for various residues at the gate-keeper Cys247 position. The Gate-keeper residue Cys247 governs the ligation reaction kinetics. (a) The kinetic measurement of wild type OaAEP1 and Cys247Ala mutant, in comparison with Butelase 1 freshly extracted from plant. Cys247Ala has the Kcat/Km 160 times faster than wt OaAEP1b. (b) The schematic view of the peptide used to determine the ligation efficiency, together with the mass-spec results demonstrating the backbone ligation achieved by wild type OaAEP1 and Cys247Ala mutant. (c) The self-activation of the gate-keeper mutants. The self-activation is not much affected by mutations of the gate-keeper residue. Bulky side chain mutants have difficulties been fully activated. (d) The ligation catalytic activity is reversely correlated with the size of the side chain of Cys247 mutants.

Figure 6:
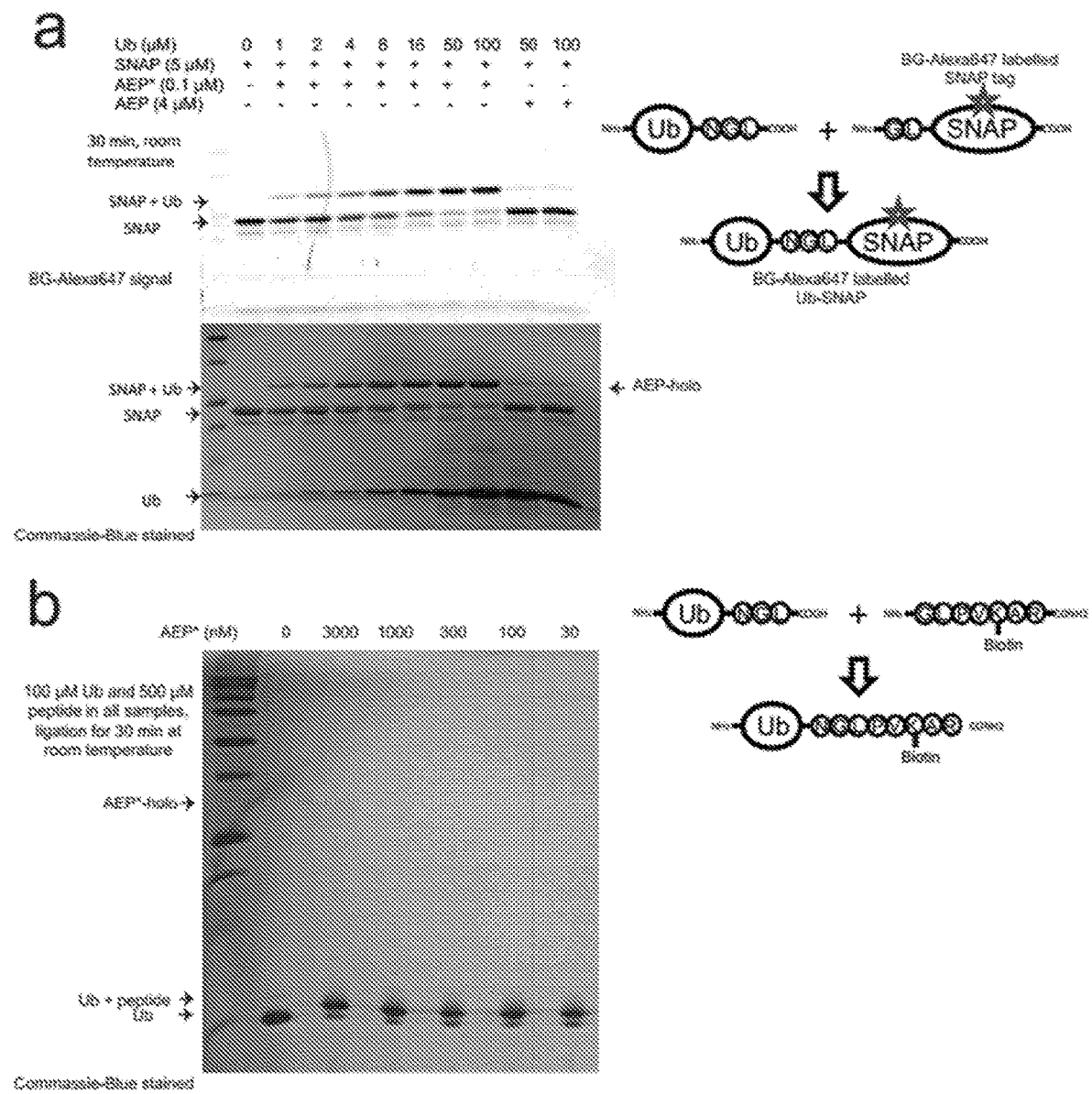

FIG. 6 shows protein ligase activity of Cys247Ala. (a) Fluorescence detection using 02 benzylcytosine-Alexa647 of the SNAP protein and SDS PAGE analysis with Comassie blue staining detection of the protein substrate and ligated products. The reaction is schematically depicted as inset. Cys247Ala ligates well folded protein well. (a) 100 nM of Cys247Ala, but not 4000 nM of wild type OaAEP1b, efficiently ligated 5 μM C-terminal modified SNAP tag protein with N-terminal modified Ubiquitin. (b) As little as 30 nM Cys247Ala catalyze ligation of 100 μM Ubiquitin and 500 μM biotin labelled peptide efficiently in 30 min, at room temperature, in pH 7.4 PBS buffer.

Figure 7:
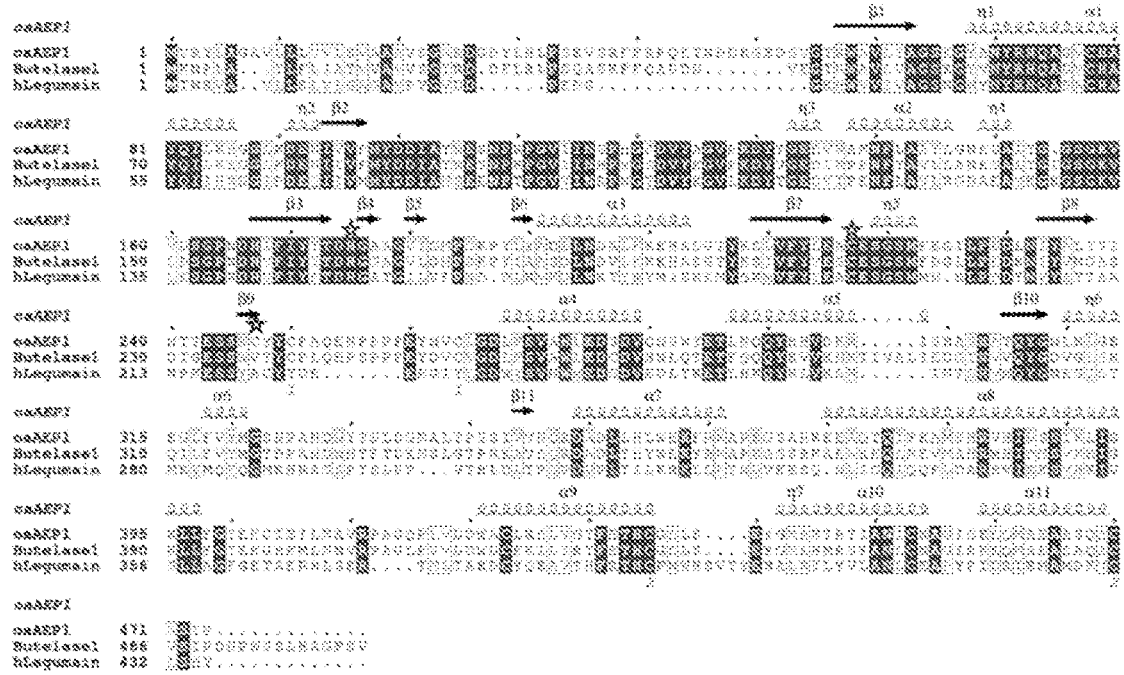

FIG. 7 shows (a) sequence alignment of OaAEP1 b, Butelase 1 and human legumain. (b) The exact amino acid sequence encoded in our OaAEP1 construct. Residues −85 to 0 is the fusion tags (colored in cyan), while the first 23 amino acids in AEP coding was omitted. The four residues inserted at the active site pocket observed in our crystal structure are colored in orange, and the cap domain is displayed in violet.

Figure 8:
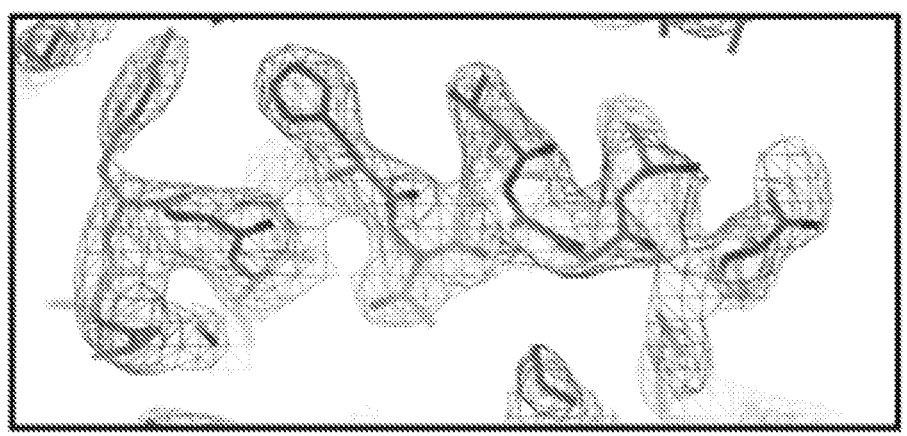
Figure 8:
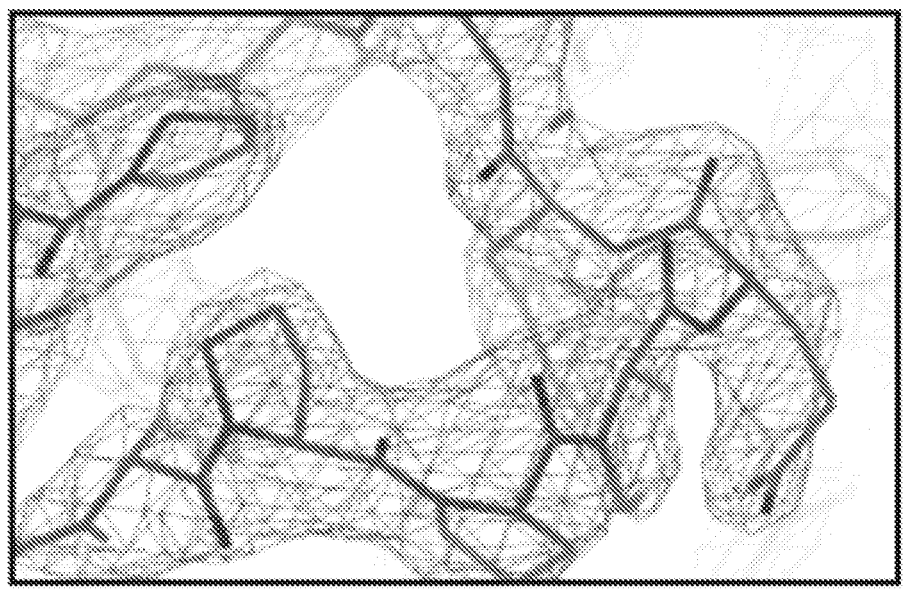

FIG. 8 shows the 2FO-FC electron density map, highlighting the good fitting of the model. (a) side chains in the cap domain are well fit with the density. (b) the novel PPP loop in the core domain, which is unique to AEP ligases are nicely fit with the density.

Figure 9:
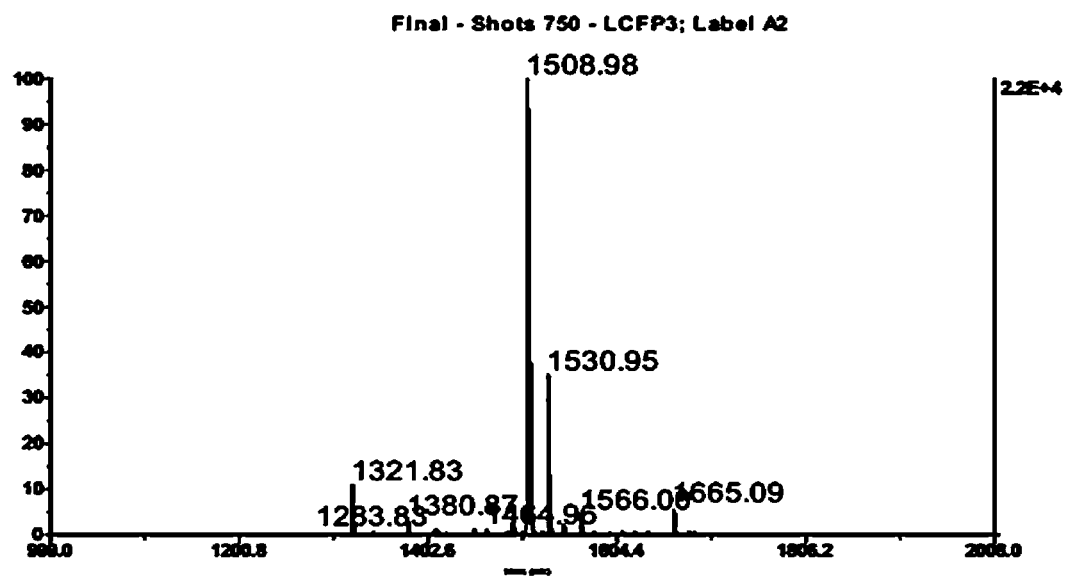
Figure 9:
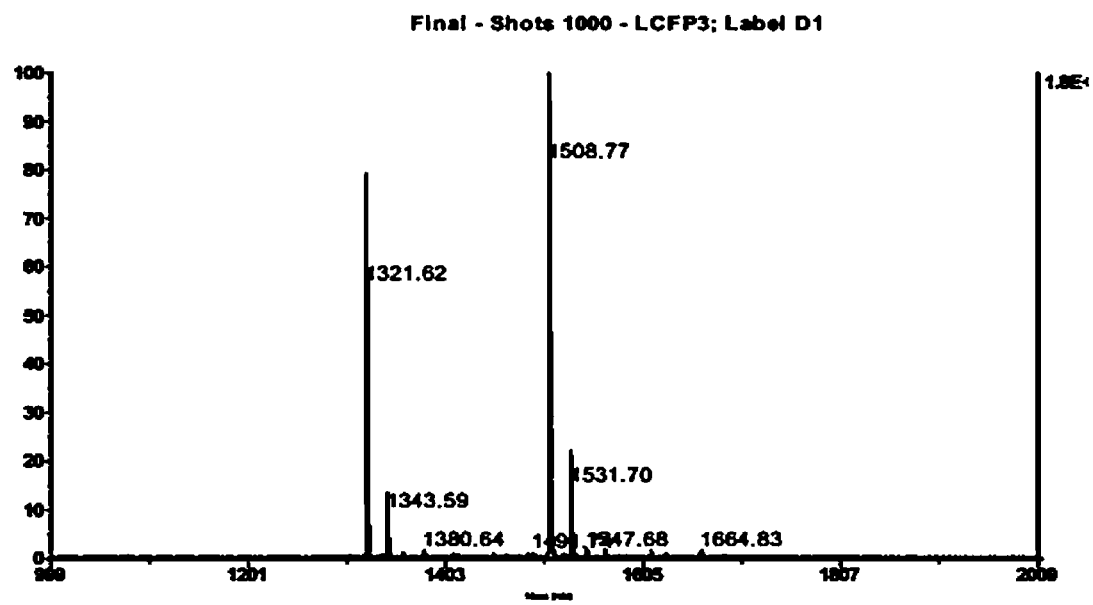
Figure 9:
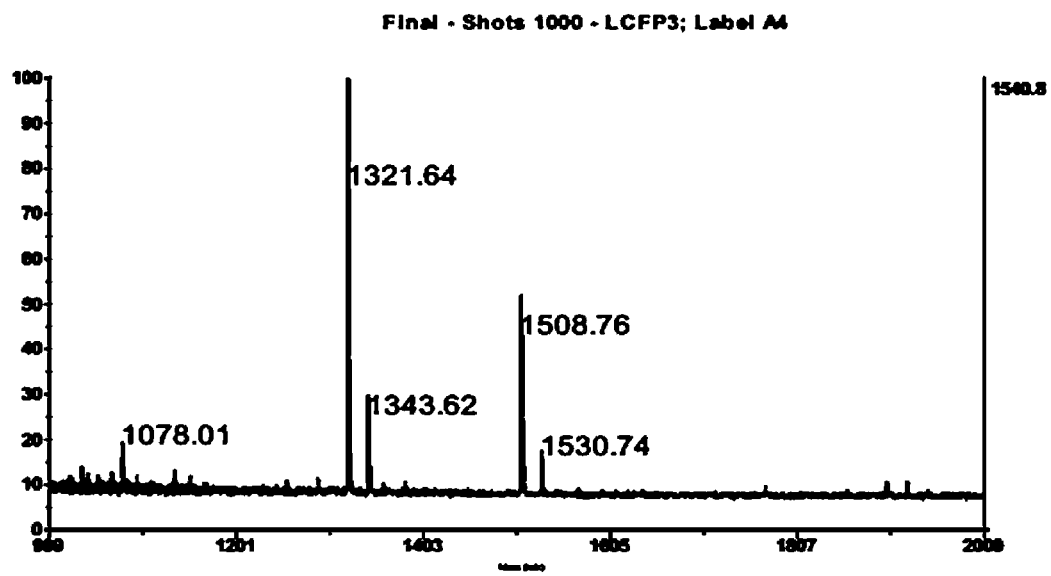
Figure 9:
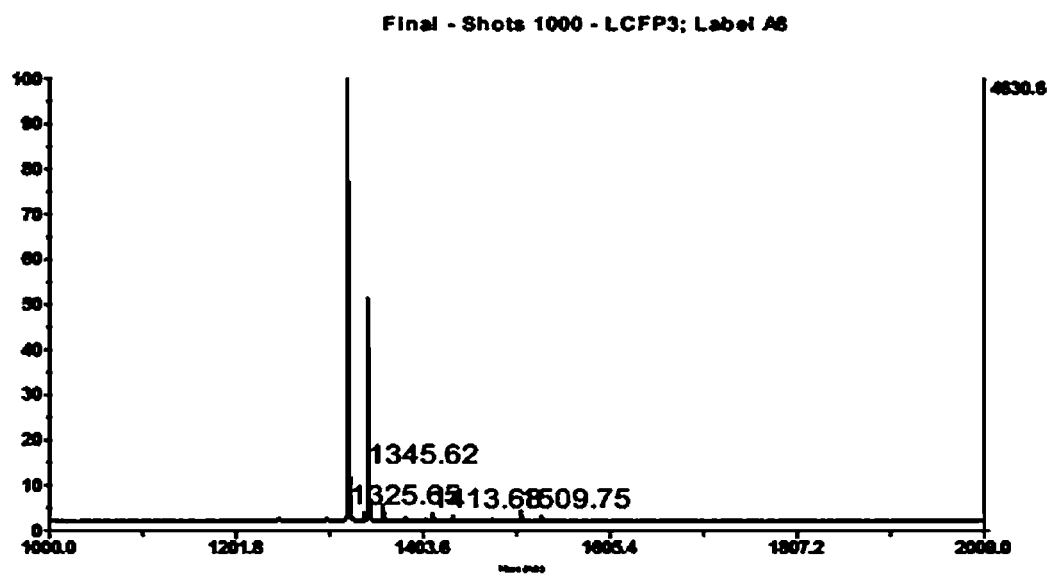
Figure 9:
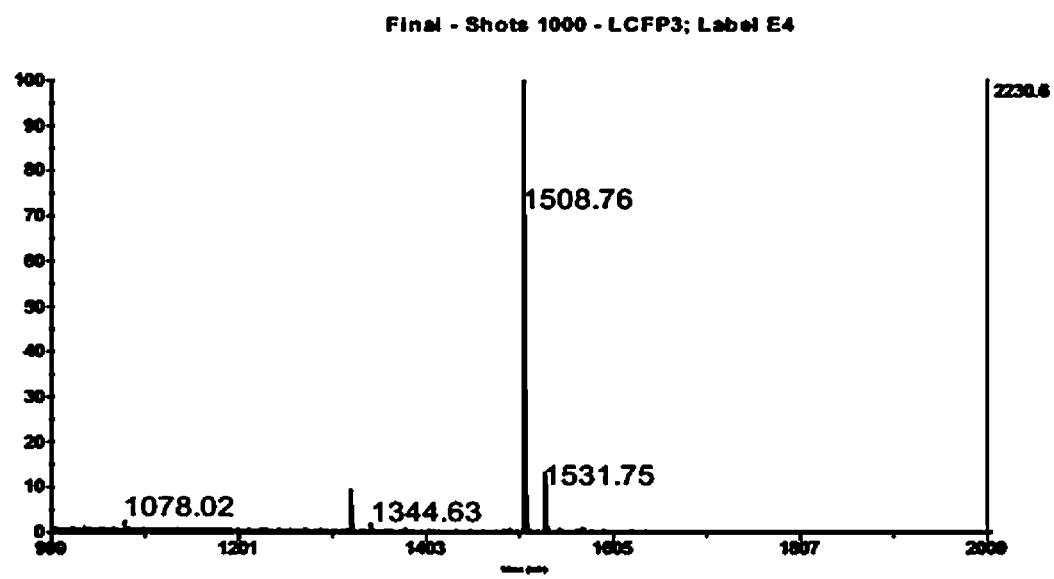
Figure 9:
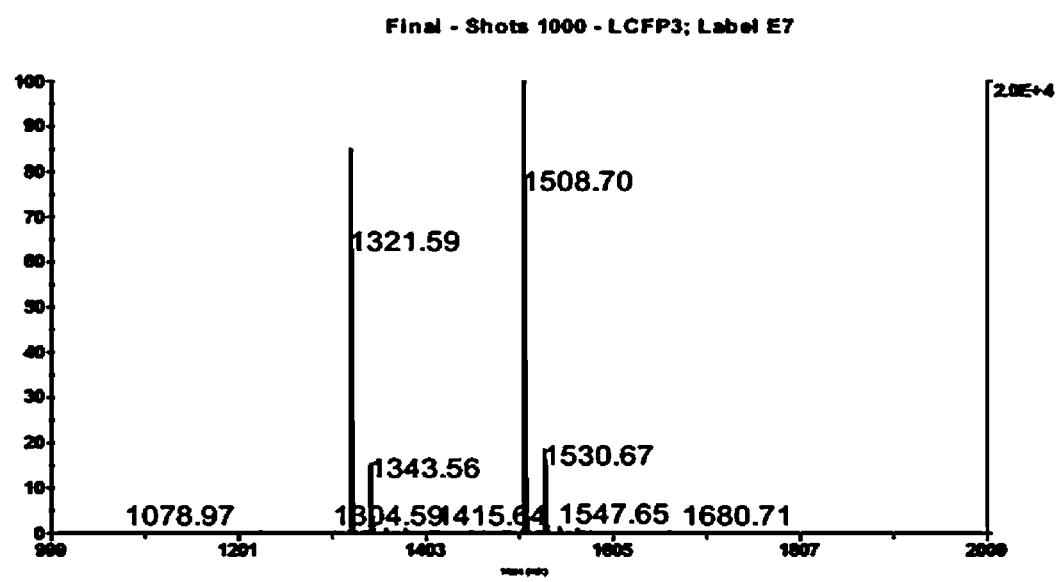
Figure 9:
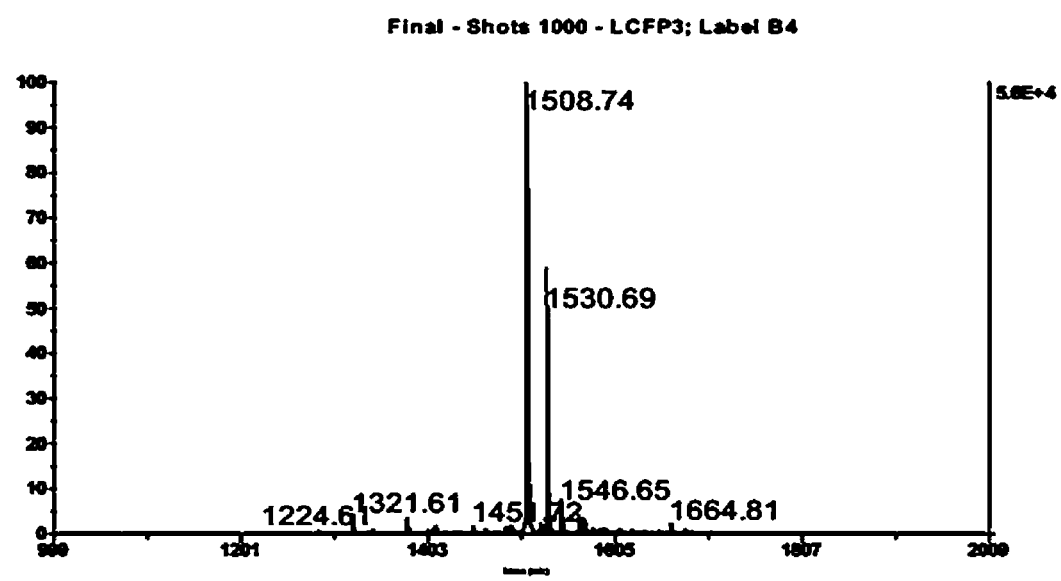
Figure 9:
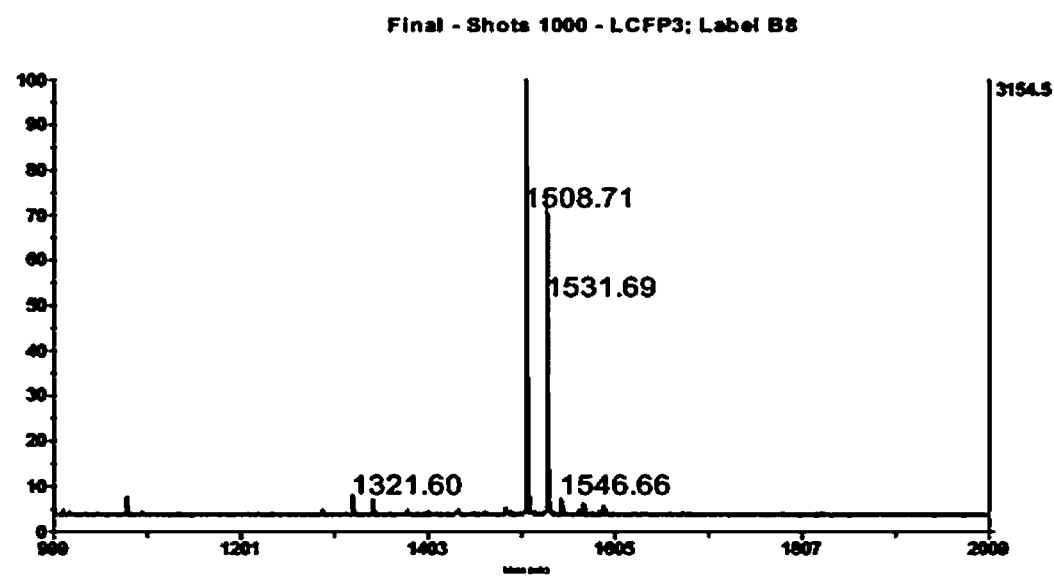
Figure 9:
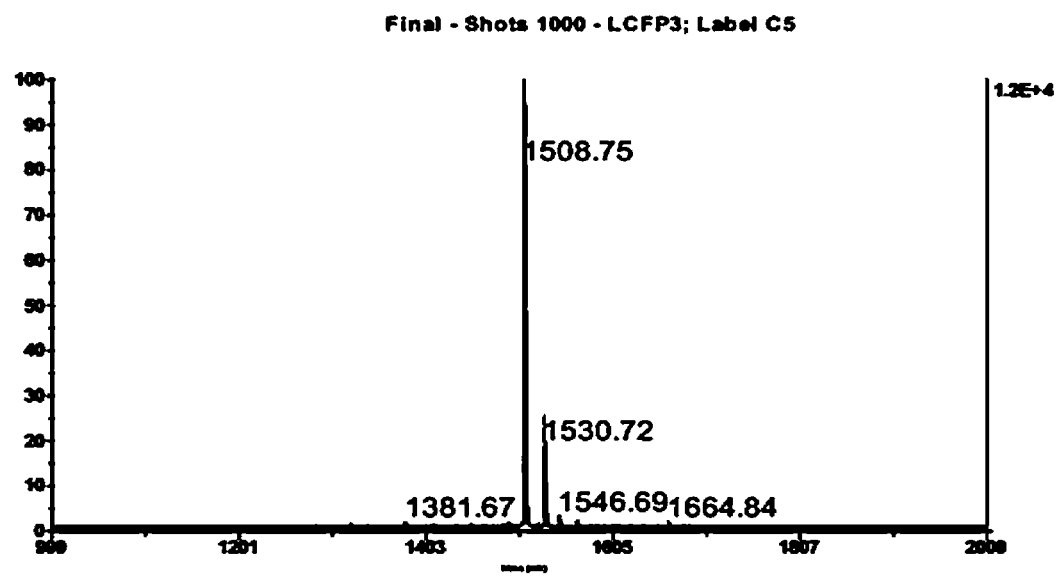
Figure 9:
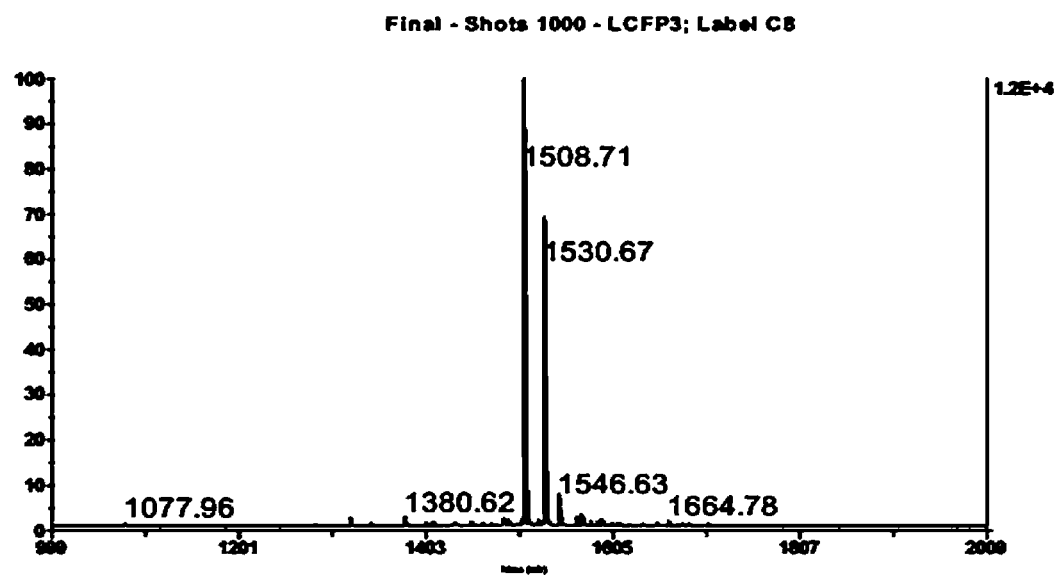
Figure 9:
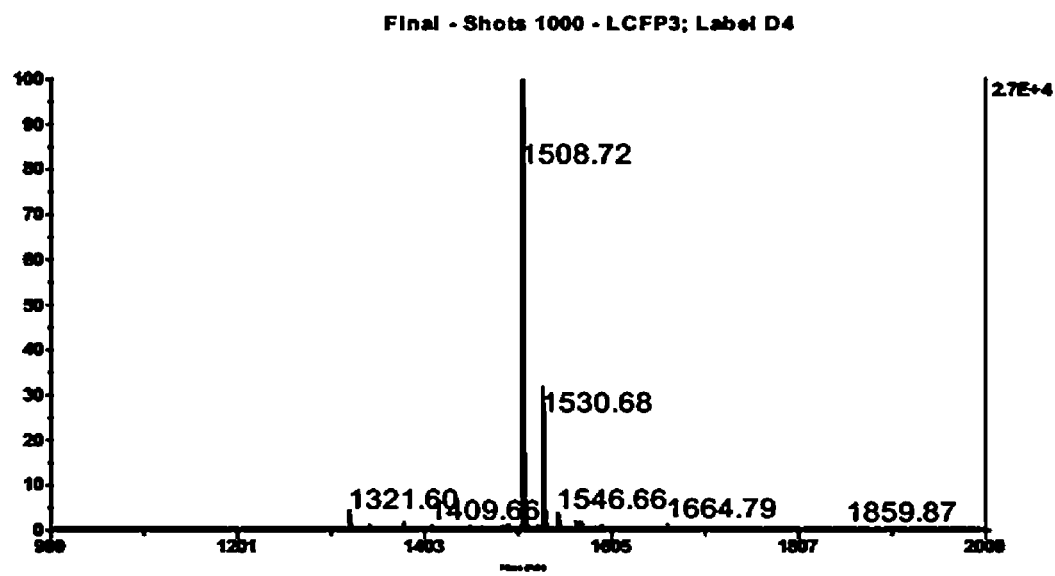
Figure 9:
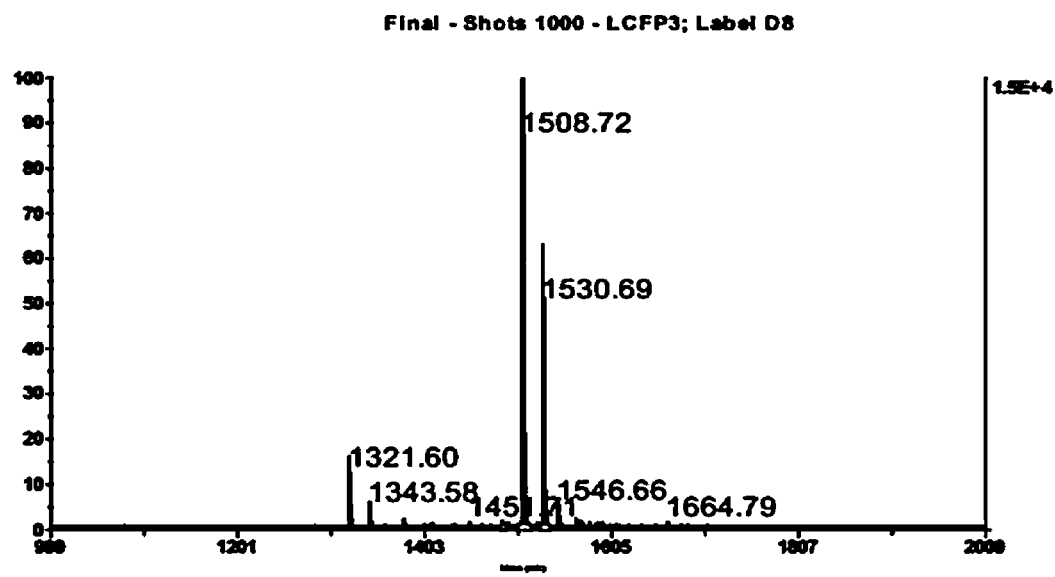
Figure 9:
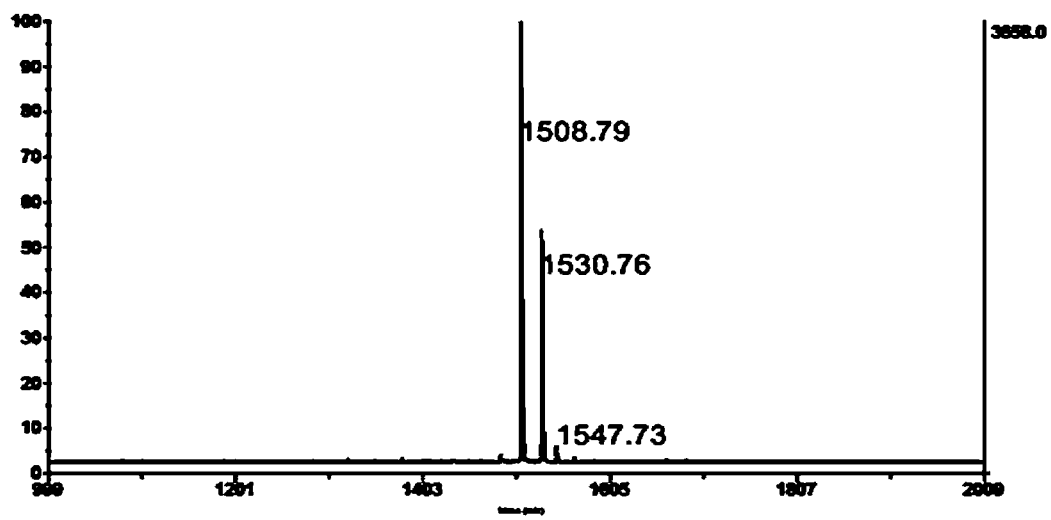
Figure 9:
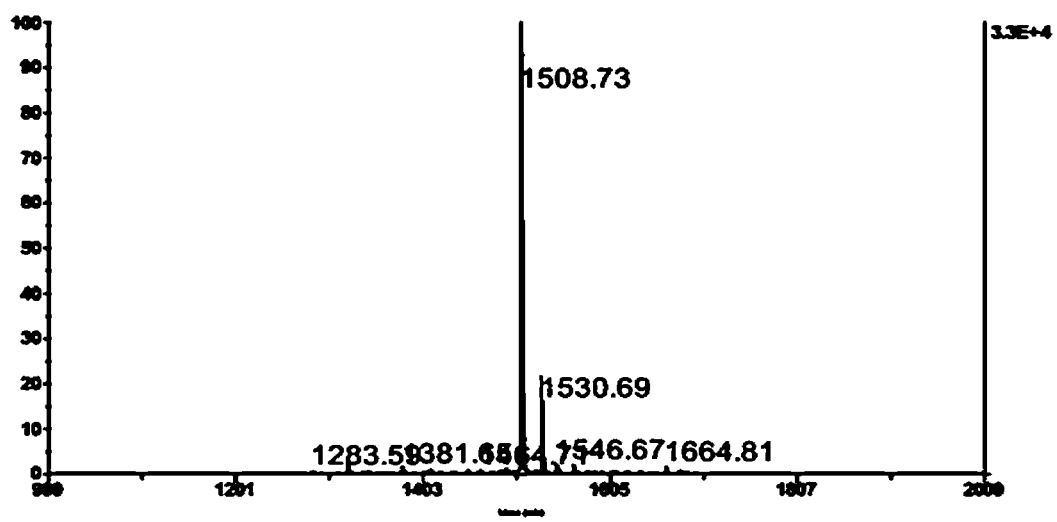
Figure 9:
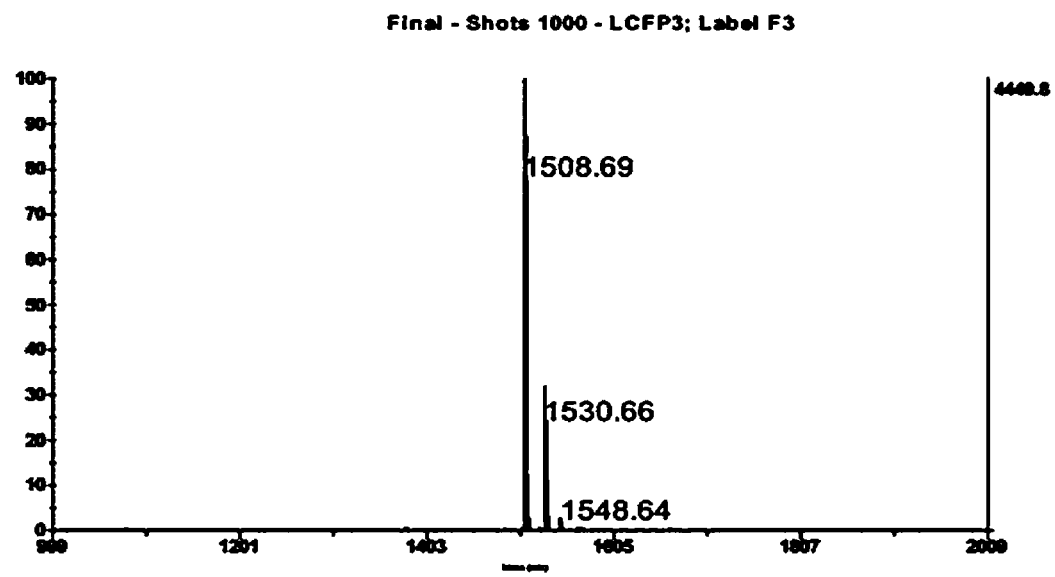
Figure 9:
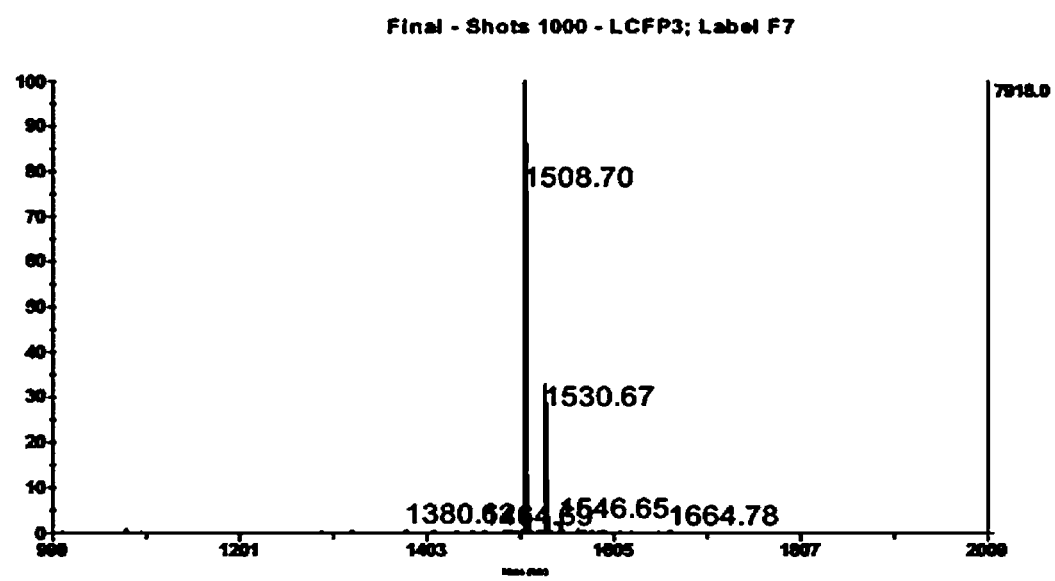

FIG. 9 shows the raw mass-spectrometry results of Gate-Keeper mutants.

Figure 10:
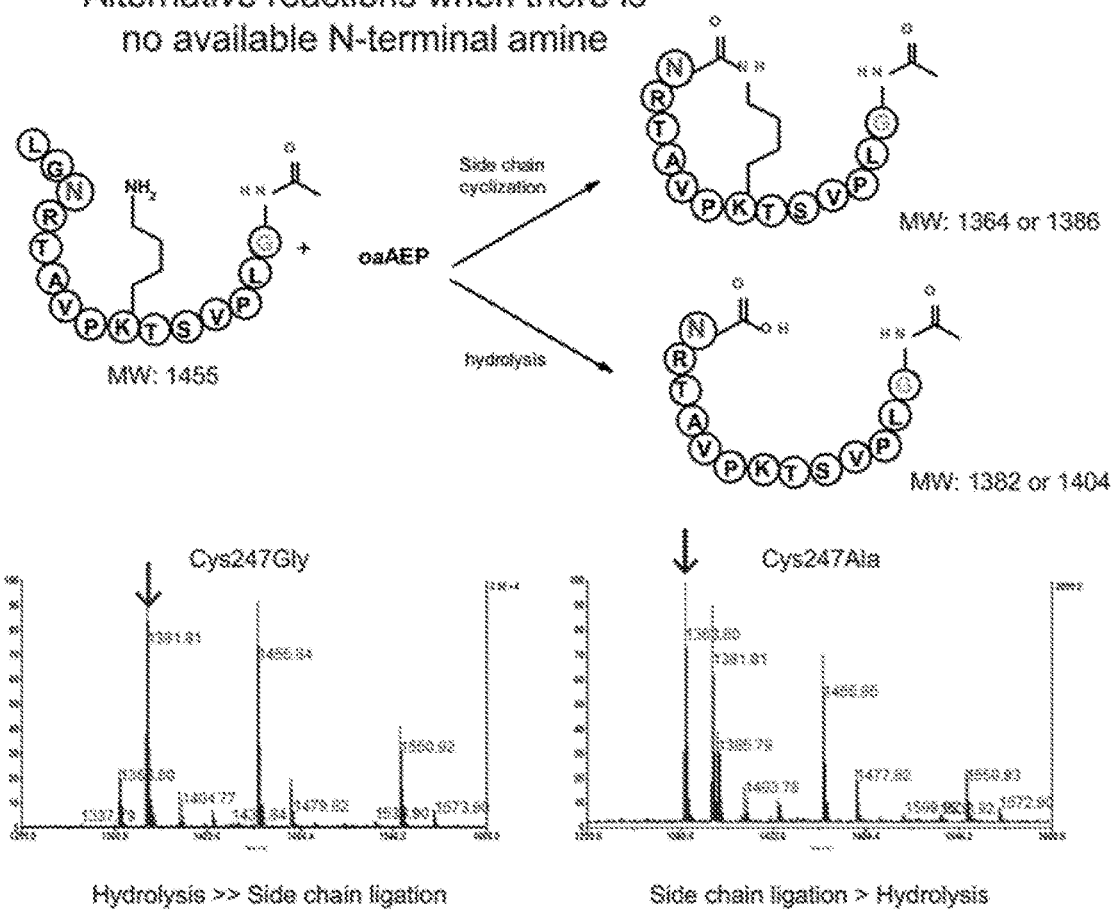

FIG. 10 shows the potential side product of the ligation reaction. If there is no available N-terminal amine, side chain ligation and proteolysis could happen in Cys247Gly and Cys247Ala mutants. The smaller size of the side chain of Cys247Gly mutant permitted water molecules to participate in the reaction and results proteolysis.

Figure 11:
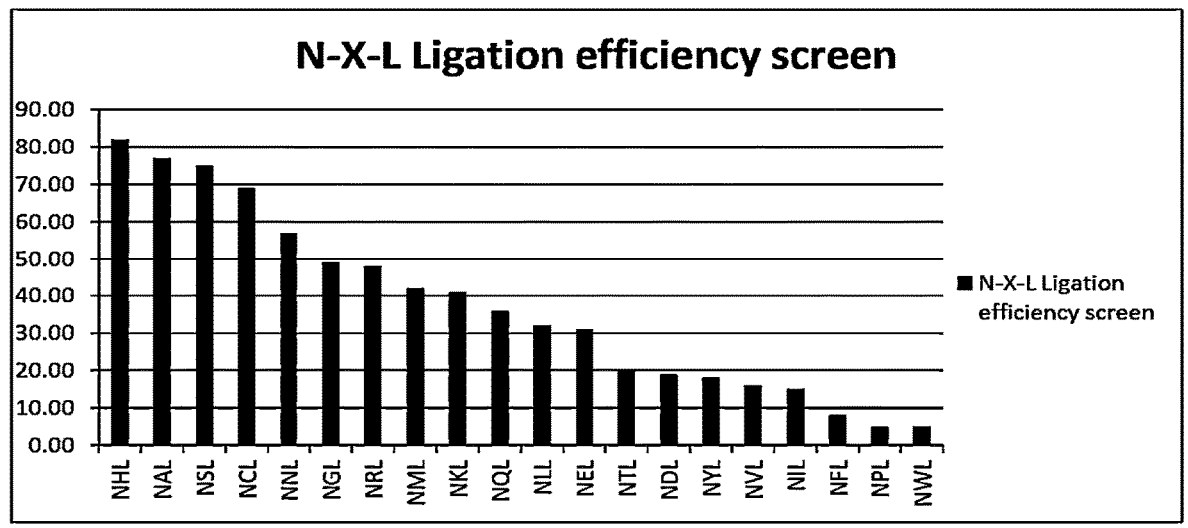
Figure 11:
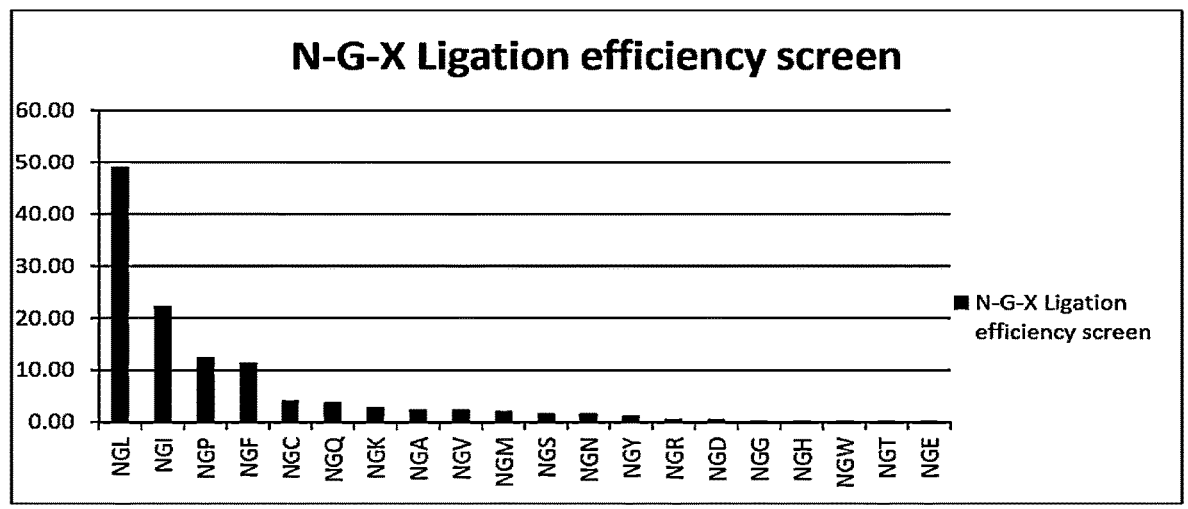
Figure 11:
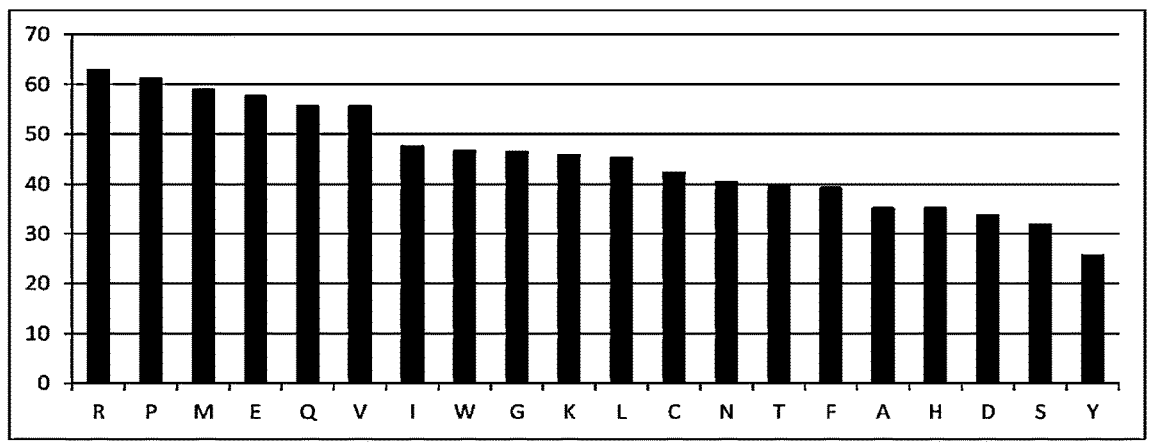
Figure 11:
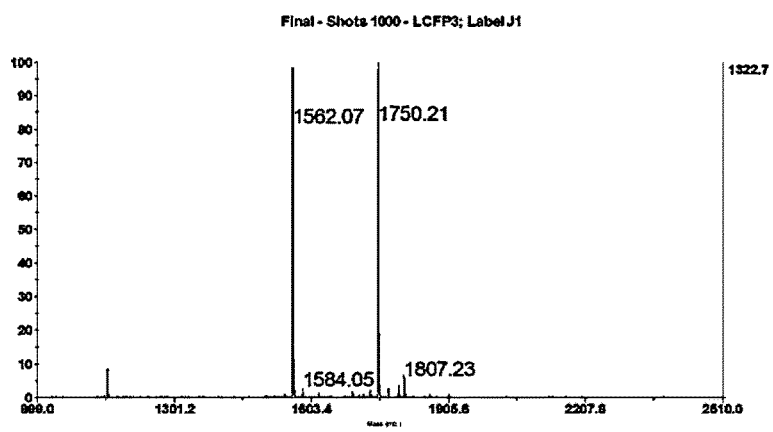
Figure 11D:
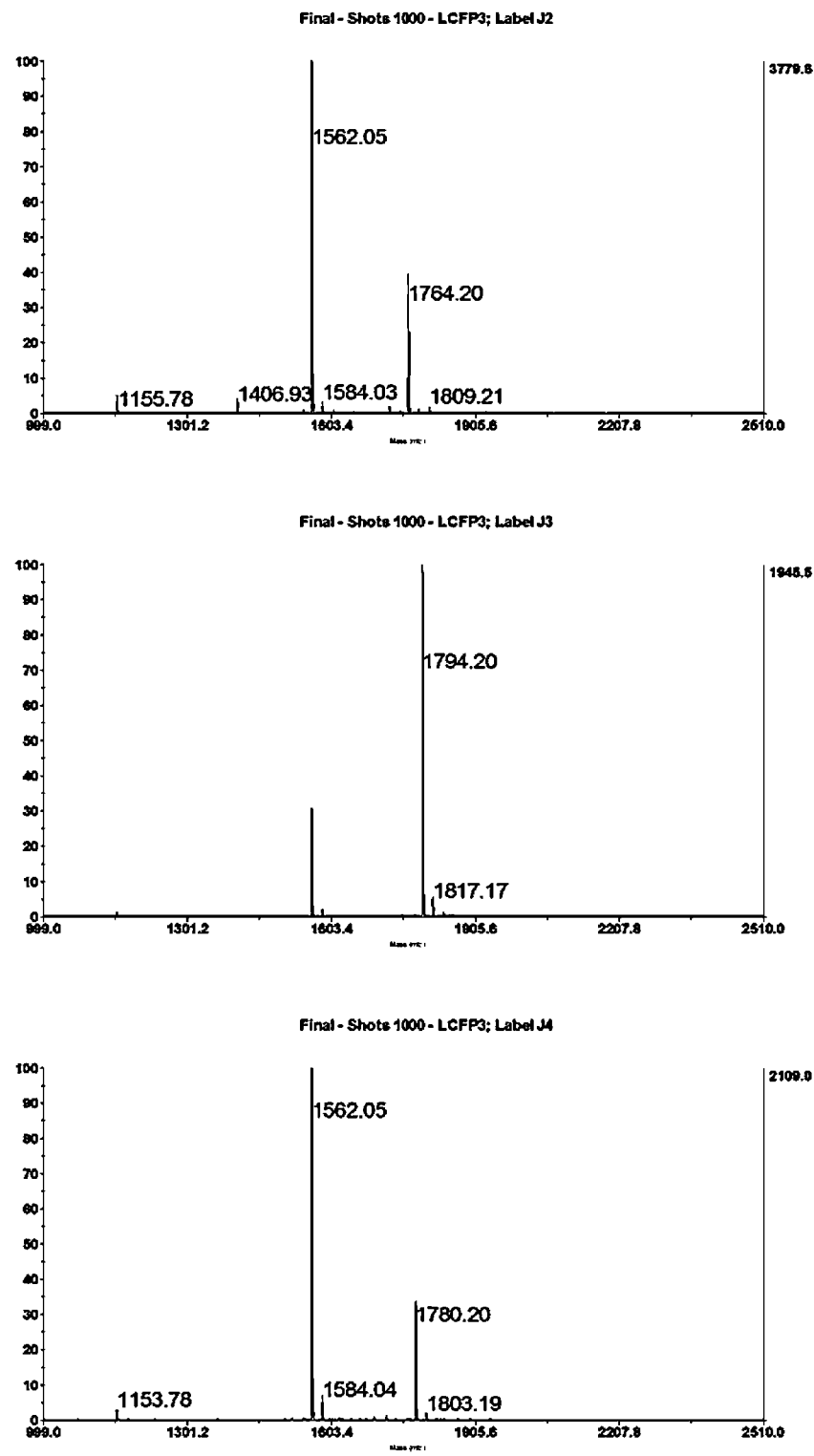
Figure 11D:
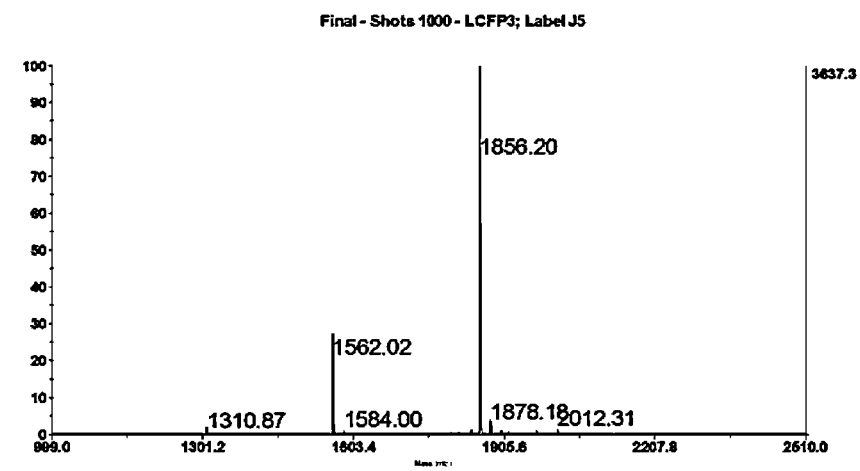
Figure 11D:
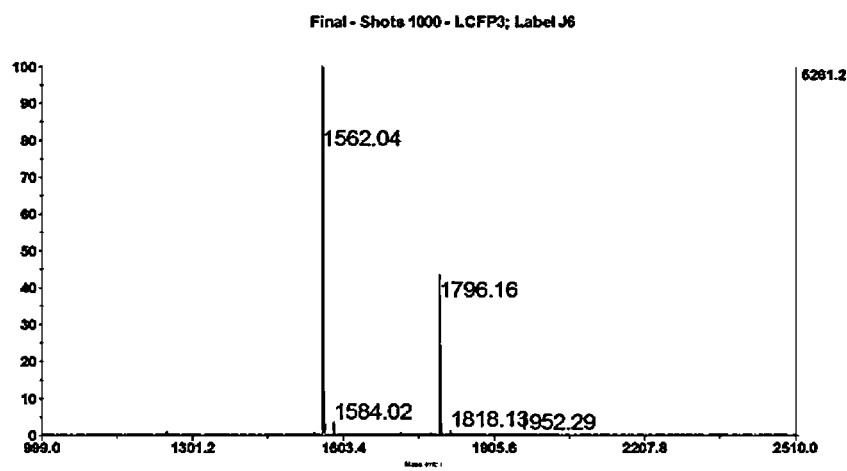
Figure 11D:
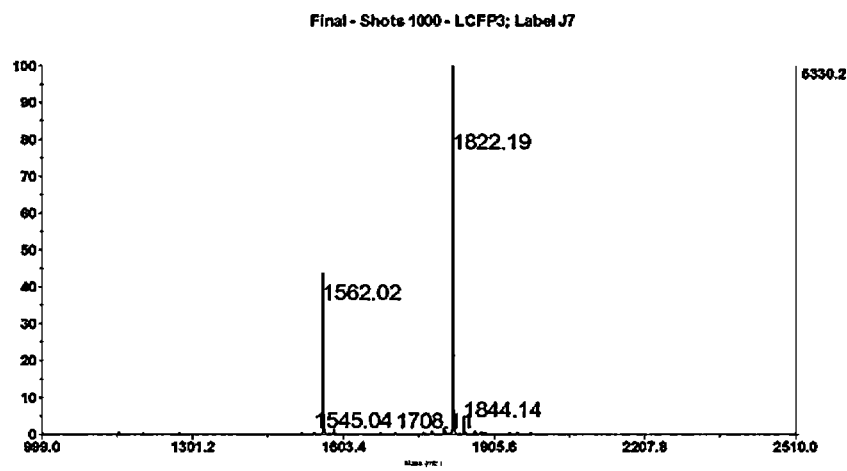
Figure 11D:
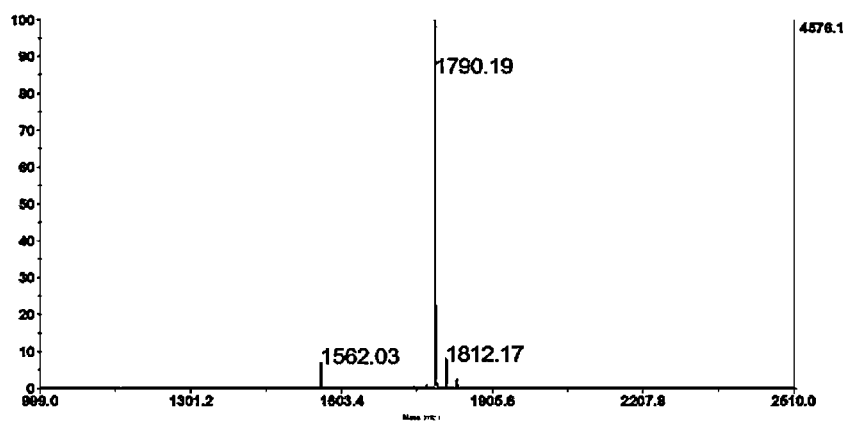
Figure 11D:
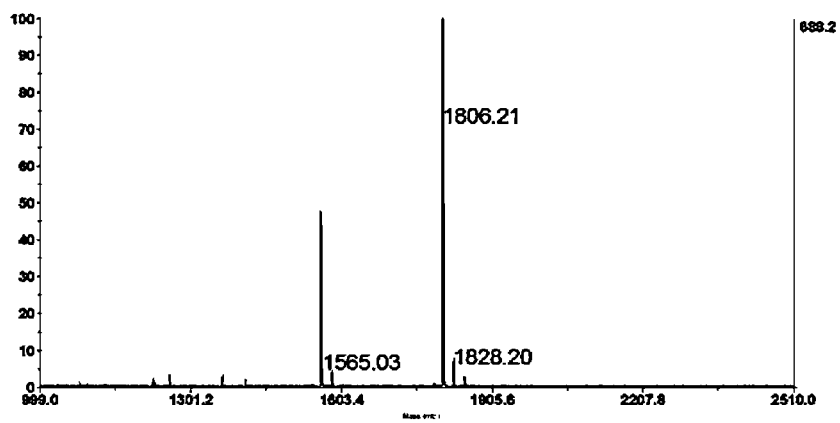
Figure 11D:
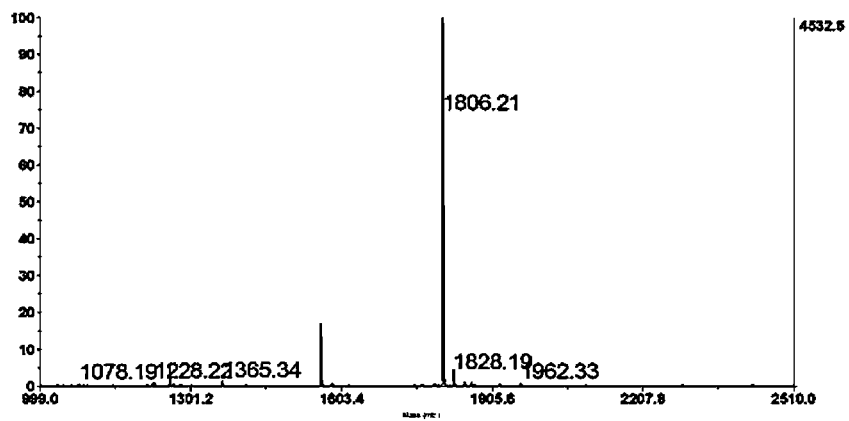
Figure 11D:
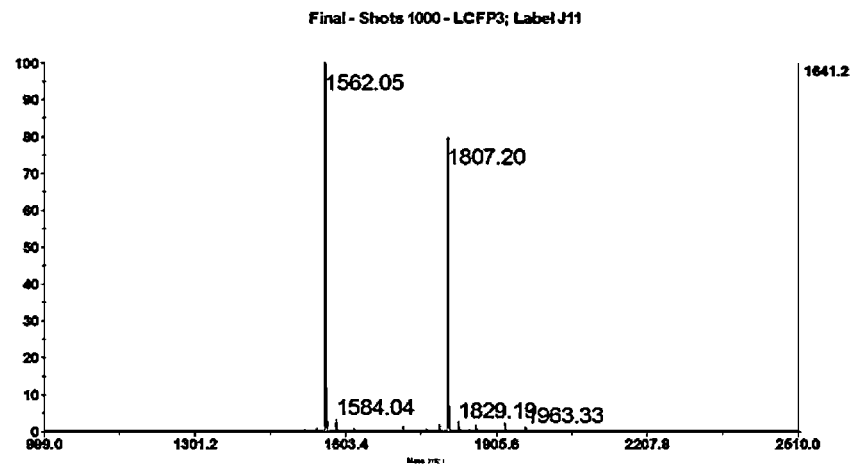
Figure 11D:
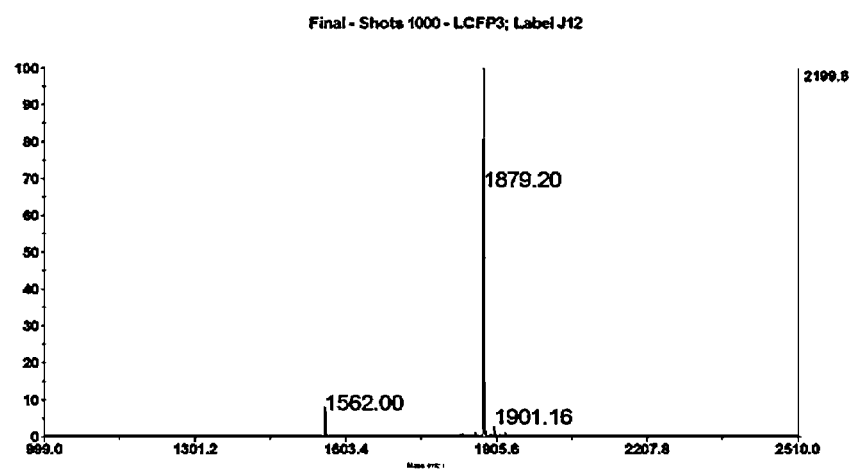
Figure 11D:
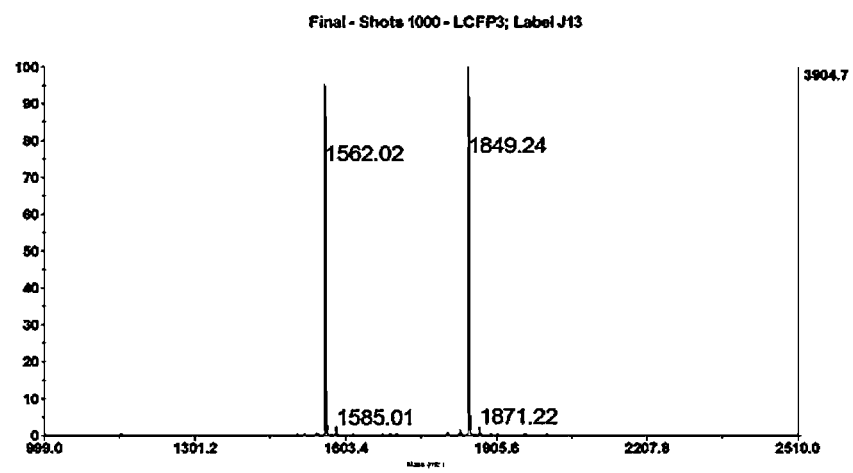
Figure 11D:
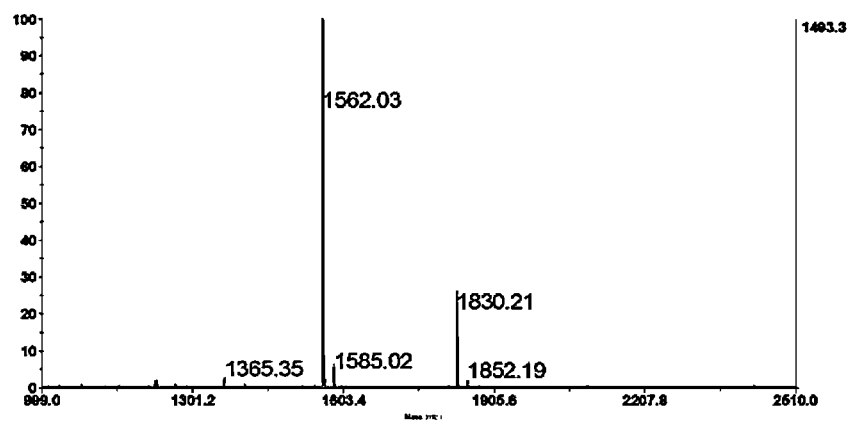
Figure 11D:
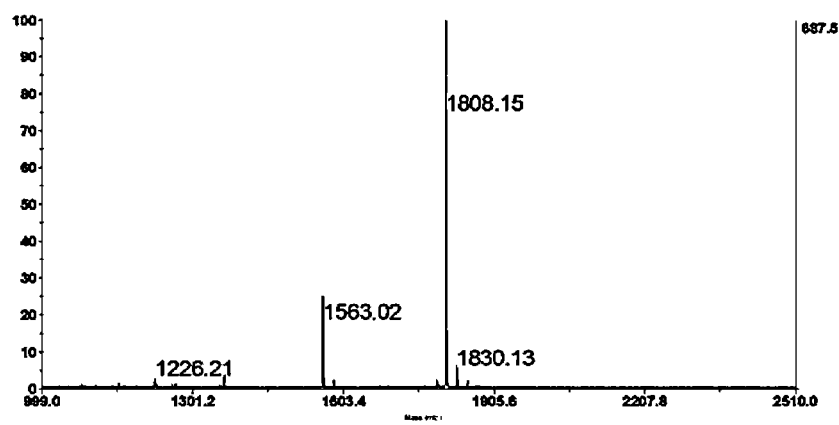
Figure 11D:
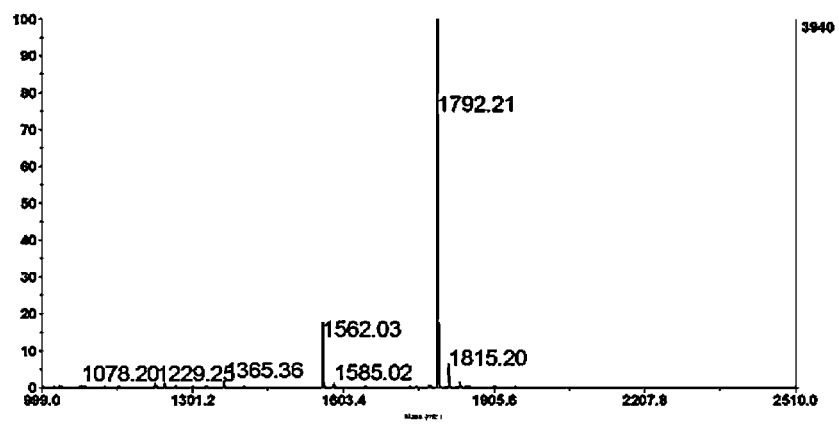
Figure 11D:
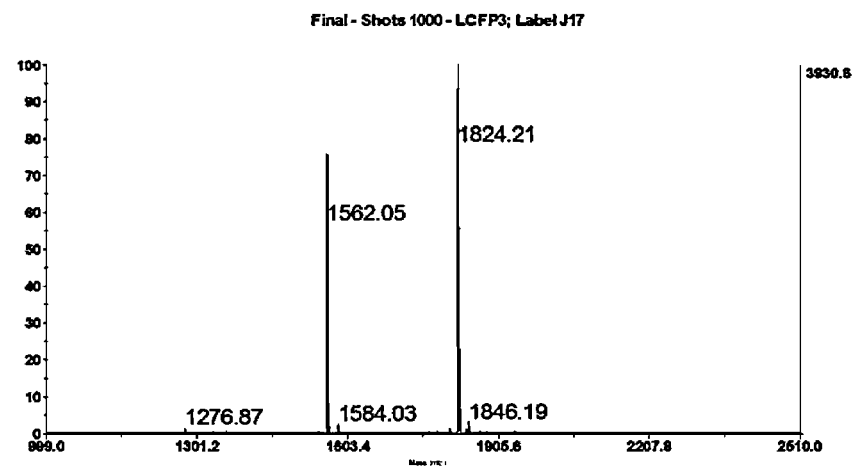
Figure 11D:
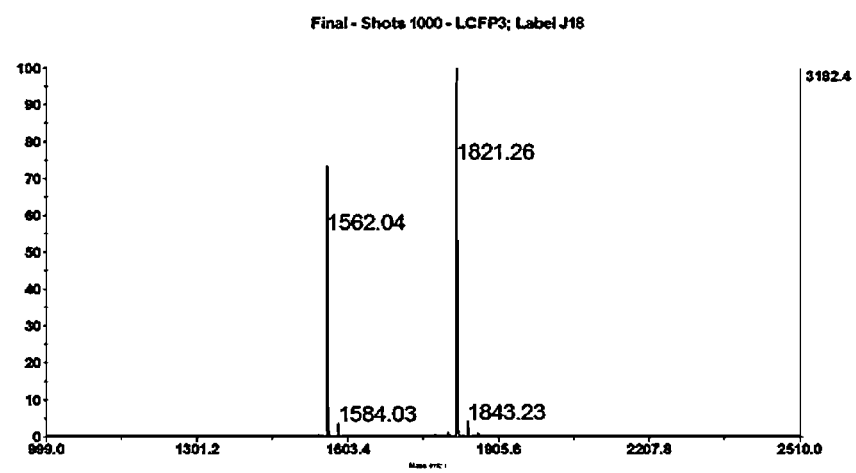
Figure 11D:
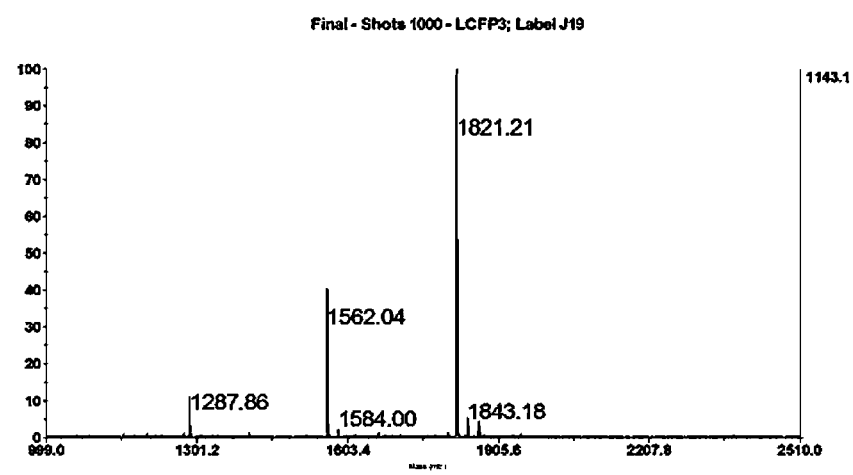
Figure 11D:
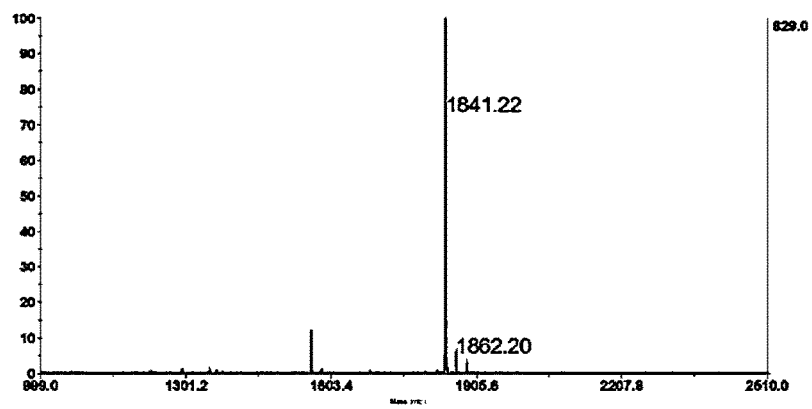
Figure 11D:
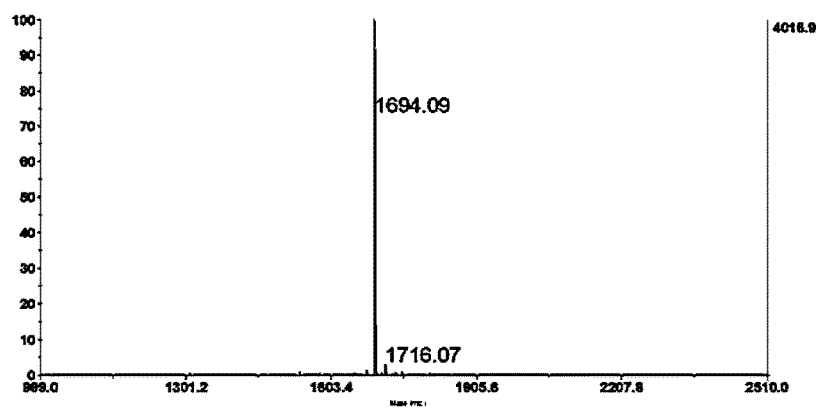
Figure 11D:
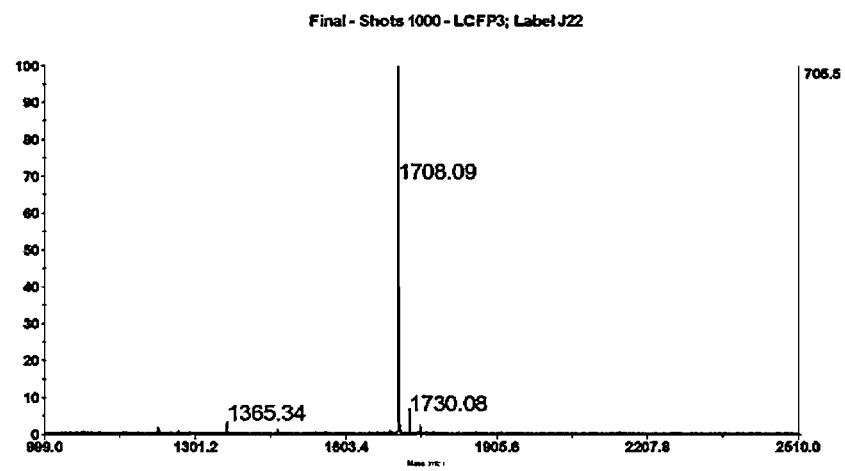
Figure 11D:
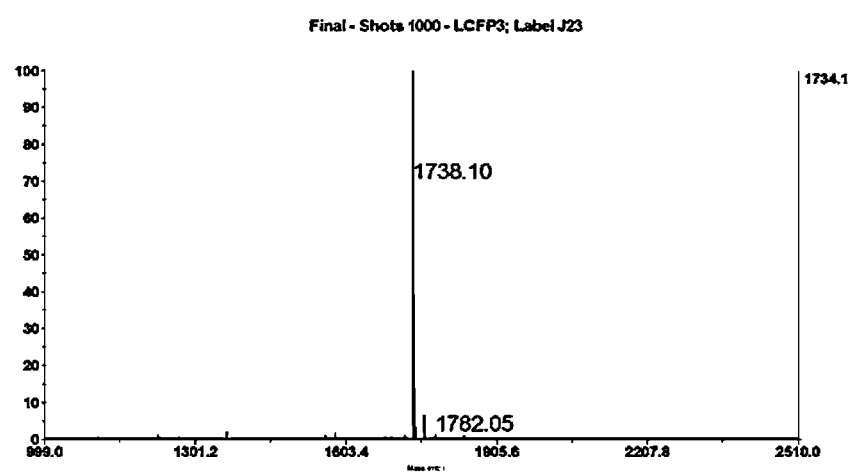
Figure 11D:
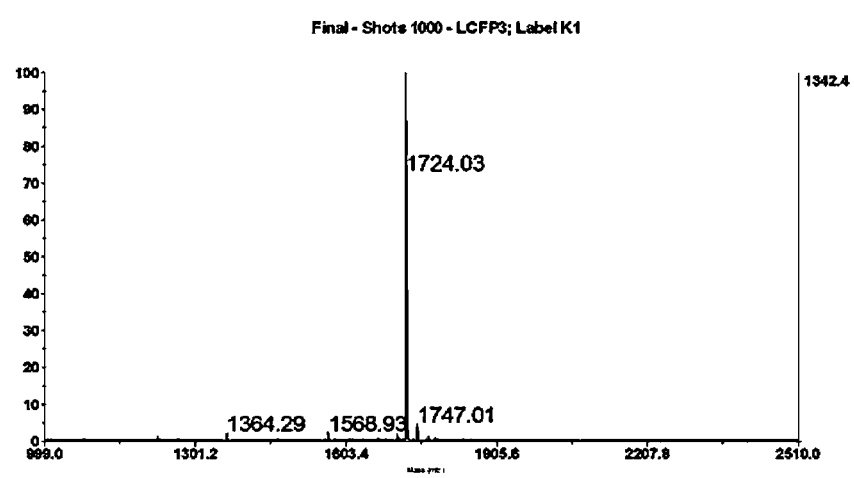
Figure 11D:
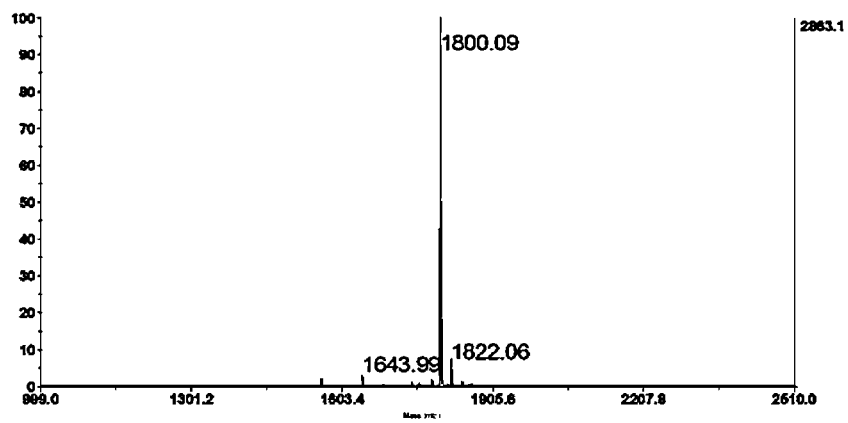
Figure 11D:
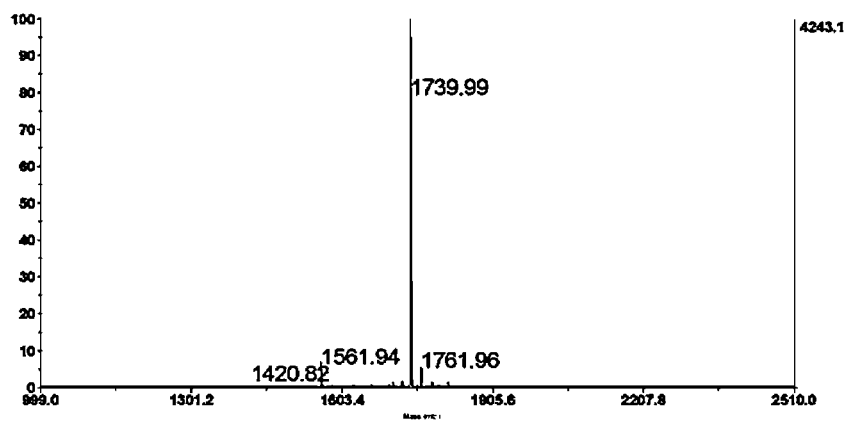
Figure 11D:
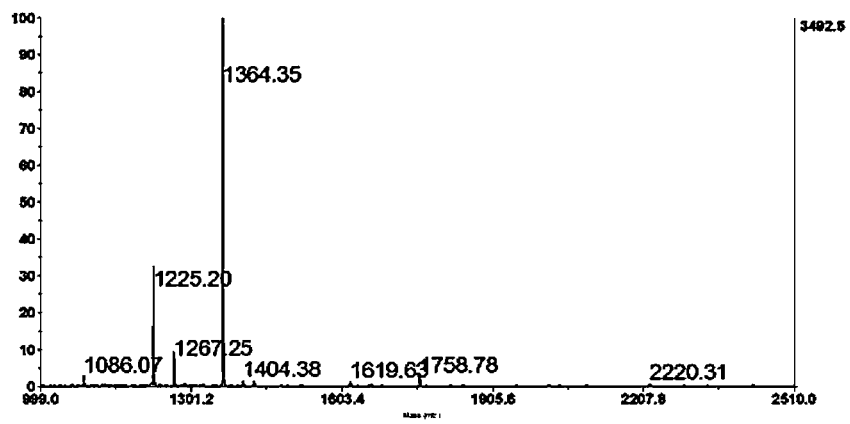
Figure 11D:
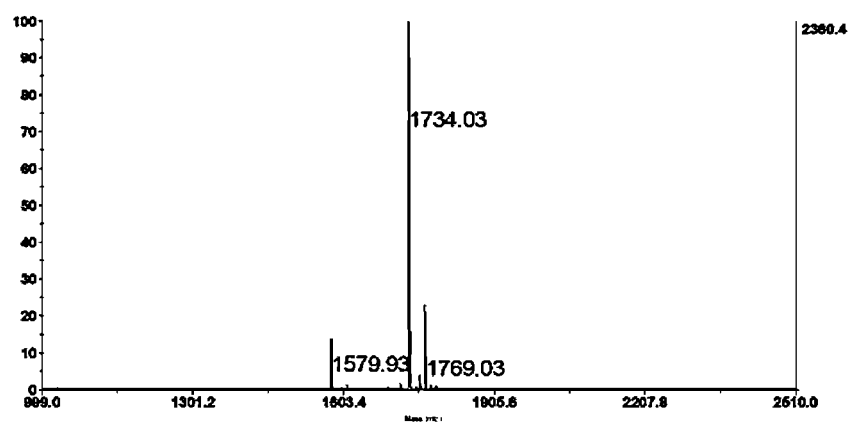
Figure 11D:
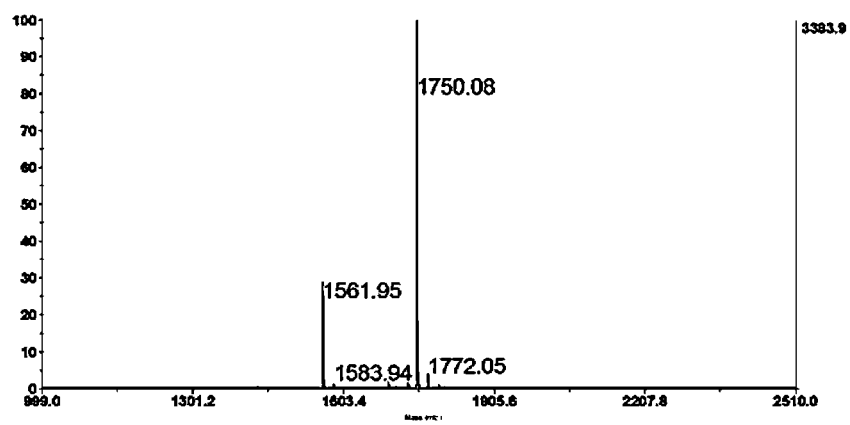
Figure 11D:
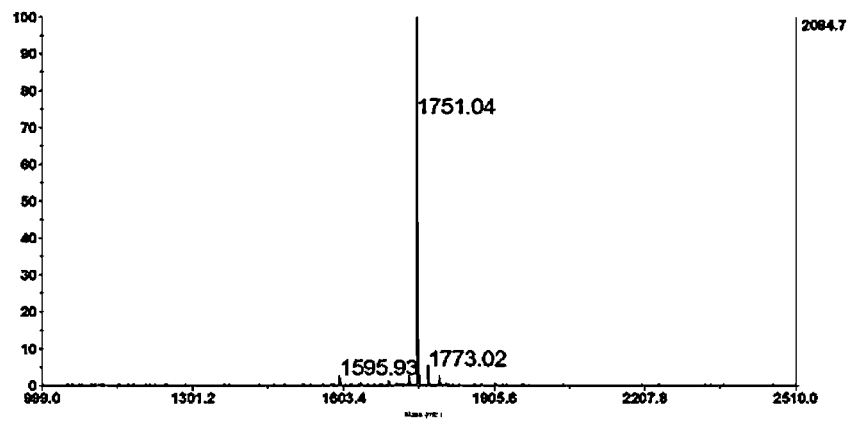
Figure 11D:
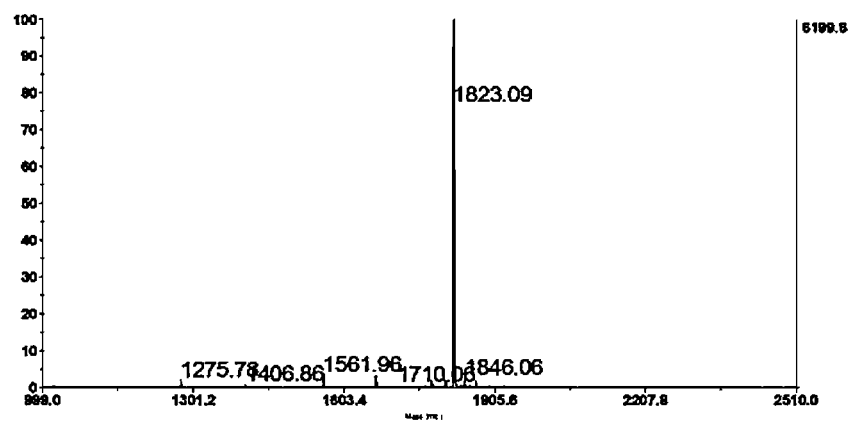
Figure 11D:
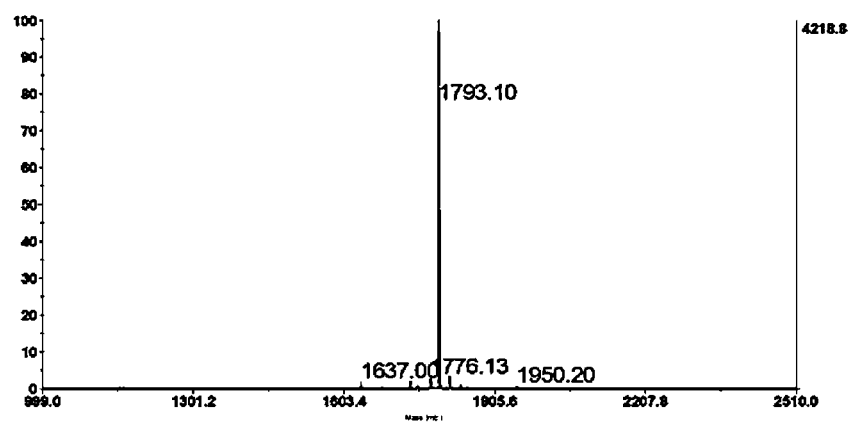
Figure 11D:
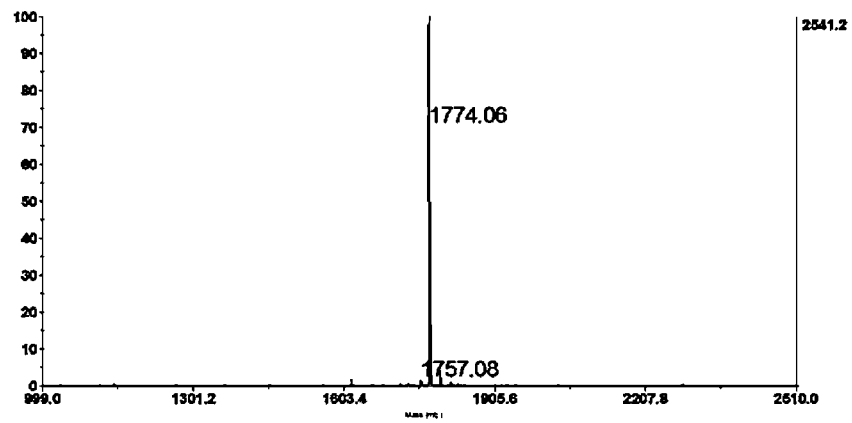
Figure 11D:
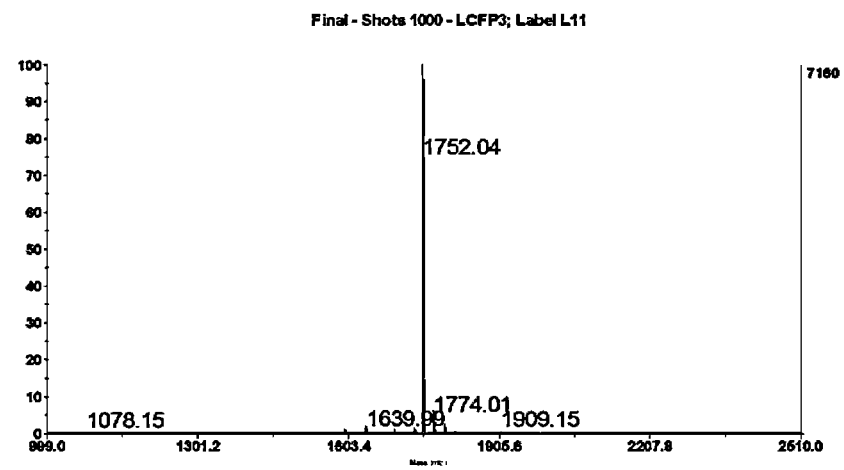
Figure 11D:
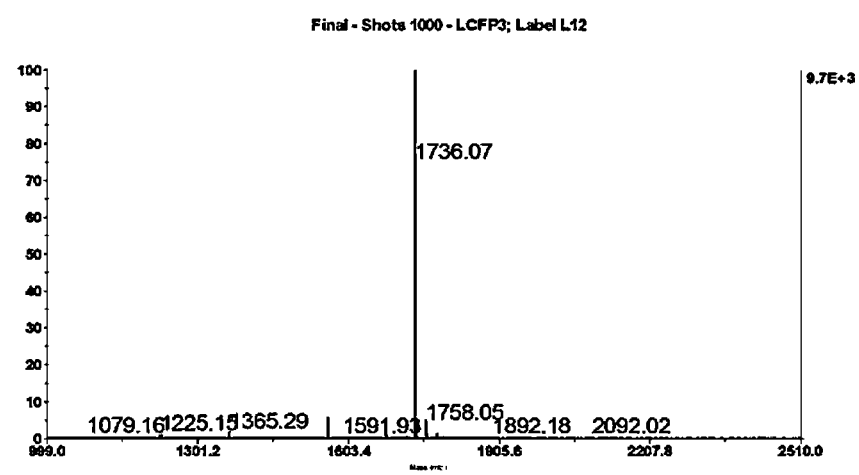
Figure 11D:
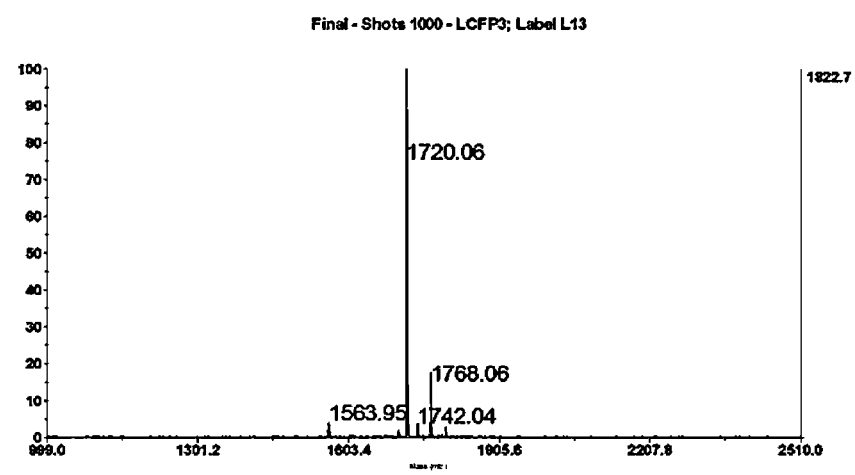
Figure 11D:
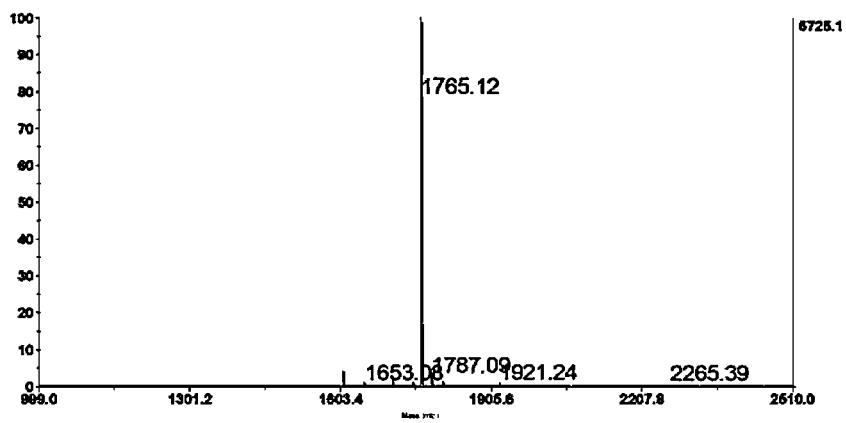
Figure 11D:
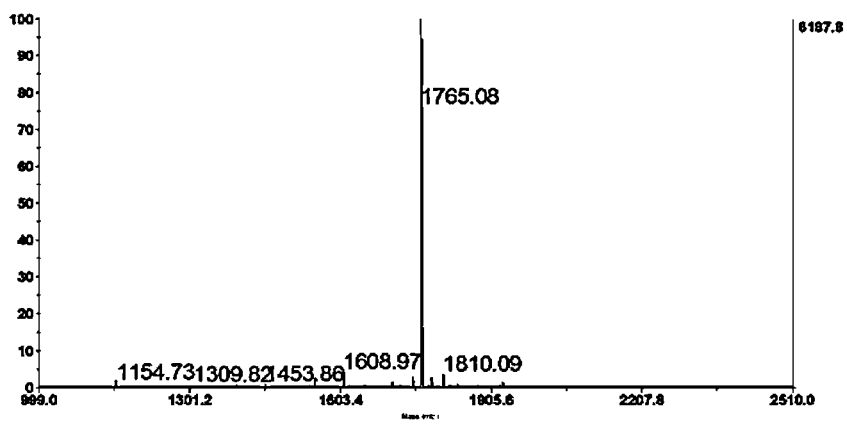
Figure 11D:
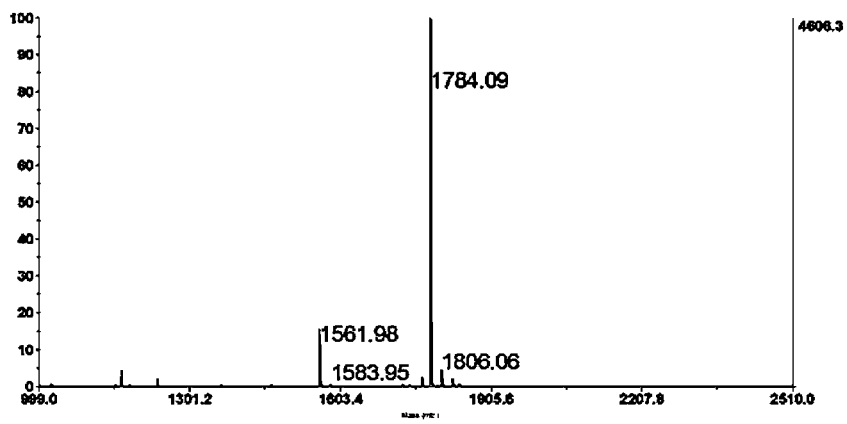
Figure 11D:
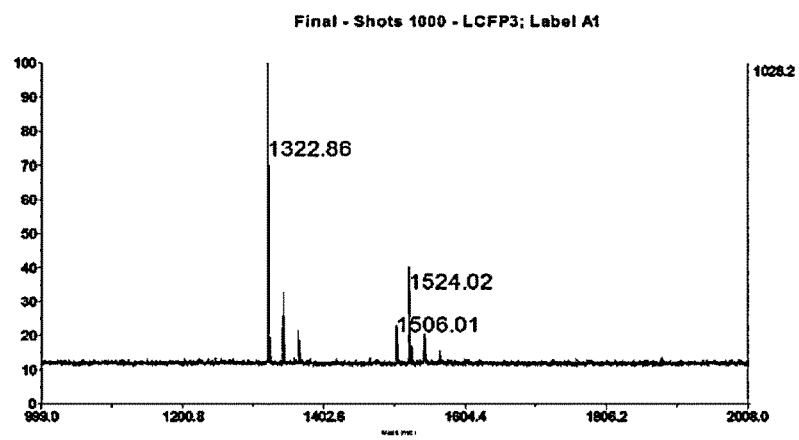
Figure 11D:
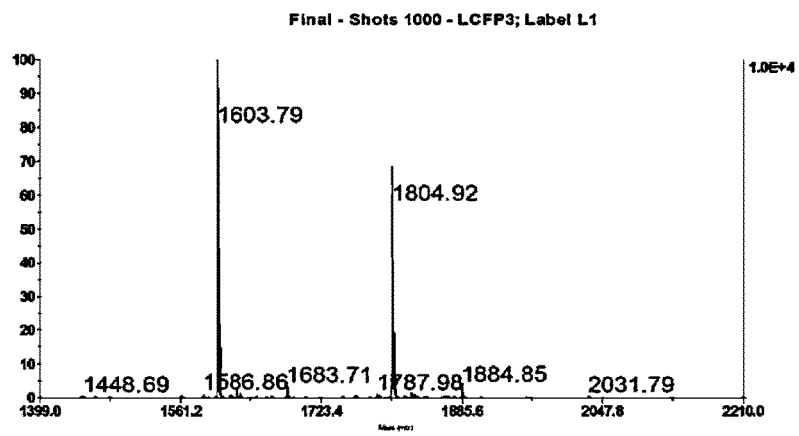
Figure 11D:
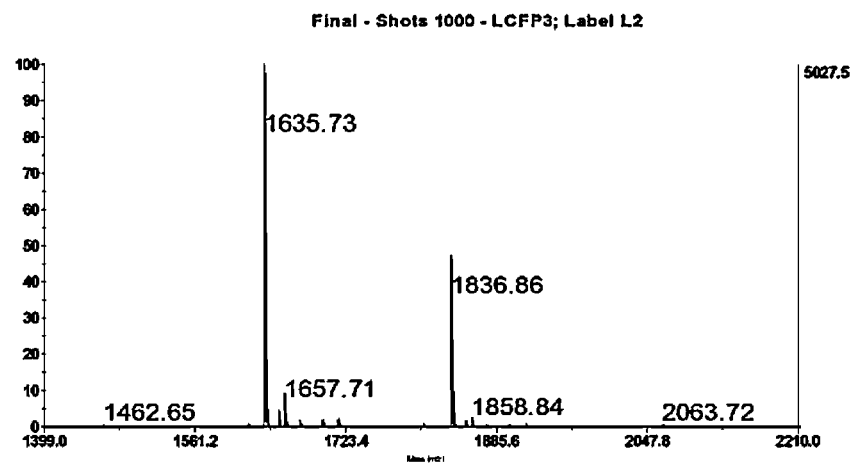
Figure 11D:
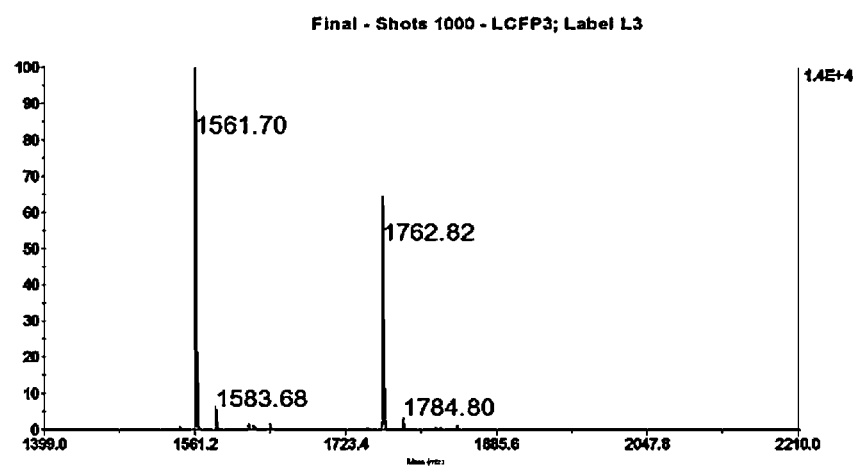
Figure 11D:
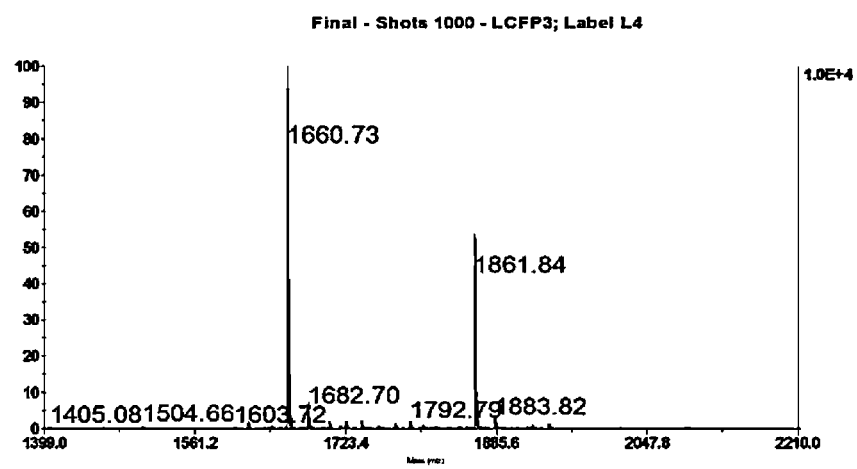
Figure 11D:
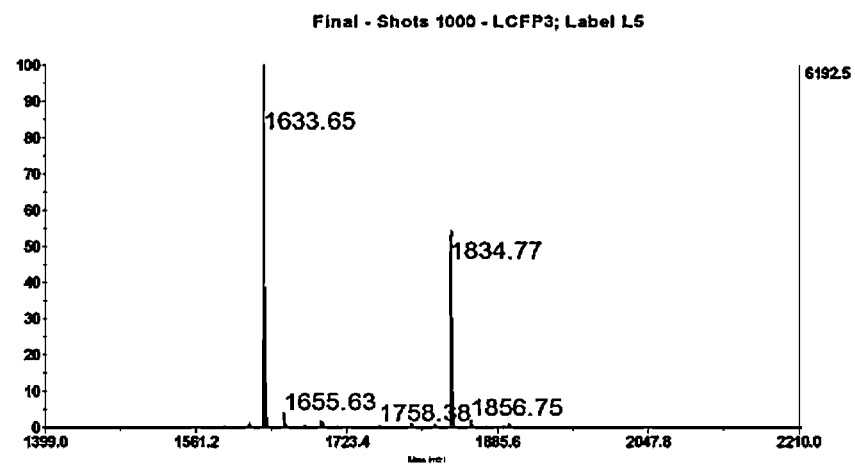
Figure 11D:
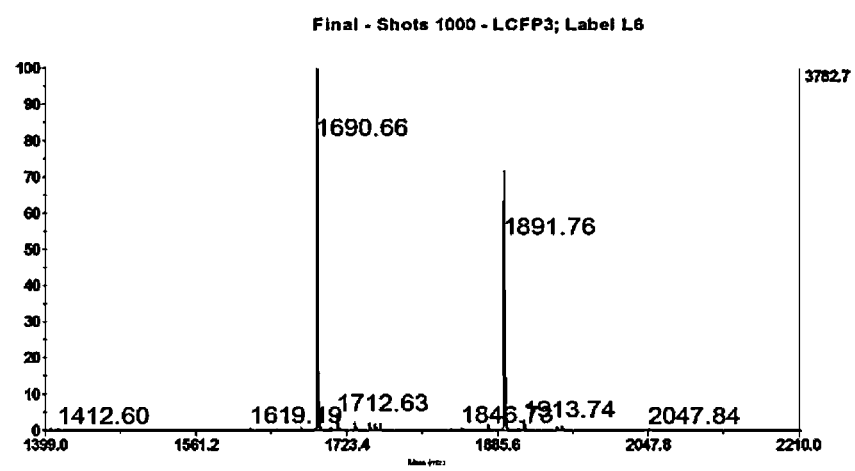
Figure 11D:
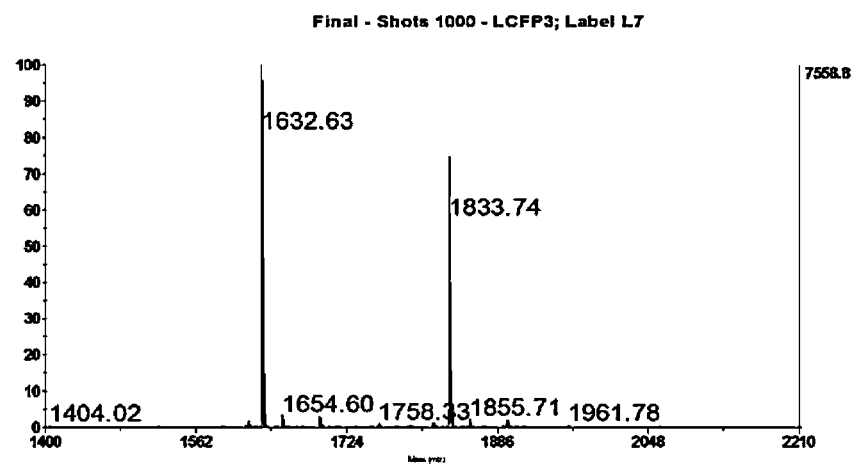
Figure 11D:
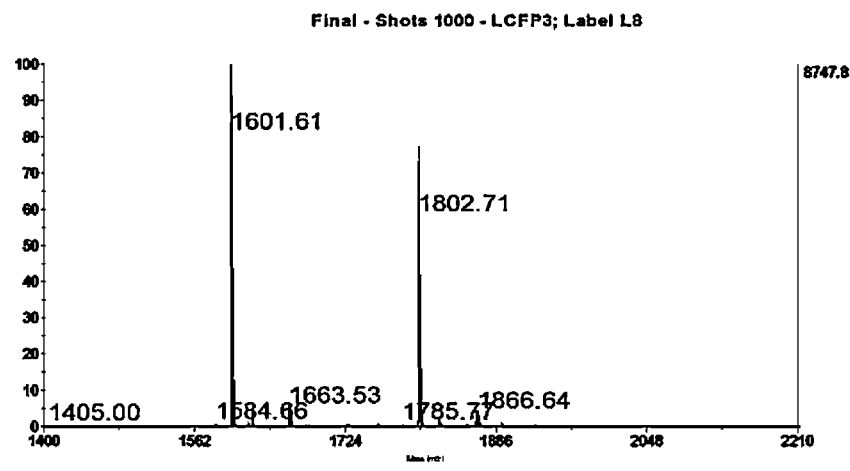
Figure 11D:
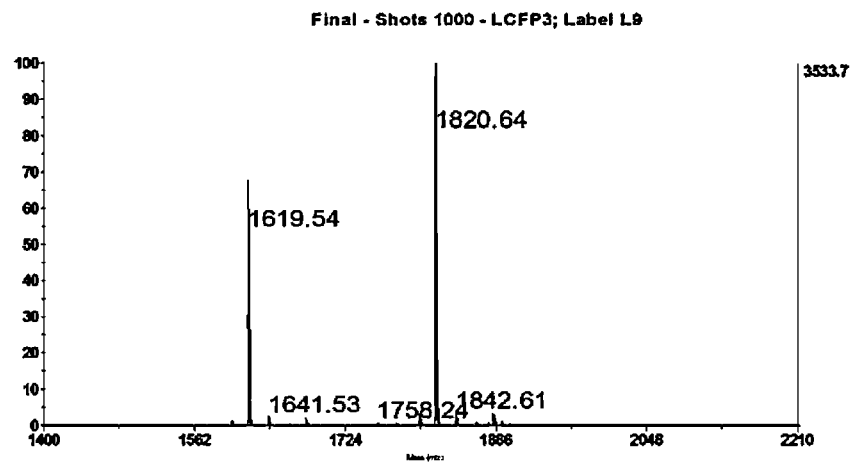
Figure 11D:
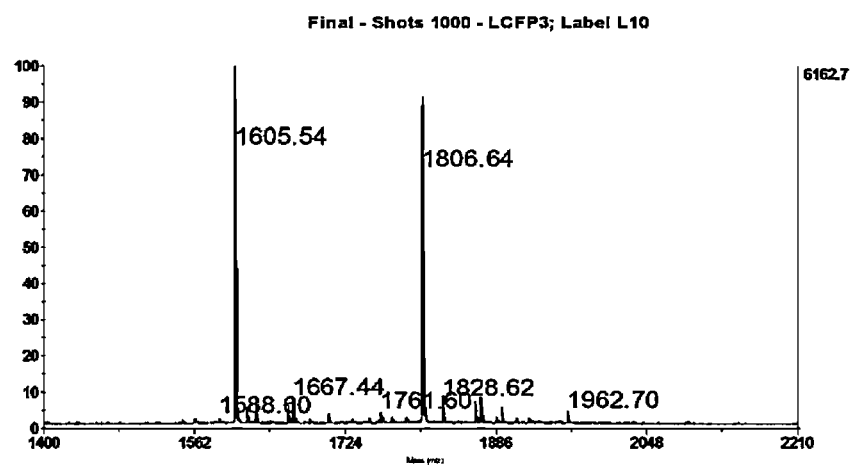
Figure 11D:
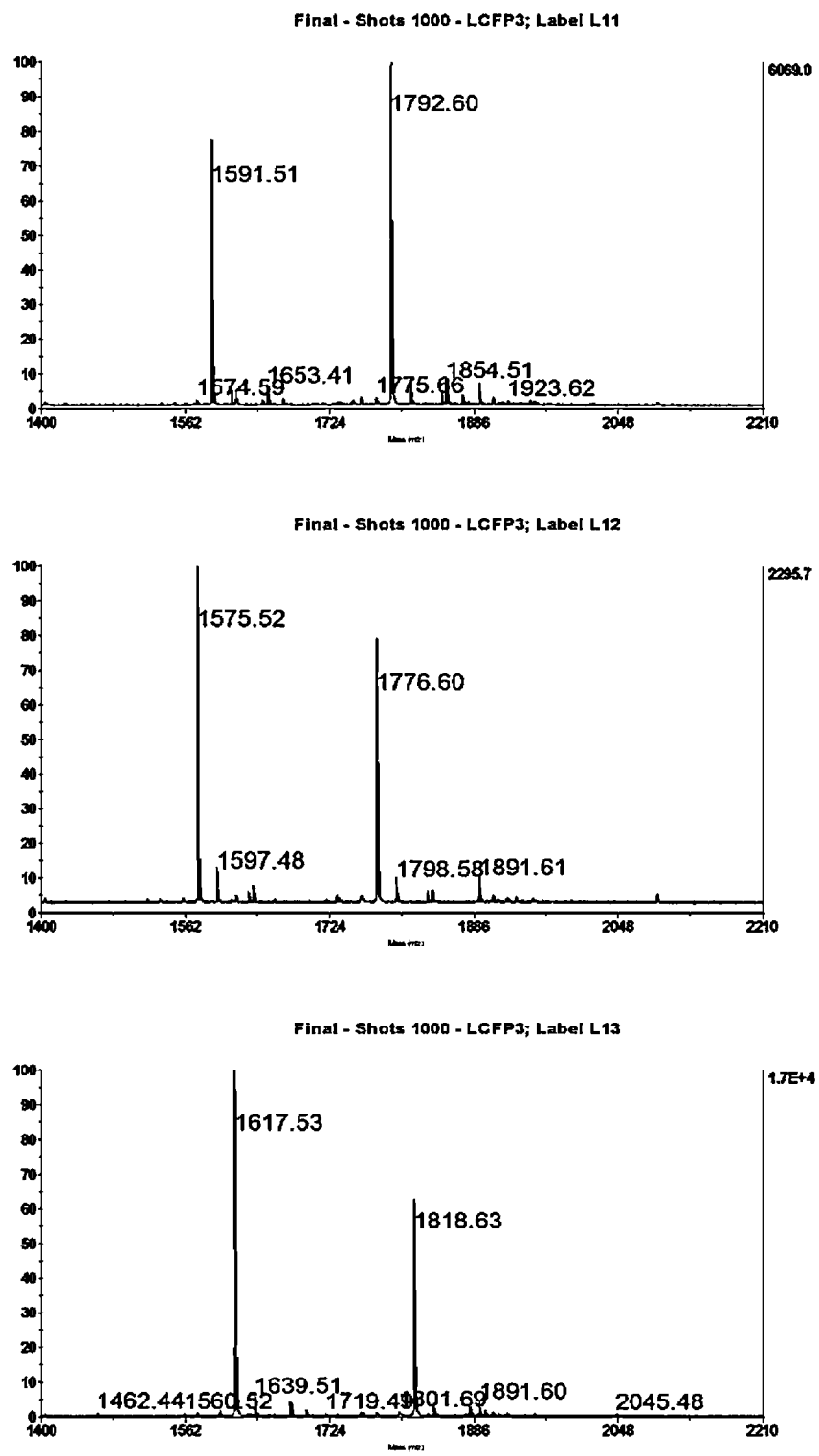
Figure 11D:
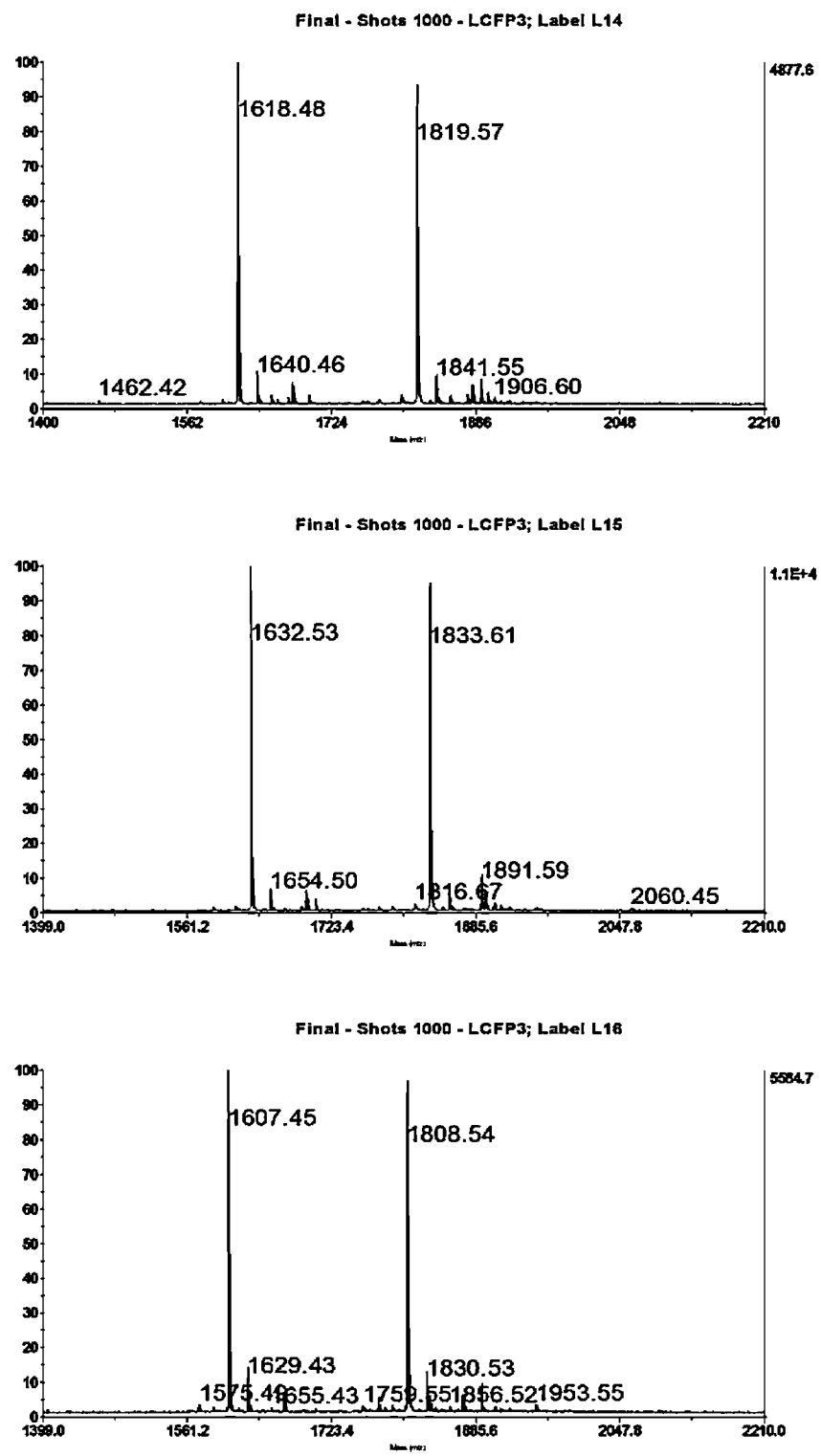
Figure 11D:
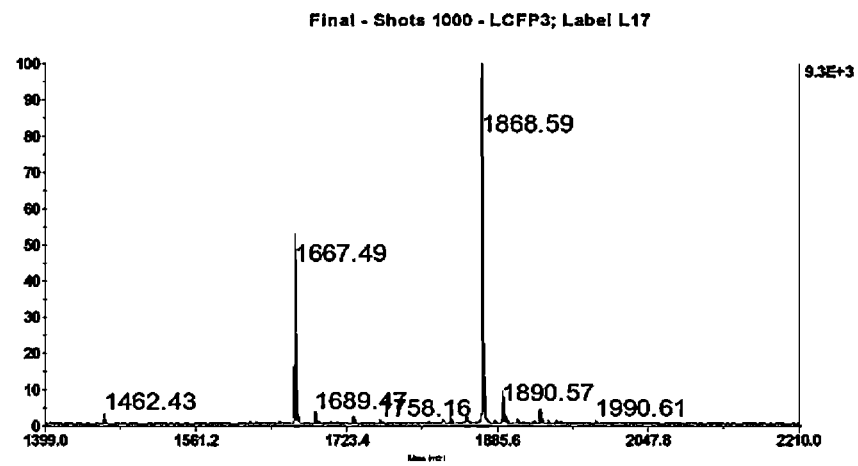
Figure 11D:
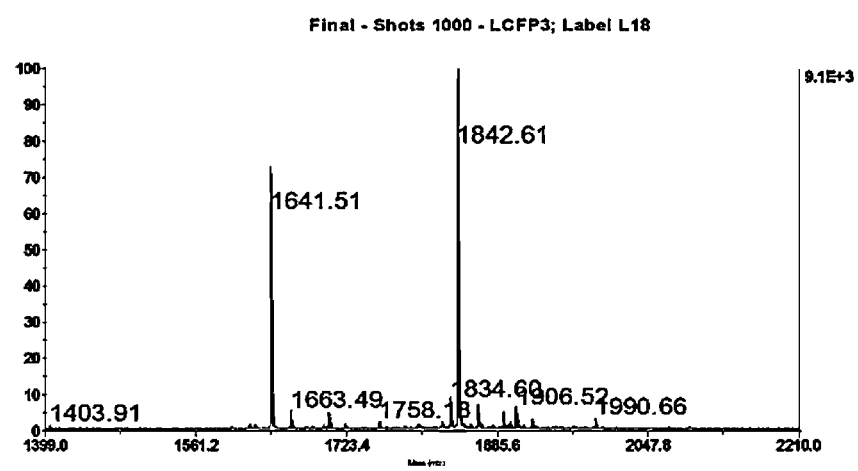
Figure 11D:
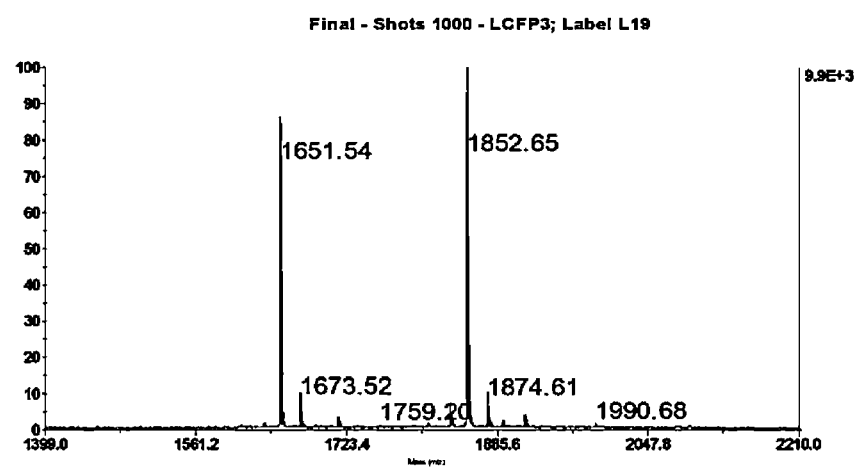
Figure 11D:
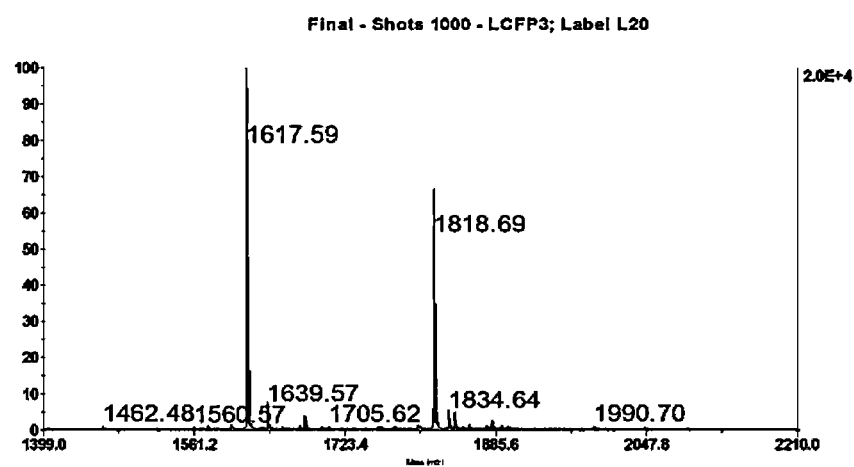

FIG. 11 shows a screen for substrate sequence specificity of the C- or N-terminal end peptide/protein: (a) Asn-Xaa$^3$-Leu-COOH; (b) Asn-Gly-Xaa$^2$-COOH; and (c) H2N-Xaa$^1$-Leu. 100 μM substrate, with 50 nM Quicklase, reacted for 5 mins at room temperature, under neutral pH (pH 7.4) standard reaction buffer. The % of self-ligated (cyclized) peptides could be used as qualitative indications of Kcat. The raw Mass-spec reading of the assay readout were also included in FIG. 11(d).

Figures 12A, 12B:
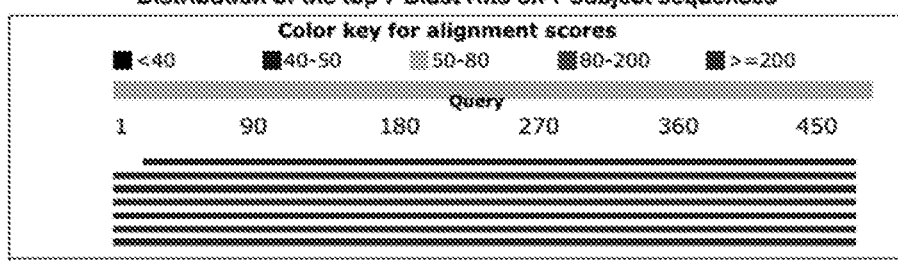

FIG. 12 shows (a) a graphic summary of a Basic Local Alignment Search Tool (BLAST) search in the National Center for Biotechnology Information (NCBI) database performed with the amino acid sequence set forth in SEQ ID NO:1 (OaAEP1 Cys247Ala) and (b) the sequences producing significant alignments.

Figure 13:
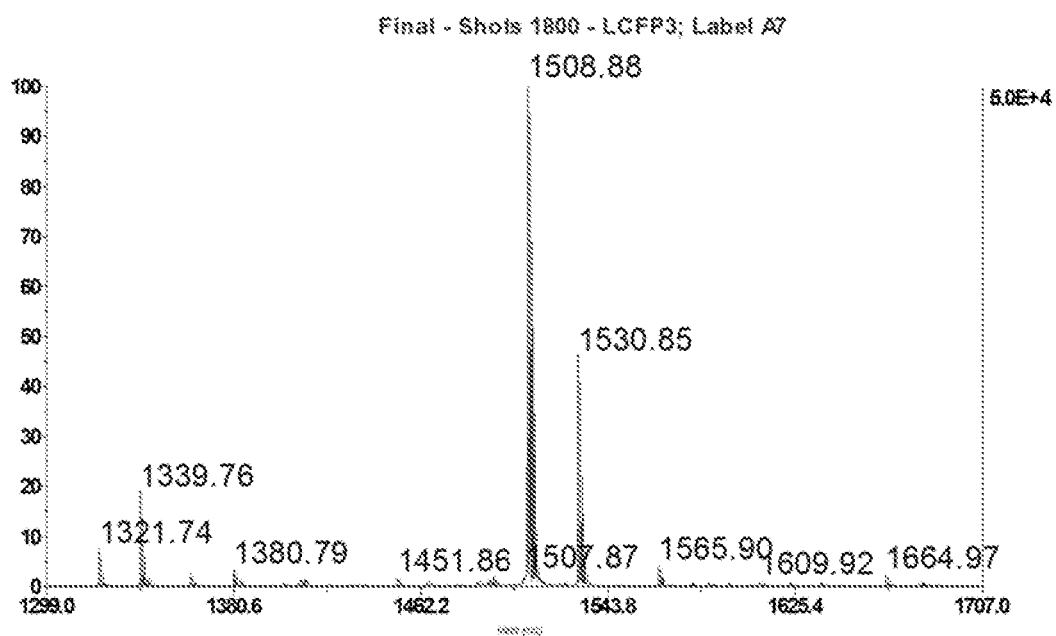

FIG. 13 shows that AEP_C13CO4 having the amino acid sequence set forth in SEQ ID NO:8 is a peptide ligase having the activity of OaAEP1 Cys247Ala (SEQ ID NO:1).

Figure 14:
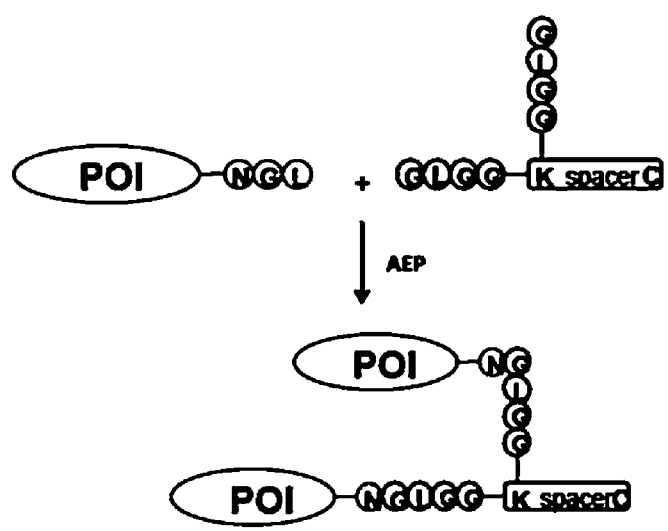
Figure 14:
Figure 14:
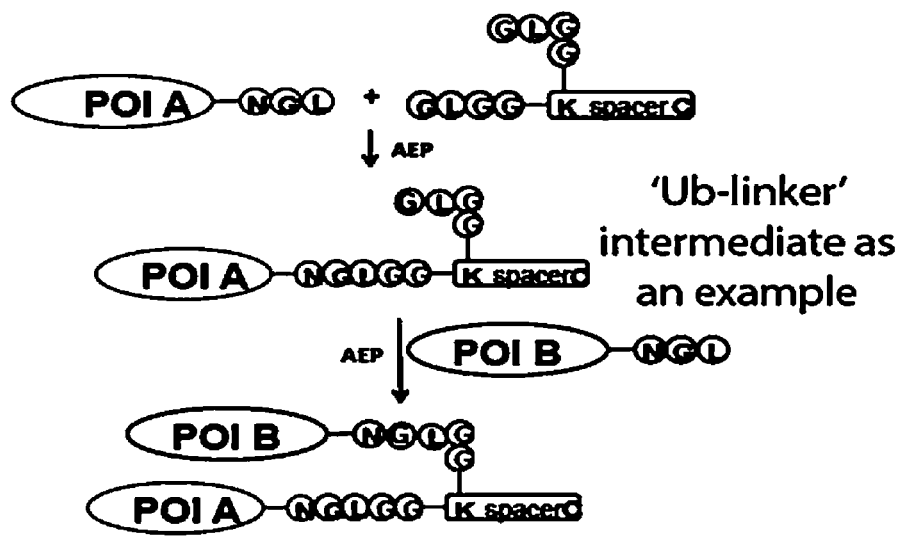
Figure 14:
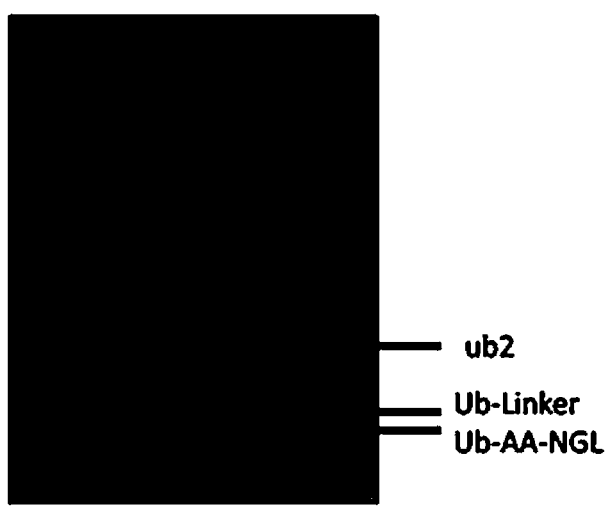
Figure 14:
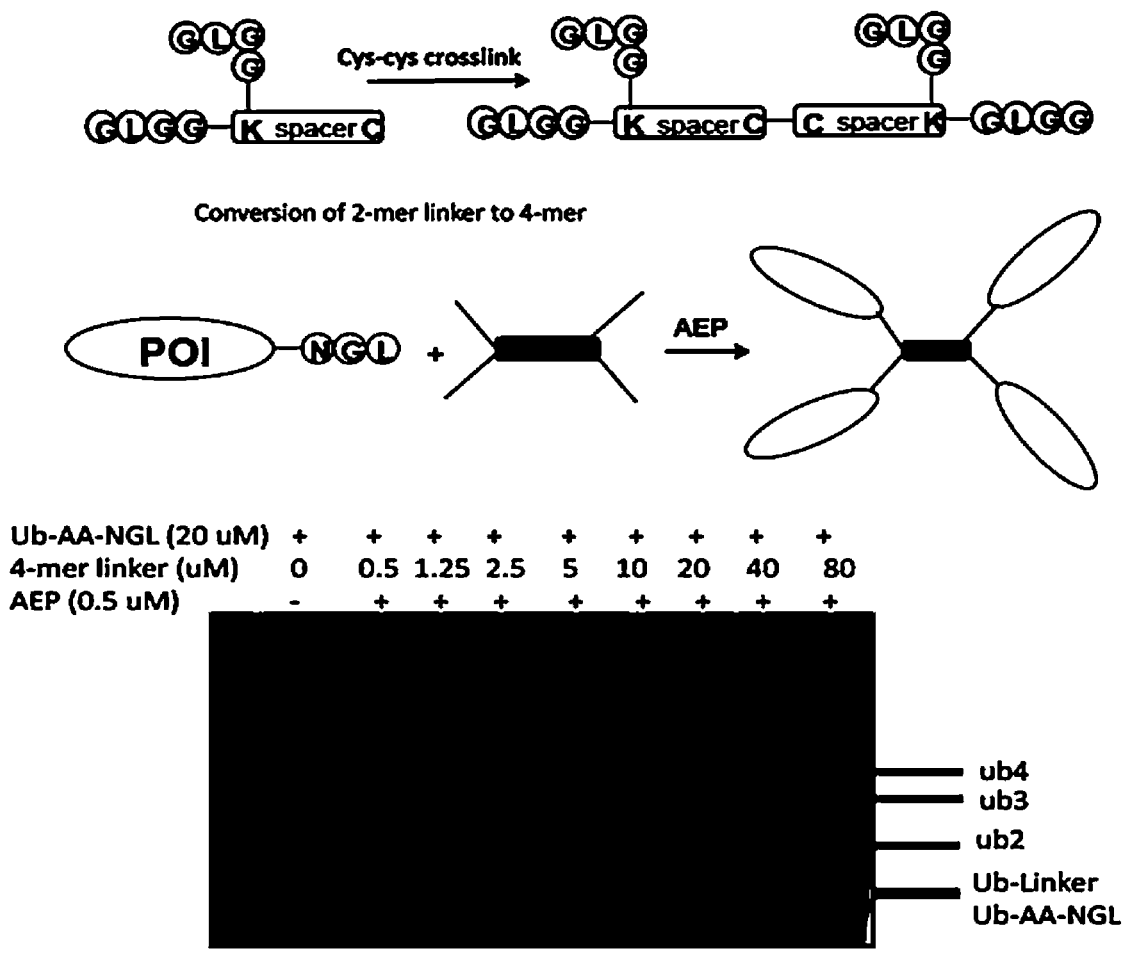
Figure 14:
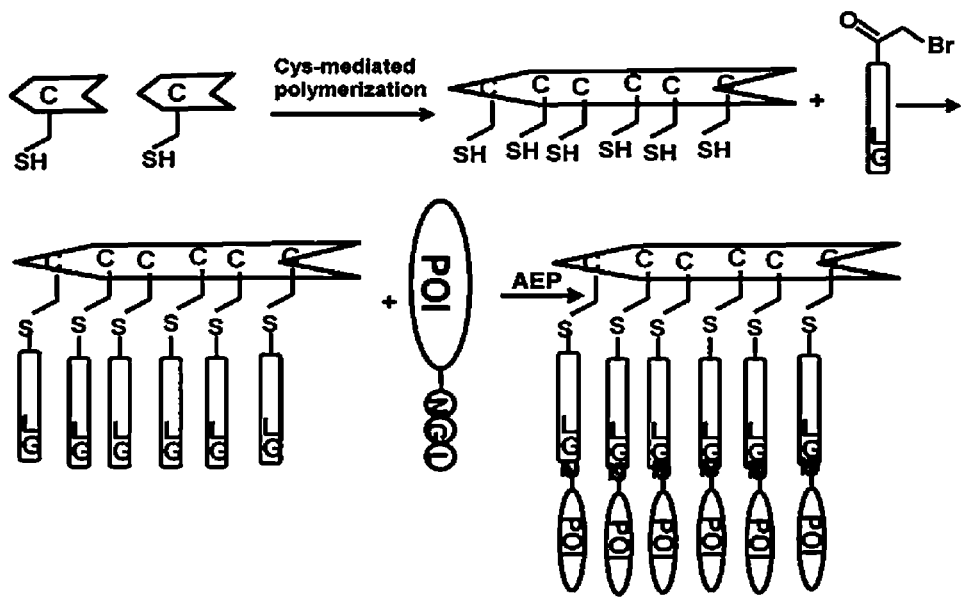
Figure 14:
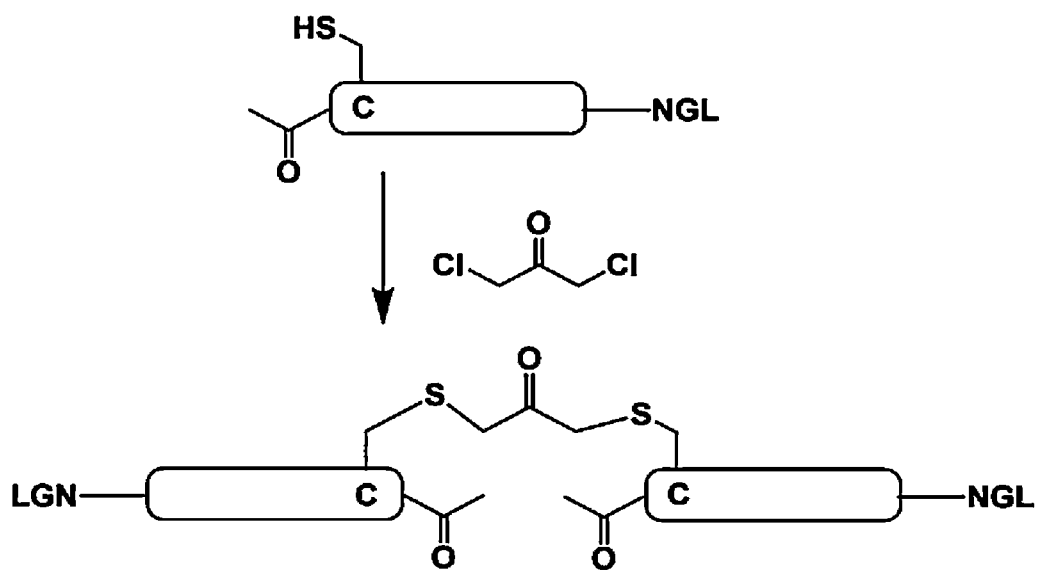
Figure 14:
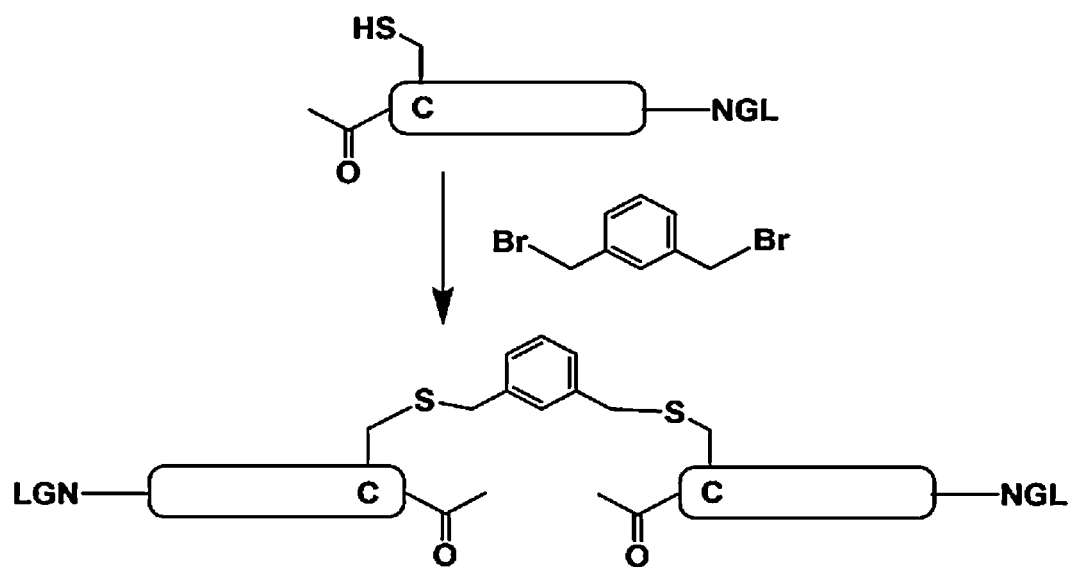
Figure 14:
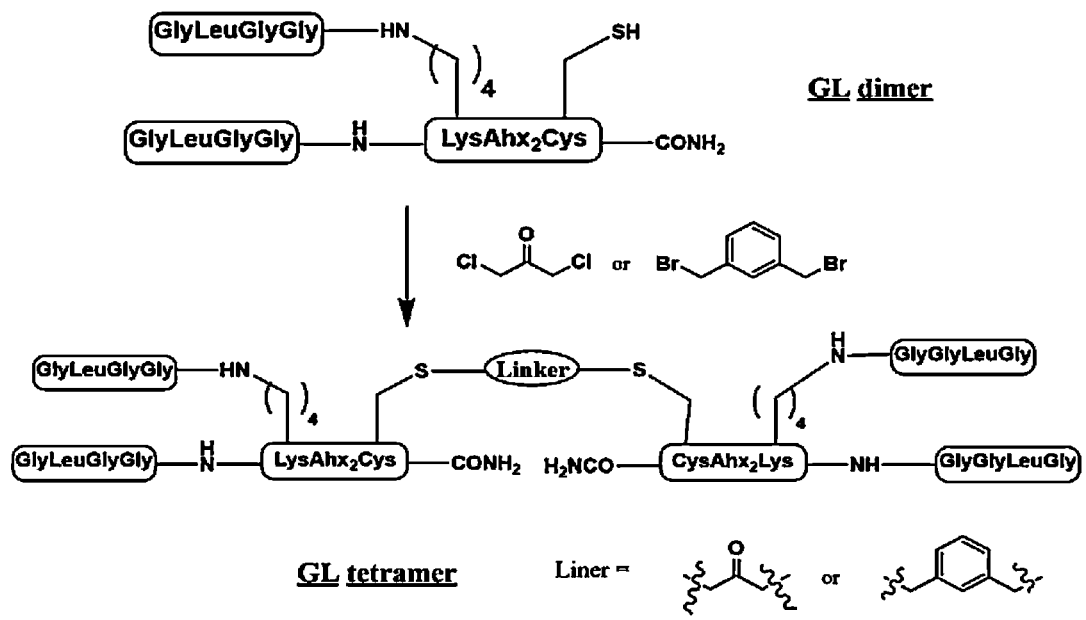
Figure 14:
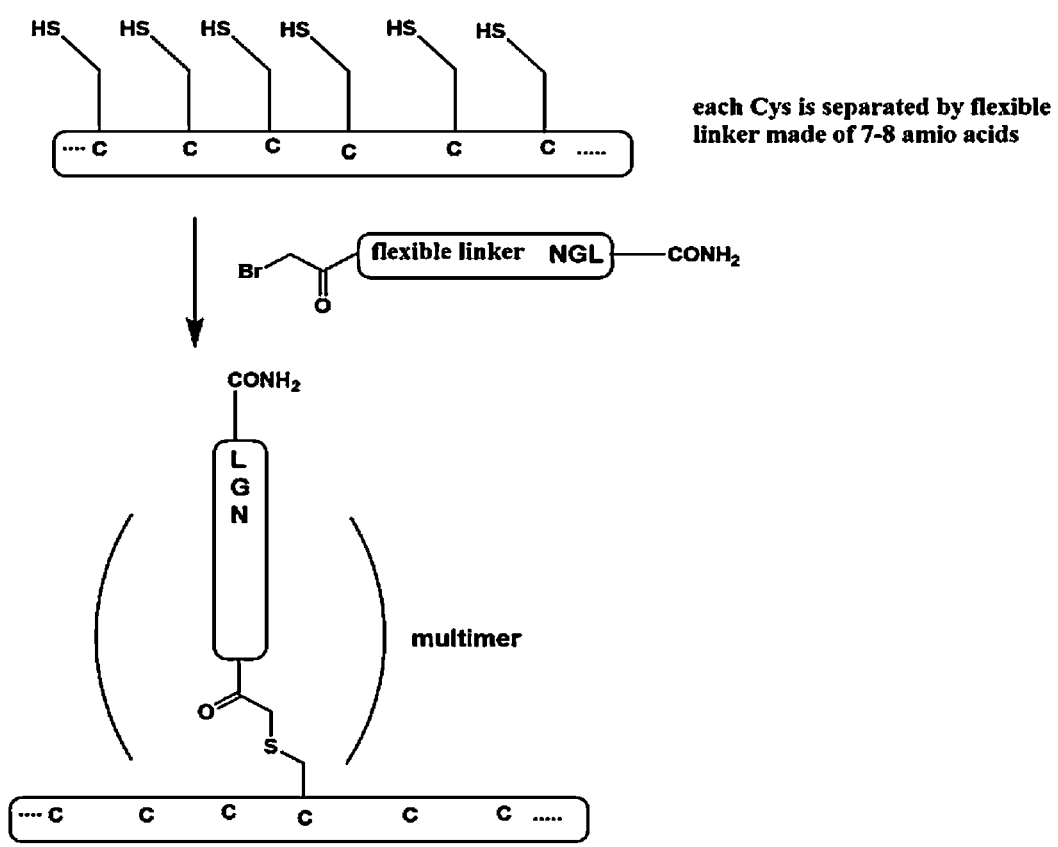
Figure 14:
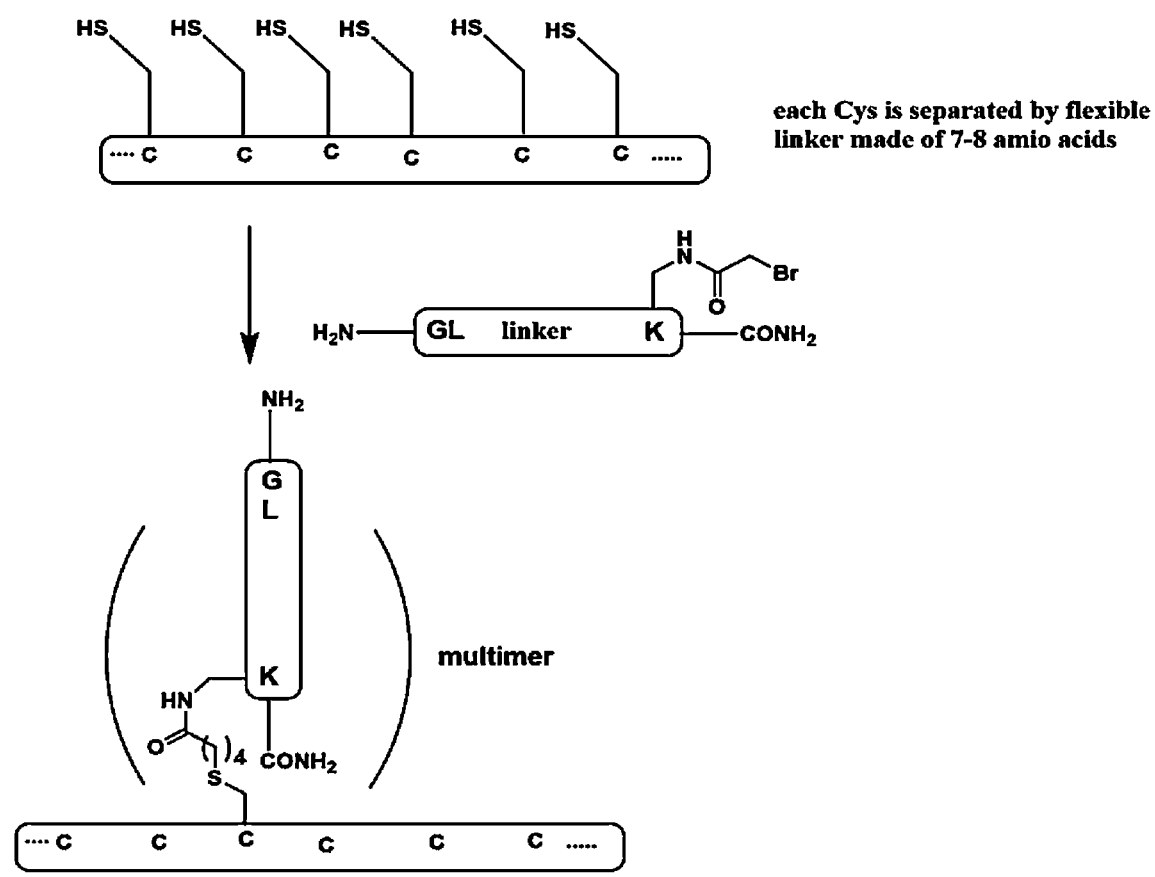

FIG. 14 shows schemes for (a) scaffold-based one-step homodimerization, (b) scaffold-based two-step heterodimerization, (c) scaffold-based one-step tetramerization, and (d) modular ultra-oligomerization. Additionally shown are schemes for preparing (e, NGL head-to-head dimers, (g) GL linker dimers and tetramers, (h) NGL multimers, and (i) GL multimers.

Figure 15:
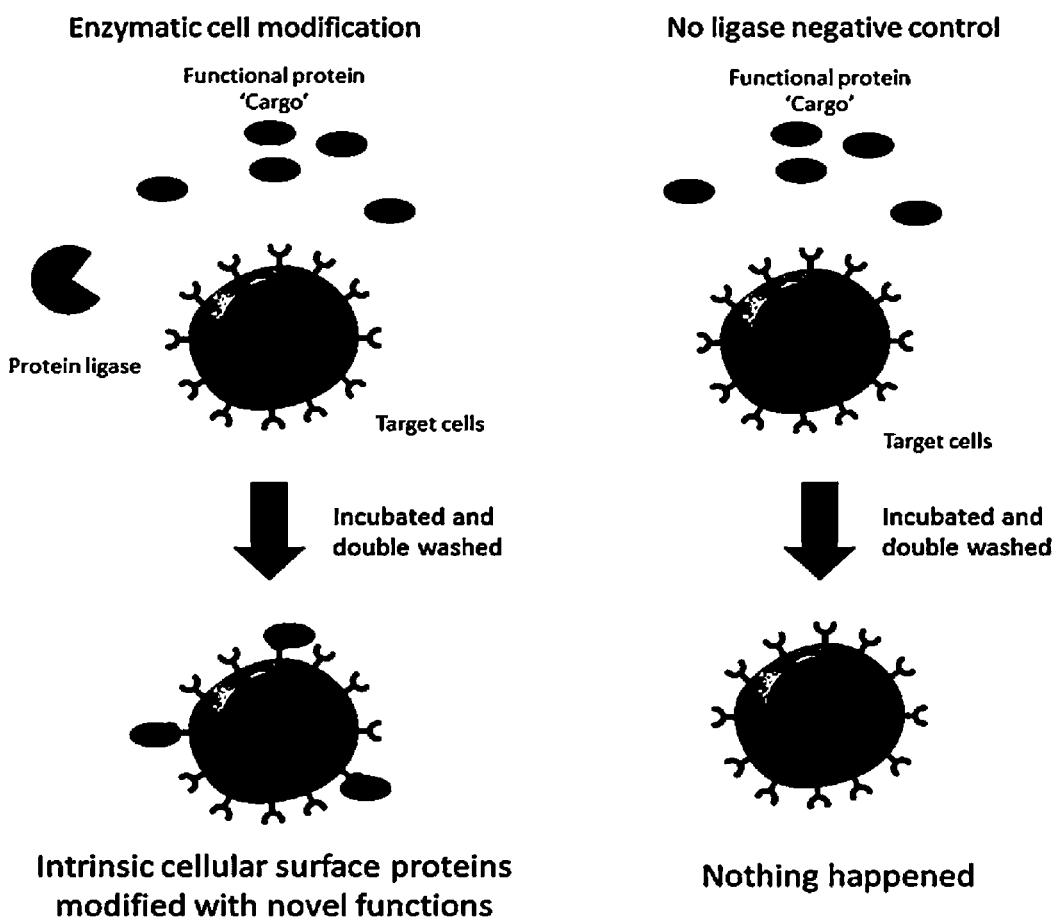
Figure 15:
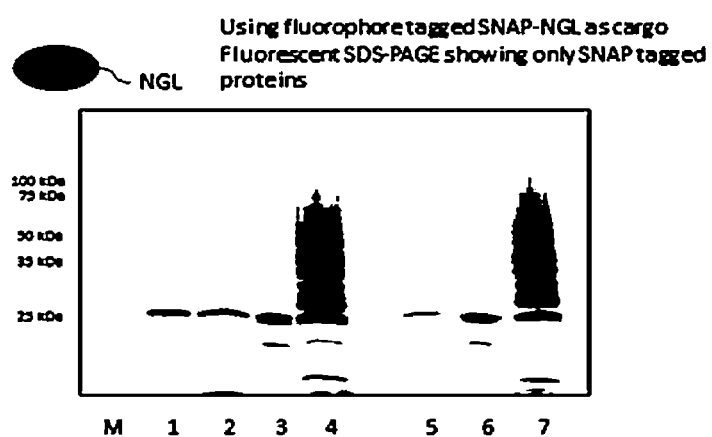
Figure 15:

FIG. 15 shows (a) a schematic illustration of the direct cellular modification procedure mediated by OaAEP1 Cys247Ala (SEQ ID NO:1). (b) Fluorecently tagged SNAP (New England Biolabs) protein was conjugated to the intrinsic cellular surface proteins of two different cell lines, RAW cell (human macrophage cell line) and HEK293T (human epithelial cell line). 10 μM modified SNAP protein (with additional C-terminal NGL residues, lane 1 sample) with or without (lane 2 and lane 5 samples) coincubation of 0.1 μM Quicklase were added to cell culture, pre-washed with PBS buffer. After 30 minutes~1 hour incubation, cells were rinsed with additional PBS buffer (lane 3 and lane 6 were first wash samples), two times. The remaining cell was harvested and lysed with SDS loading buffer (lane 4 and 7 samples). All samples were examined using SDS-PAGE, and only the covalently fluorescently tagged SNAP protein carried the signal on the gel, which were shown as dark bands in (b). Additional bands in lane 4 and 7 indicated that significant amount of intrinsic proteins in RAW and HEK283T cells were conjugated with SNAP protein, in a Quicklase dependent way. (c) Surface modified RAW cells were examined using a fluorescent microscope, bright spots on the cellular surface indicated successful surface labelling of intrinsic cellular membrane. Certain intrinsic proteins with amino acids residue sequences closely related to formula III could be recognized as Quicklase, due to its superior enzymatic activity and broader sequence recognition ability.

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

Breaking and forming peptidyl bonds are fundamental biochemical reactions in protein chemistry. Unlike proteases that are abundantly available, fast-acting ligases are rare. OaAEP1 is an enzyme isolated from the cyclotide-producing plant *Oldenlandia affinis* that displayed weak peptide cyclase activity, despite having a similar structural fold with other asparaginyl endopeptidases (AEP). The inventors of the present application report herein the first atomic structure of OaAEP1, at a resolution of 2.56 Å, in its pre-activation form. The structure and biochemical analysis of this enzyme reveals its activation mechanism as well as structural features important for its ligation activity. Importantly, through structure-based mutagenesis of OaAEP1, the inventors obtained an ultra-fast variant having hundreds of times faster catalytic kinetics, capable of ligating well-folded protein substrates using only sub-micro molar concentration of enzyme. In contrast, the protein-protein ligation activity in the original wild-type OaAEP1 enzyme described previously is extremely weak. Thus, the structure-based identification of a biochemical motif described herein leads to characterization of a unique and novel recombinant tool (OaAEP1 Cys247Ala having the amino acid sequence set forth in SEQ ID NO:1) and its related structural homologs that can now be used to conduct various protein labeling and modifications that were extremely challenging before. For example, more efficient peptide cyclization and peptides/proteins can be enzymatically catalyzed. Furthermore, this new type of recombinant enzyme, and its structural homologs enable novel biochemical applications, like modifications of intrinsic cellular surface proteins.

The object of the present invention is to provide a technique for ligating peptides, taking advantage of the superior site specificity and catalytic efficiency of OaAEP1 Cys247Ala-like Asx-specific protein ligases.

To this end, provided in a first aspect of the present invention is a method of generating a peptide of Formula (I)

$$P^1\text{-Asx-Xaa}^1\text{-Xaa}^2\text{-}P^2 \quad (I),$$

by ligating a first peptide of Formula (II)

$$P^1\text{-Asx-Xaa}^3\text{-Leu-COOH/CONH}_2 \quad (II)$$

to a second peptide of Formula (III)

$$H_2N\text{-Xaa}^1\text{-Xaa}^2\text{-}P^2 \quad (III),$$

wherein $P^1$ and $P^2$ are each independently any peptide, modified or unmodified, and optionally can combine such that the peptides of formula (II) and (III) are the termini of the same peptide; Asx is Asp or Asn; $Xaa^1$ is any naturally occurring amino acid; $Xaa^2$ is any naturally occurring amino acid with the exception of Pro, preferably Leu or Ile; and Xaa3 is any naturally occurring amino acid, preferably selected from the group consisting of His, Ala, Ser, Cys, Asn, Gly, Arg, Met, Lys, Gln, Leu, and Glu, by enzymatically cleaving the bond between "Asx" and "$Xaa^3$" in the first peptide of Formula (II) and ligating the fragment $P^1$-Asx of the first peptide via its C-terminus to the N-terminus of the second peptide of Formula (III) to form a ligated peptide of Formula (I), wherein the enzymatic cleavage and ligation reaction is catalyzed by a peptide ligase having the activity of OaAEP1 Cys247Ala (SEQ ID NO:1) under conditions suitable for said cleavage and ligation reaction.

In the context of the whole application, the terms "peptide", "polypeptide", and "protein" are used interchangeably to refer to polymers of amino acids of any length connected by peptide bonds. The polymer may comprise modified amino acids, it may be linear or branched, and it may be interrupted by non-amino acids. The terms also encompass an amino acid polymer that has been modified naturally or artificially; for example, by disulfide bond formation, glycosylation, lipidation, acetylation, phosphorylation, or any other manipulation, such as conjugation to a labeling moiety. However, in preferred embodiments, these terms relate to polymers of naturally occurring amino acids, as defined below, which may optionally be modified as defined above, but does not comprise non-amino acid moieties in the polymer backbone.

The term "amino acid" refers to natural and/or unnatural or synthetic amino acids, including both the D and L optical isomers, amino acid analogs (for example norleucine is an analog of leucine) and derivatives known in the art. The term "naturally occurring amino acid", as used herein, relates to the 20 naturally occurring L-amino acids, namely Gly, Ala, Val, Leu, Ile, Phe, Cys, Met, Pro, Thr, Ser, Glu, Gln, Asp, Asn, His, Lys, Arg, Tyr, and Trp. The term "peptide bond" refers to a covalent amide linkage formed by loss of a molecule of water between the carboxyl group of one amino acid and the amino group of a second amino acid. The "-" between $P^1$ and Asx in Formula (I), as well as all "-" in Formula (I) represent peptide bonds. In addition, "Leu-COOH/CONH$_2$" represents Leucine or Leucinamide, so the "-" between "Leu" and "COOH/CONH$_2$" in Formula (II) represents the covalent bond between the α-carbon and the carboxyl or carboxamide group of Leucine/Leucinamide. Likewise, "H$_2$N-Xaa$^1$" in Formula (III) represents amino acid residue Xaa$^1$, so the "-" between "NH$_2$" and "Xaa$^1$" represents the covalent bond between the α-carbon and the amino group of Xaa$^1$. It is understood that the carboxyl/carboxamide group in the peptide of formula (II) and the amino group in the peptide of formula (III) form part of the terminal amino acid and are not additional functional groups. Generally, in all formulae depicted herein, the peptides are shown in the N- to C-terminal orientation.

Without wishing to be bound to any particular theory, it is believed that the peptide ligase having the activity of OaAEP1 Cys247Ala (SEQ ID NO:1) as described herein can also catalyze the ligation between any one substance or object comprising a terminal "Asx-Xaa$^3$-Leu-COOH/CONH$_2$" motif and any one substance or object comprising a terminal "H$_2$N-Xaa$^1$-Xaa$^2$" motif. In this connection, it should be noted that the method described herein also applies mutatis mutandis to embodiments wherein one or both of $P^1$ and $P^2$ are any substance or object other than peptide, which is also within the scope of the present application.

In various embodiments,
(a) Asx is Asn or Asp; and/or
(b) Xaa$^1$ is all naturally occurring amino acids; and/or
(c) Xaa$^2$ is Leu or Ile; and/or
(d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e. (a) and (b), (a) and (c), (a) and (d), (b) and (c), (b) and (d), or three or more features are met, i.e. (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly, meaning that Asx is Asn, Xaa$^1$ is Arg, Xaa$^2$ is Leu, Xaa$^3$ is His; Asx is Asn, Xaa$^1$ is Arg, Xaa$^2$ is Leu, Xaa$^3$ is Ala; Asx is Asn, Xaa$^1$ is Arg, Xaa$^2$ is Leu, Xaa$^3$ is Gly; Asx is Asn, Xaa$^1$ is Gly, Xaa$^2$ is Leu, Xaa$^3$ is His; Asx is Asn, Xaa$^1$ is Gly, Xaa$^2$ is Leu, Xaa$^3$ is Ala; or Asx is Asn, Xaa$^1$ is Gly, Xaa$^2$ is Leu, Xaa$^3$ is Gly.

It should be noted that, according to FIG. 11(b), the "Leu" residue of the first peptide of Formula (II), i.e. $P^1$-Asx-Xaa$^3$-Leu-COOH/CONH$_2$, may also be replaced by another naturally occurring amino acid, e.g. Ile, Pro, Phe, Cys, Gln, or Lys, provided that said peptide in this form is still suitable for the method described herein. Such embodiments in combination with any of the embodiments described herein are also fully encompassed by the present application.

It is also envisaged that, when the first peptide and the second peptide are termini of the same peptide, i.e. $P^1$ and $P^2$ combine to form the core sequence of a peptide terminated by the sequences of formula (II) and (III), the presently disclosed method cyclizes said peptide.

The peptide ligase having the activity of OaAEP1 Cys247Ala (SEQ ID NO:1) for use in the present invention may be any oaAEP family enzymes or homologous thereof having the desired activity. The peptide ligase has an ability to site-specifically break a peptide bond and then reform a new bond with an incoming nucleophile. It is Asx-specific in that the C-terminal amino acid to which ligation occurs, i.e. the C-terminal end of the peptide that is ligated, is either Asn or Asp, preferably Asn. As set forth above, it recognizes the motif Asx-Xaa$^3$-Leu-COOH/CONH$_2$, at the C-terminus of the first peptide of Formula (II), and mediates peptide ligation by cleaving off the sorting signal Xaa$^3$-Leu-COOH/CONH$_2$ and ligating $P^1$-Asx to the N-terminal residue of the second peptide H2N-Xaa$^1$-Xaa$^2$-$P^2$ to form a ligated peptide $P^1$-Asx-Xaa$^1$-Xaa$^2$-$P^2$.

In various embodiments, the peptide ligase having the activity of OaAEP1 Cys247Ala (SEQ ID NO:1) in accordance with the present application comprises, consists of, or essentially consists of:
(a) the amino acid sequence set forth in SEQ ID NO:1 (OaAEP1 Cys247Ala);
(b) an amino acid sequence that shares at least 65%, preferably at least 75%, even more preferably at least 85%, most preferably at least 95% sequence identity with, or at least 80%, preferably at least 90%, more preferably at least 95% sequence homology with the amino acid sequence as set forth in SEQ ID NO:1, provided that said peptide ligase comprises the amino acid sequence set forth in SEQ ID NO:2 at the positions corresponding to residues 247-264 of SEQ ID NO:1, which defines a unique surface structural feature of the enzyme serving as the binding site for approaching N-terminal amino group;
(c) a functional fragment of (a) or (b); or
(d) an amino acid sequence containing either (a) or (b) or (c) as its essential component, with the proviso that said peptide ligase is not the wild-type OaAEP1 having the amino acid sequence set forth in SEQ ID NO:3 or butelase 1 having the amino acid sequence set forth in SEQ ID NO:4.

In various embodiments, the peptide ligase having the activity of OaAEP1 Cys247Ala (SEQ ID NO:1) comprises, consists of, or essentially consists of:
(a) the amino acid sequence set forth in SEQ ID NO:1;
(b) the amino acid sequence set forth in SEQ ID NO:5;
(c) the amino acid sequence set forth in SEQ ID NO:6;
(d) the amino acid sequence set forth in SEQ ID NO:7;
(e) the amino acid sequence set forth in SEQ ID NO:8;
(f) the amino acid sequence set forth in SEQ ID NO:9;
(g) the amino acid sequence set forth in SEQ ID NO:10; or
(h) the amino acid sequence set forth in SEQ ID NO:11.

In preferred embodiments, the peptide ligase comprises or consists of the amino acid sequence as set forth in SEQ ID NO:1 (OaAEP1 Cys247Ala).

The identity of nucleic acid or amino acid sequences is generally determined by means of a sequence comparison. This sequence comparison is based on the BLAST algorithm that is established in the existing art and commonly used (cf. for example Altschul et al. (1990) "Basic local alignment search tool", J. Mol. Biol. 215:403-410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, which is calculated in relation to a reference sequence and its entire length. The term "sequence identity" refers to the extent that sequences are identical on a nucleotide-by-nucleotide or amino acid-by-amino acid basis over a window of comparison. Thus, a "percentage of sequence identity" is calculated by comparing two optimally aligned sequences over the window of comparison, determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity. The more broadly construed term "homology", in the context of amino acid sequences, also incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous and identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity and homology herein refer to the full length of the respectively indicated nucleic acid sequence or amino acid sequence.

While it is recognized that various peptide ligases as described above may be suitable for the practice of the present invention, it is preferable to use one with potent protein ligase actively. In various embodiments, this means that it can ligate a given peptide with an efficiency of at least 50%, preferably at least 70%, more preferably at least 90%, most preferably at least 95%. Methods to determine such efficiency by, for example, ligating substrate (100 µM) in the presence of said peptide ligase (50 nM) for 30 mins in a standard reaction buffer at neutral pH and room temperature, are well known in the art and can be routinely applied by those skilled in the art, for example. It is preferred that the peptide ligases of the invention have at least 50%, more preferably at least 70%, most preferably at least 90% of the protein ligase activity of the enzyme having the amino acid sequence of SEQ ID NO:1.

Peptide ligases having the activity of OaAEP1 Cys247Ala (SEQ ID NO:1) according to the present application can comprise amino acid modifications, in particular amino acid substitutions, insertions, or deletions. Such peptide ligases are, for example, further developed by targeted genetic modification, i.e. by way of mutagenesis methods, and optimized for specific purposes or with regard to special properties (for example, with regard to their catalytic activity, stability, etc.). The objective may be to introduce targeted mutations, such as substitutions, insertions, or deletions, into the known molecules in order, for example, to alter substrate specificity and/or improve the catalytic activity. For this purpose, in particular, the surface charges and/or isoelectric point of the molecules, and thereby their interactions with the substrate, can be modified. Alternatively or additionally, the stability of the peptide ligase can be enhanced by way of one or more corresponding mutations, and its catalytic performance thereby improved. Advantageous properties of individual mutations, e.g. individual substitutions, can supplement one another.

In various embodiments, the peptide ligase may be characterized in that it is obtainable from a peptide ligase as described above as an initial molecule by single or multiple conservative amino acid substitution. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I—V=L=M, D=E, N=Q, K=R, Y=F, and S=T.

Alternatively or additionally, the peptide ligase may be characterized in that it is obtainable from a peptide ligase contemplated herein as an initial molecule by fragmentation or by deletion, insertion, or substitution mutagenesis, and encompasses an amino acid sequence that matches the initial molecule over a length of at least 150, 160, 170, 180, 190, 200, 210, 220, 230, 240, 250, 260, 270, 280, 290, or 300 continuously connected amino acids, provided that said peptide ligase comprises the amino acid sequence set forth in SEQ ID NO:2 at the positions corresponding to residues 247-264 of SEQ ID NO:1.

In various embodiments, the present invention thus also relates to functional fragments of the peptide ligases described herein, with said fragments retaining enzymatic activity. It is preferred that they have at least 50%, more preferably at least 70%, most preferably at least 90% of the protein ligase activity of the initial molecule, preferably of the peptide ligase having the amino acid sequence of SEQ ID NO:1. The functional fragments are preferably at least 150 amino acids in length, more preferably at least 180 or 200, most preferably at least 250.

In various embodiments, the peptides to be ligated in accordance with the present application may be modified by, for example, conjugation to a labeling moiety, either covalently or non-covalently. A labeling moiety may be any molecules such as, without limitation, an affinity tag, therapeutic agent, detectable label, or scaffold molecule.

In various embodiments, the first and/or second peptide may be coupled to a solid support material.

The term "affinity tag" as used herein refers to a moiety such as biotin that can be used to separate a molecule to which the affinity tag is attached from other molecules that do not contain the affinity tag.

The term "detectable label" is intended to mean at least one label capable of directly or indirectly generating a detectable signal. In non-limiting examples, a detectable label can be an enzyme producing a detectable signal, for example by colorimetry, fluorescence, or luminescence; a chromophore, such as a fluorescent, luminescent or dye compound, e.g. GFP; a group with an electron density detectable by electron microscopy or by virtue of their electrical property, such as conductivity, amperometry, voltammetry or impedance; detectable group, for example the molecules of which are sufficiently large to induce detectable modifications of their physical and/or chemical characteristics (this detection can be carried out by optical methods such as diffraction, surface plasmon resonance, surface variation or contact angle variation, or physical methods such as atomic force spectroscopy or the tunnel effect; or a radioactive molecule such as $^{32}$P, $^{35}$S or $^{125}$I.

The term "scaffold molecule" as used herein refers to a compound to which other moieties are attached, covalently or non-covalently. Various scaffold molecules such as dendrimers are well known in the art.

The term "solid support material" as used herein refers to a solid or semi-solid (e.g., a hydrogel) material onto which the peptide can be immobilized. Non-limiting examples include solid supports for peptide synthesis, magnetic beads, glass fibers, and resins.

Peptides modified by the labeling moiety may be prepared using standard techniques known to those skilled in the art of synthetic organic chemistry, or may be deduced by reference to the pertinent literature.

In various embodiments, the first and/or second peptide is a cellular surface protein such that the method results in the modification or tagging of the cellular surface protein and in result the cellular surface as such.

In a second aspect, the invention relates to a method of preparing a dimer, oligomer, or multimer of one or more peptides of interest, the method comprising the steps of:

(a) providing one or more peptides of interest having C-terminal Asx-Xaa$^3$-Leu-COOH/CONH$_2$ residues and a scaffold molecule having two or more copies of N-terminal H$_2$N-Xaa$^1$-Xaa$^2$ residues or, alternatively, providing one or more peptides of interest having N-terminal H2N-Xaa$^1$-Xaa$^2$ residues and a scaffold molecule having two or more copies of C-terminal Asx-Xaa$^3$-Leu-COOH/CONH$_2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1), as described above;

(c) preparing a mixture of the one or more peptides of interest, the scaffold molecule, and the peptide ligase having the activity of OaAEP1 Cys247Ala(SEQ ID NO:1);

(d) subjecting the mixture to conditions that allow the peptide ligase having the activity of OaAEP1 Cys247Ala (SEQ ID NO:1) to catalyze the ligation of the one ore more peptides of interest to the scaffold molecule.

In various embodiments, (a) Asx is Asn or Asp, and/or (b) Xaa$^1$ is all naturally occurring amino acids, and/or (c) Xaa$^2$ is Leu or Ile, and/or (d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e. (a) and (b), (a) and (c), (a) and (d), (b) and (c), (b) and (d), or three or more features are met, i.e. (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly.

FIG. 14 (a)-(d) show how hetero- or homo-dimers, oligomers, or multimers of one or more peptides of interest can be prepared according to some non-limiting embodiments. FIG. 14 (e)-(i) show some non-limiting examples of how scaffold molecules for use in the present invention can be prepared.

In a third aspect, the invention relates to a method of modifying or tagging the surface of a target cell by one or more peptides of interest, the method comprising the steps of: (a) providing the one or more peptides of interest having C-terminal Asx-Xaa$^3$-Leu-COOH/CONH$_2$ residues and/or having N-terminal H2N-Xaa$^1$-Xaa$^2$ residues, wherein Asx is Asp or Asn; Xaa$^1$ is any naturally occurring amino acid; Xaa$^2$ is any naturally occurring amino acid with the exception of Pro, preferably Leu or Ile; and Xaa$^3$ is any naturally occurring amino acid, preferably selected from the group consisting of His, Ala, Ser, Cys, Asn, Gly, Arg, Met, Lys, Gln, Leu, and Glu;

(b) providing a peptide ligase having the activity of OaAEP1 Cys247Ala (SEQ ID NO:1), as described above;

(c) contacting the target cell with the one or more peptides of interest and the peptide ligase having the activity of OaAEP1 Cys247Ala (SEQ ID NO:1);

(d) subjecting the target cell to conditions that allow the peptide ligase having the activity of OaAEP1 Cys247Ala (SEQ ID NO:1) to catalyze the ligation of the one or more peptides of interest to a cellular surface protein of the target cell.

In certain embodiments, the wild-type OaAEP1 having the amino acid sequence of SEQ ID NO:3 may also be used in this method, probably with a compromised efficiency.

In various embodiments, (a) Asx is Asn or Asp; and/or (b) Xaa$^1$ is all naturally occurring amino acids; and/or (c) Xaa$^2$ is Leu or Ile; and/or (d) Xaa$^3$ is selected from the group consisting of His, Ala, Ser, Cys, Asn, Gly, Arg, Met, Lys, Gln, Leu, and Glu.

In preferred embodiments, two or more of features (a)-(d) are met, i.e. (a) and (b), (a) and (c), (a) and (d), (b) and (c), (b) and (d), or three or more features are met, i.e. (a), (b) and (c), (a), (b) and (d), (a), (c) and (d), (b), (c) and (d) or, most preferably all four are met.

In preferred embodiments, Asx is Asn, Xaa$^1$ is any naturally occurring amino acid, Xaa$^2$ is Leu, and Xaa$^3$ is His, Ser, Cys, Gly or Ala.

In more preferred embodiments, Asx is Asn, Xaa$^1$ is Arg or Gly, Xaa$^2$ is Leu, and Xaa$^3$ is His, Ala or Gly.

In various embodiments, the method further comprises removing the unligated one or more peptides from the target cell after step (d).

The one or more peptides of interest may be functionalized to bind a variety of cargo molecules. In various embodiments, the one or more peptides of interest comprise a labeling moiety such as an affinity tag, therapeutic agent, detectable label, or scaffold molecule, as already described above. The one or more peptides of interest may also be coupled to a solid support material.

FIG. 15(a) shows how a target cell can be tagged according to a non-limiting embodiment of the invention.

The method described herein may be applicable to all types of cells in vitro, ex vivo, or in vivo. The target cell may be any prokaryotic or eukaryotic cell, e.g. a bacterial, yeast, plant, or human cell; it may be a cancer cell, oocyte, embryonic stem cell, hematopoietic stem cell, or any other differentiated or undifferentiated cell, provided that the target cell expresses a surface polypeptide having C-terminal Asx-Xaa³-Leu-COOH/CONH₂ or N-terminal H2N-Xaa¹-Xaa² residues that are accessible to the one or more peptides of interest.

In preferred embodiments, the target cell expresses endogenous surface proteins suited for ligation to the one or more peptides of interest. However, the target cell may also recombinantly express a surface polypeptide having N-terminal H₂N-Xaa¹-Xaa² or C-terminal Asx-Xaa³-Leu-COOH residues for ease of tagging by the peptide of interest.

The term "recombinantly express" as used herein refers to the expression of said polypeptide by recombinant DNA technology.

It is also within the scope of the present invention that the one or more peptides of interest may be polypeptides endogenously or recombinantly expressed on the surface of the target cell, in which case no additional said peptides need to be provided and the method described herein results in hetero- or homo-dimerization, oligomerization, or multimerization of surface proteins of the target cell.

It is therefore believed that the present invention provides a versatile and fast-acting technology for modifying or tagging cell surface by attaching modified or unmodified peptides of interest. Compared to conventional chemical labeling strategies, this method enables specific and fast conjugation to the N- and/or C-terminus of surface proteins.

In a fourth aspect, the invention relates to the ligated peptides and/or tagged target cells obtainable according to any of the methods of the invention.

In a fifth aspect, the invention relates to the peptide ligase OaAEP1 Cys247Ala having the amino acid sequence of SEQ ID NO:1 and other peptide ligases having the activity thereof, as described above, as well as kits comprising any of said peptide ligases, in particular OaAEP1 Cys247Ala (SEQ ID NO:1).

In still another aspect, the present invention relates to the use of a peptide ligase having the activity of OaAEP1 Cys247Ala (SEQ ID NO:1) for the ligation of two peptides, as described herein.

The present invention is further illustrated by the following examples. However, it should be understood, that the invention is not limited to the exemplified embodiments.

EXAMPLES

Materials and Methods
Quicklase Preparation:

OaAEP1 was cloned and expressed in *E. coli* as an ubiquitin fusion protein. A gene with codons optimized for expression in *E. coli*, encoding a protein (SEQ ID NO:12) composed of a N-terminal hexa-His tag (SEQ ID NO:13), the 76 amino-acid residues human ubiquitin (SEQ ID NO:14), and residues 24-474 of OaAEP1 (SEQ ID NO:15), devoid of the OaAEP1 signal peptide) was synthesized by Genescript, USA.

The clone is OaAEP1 one amino acid different from OaAEP1b (SEQ ID NO:3) (with E371V mutation). OaAEP1 was cloned from mRNA and OaAEP1b from genomic DNA sequence. Nevertheless, the wild type constructs (OaAEP1, SEQ ID NO:3) of the inventors behaves essentially the same as previously reported (OaEP1b, SEQ ID NO:3 with E371 V mutation).

The amino acid sequence of this composite protein construct is shown in FIG. S1B. The gene was inserted into the coding region (NcoI-NdeI) of the pET-28b (+) vector and amplified. Recombinant expression of OaAEP1 in *E. coli* (using either BI21DE3 or T7 Shuffle from New England Biolabs, USA) was performed following the protocol reported previously, using a concentration of 0.4 mM IPTG to induce protein expression at 16° C. for 20 hours. Cells were then harvested by centrifugation at 4,000 g for 15 min at 4° C. and resuspended in a lysis buffer containing 50 mM Tris-HCl, pH 7.4, 150 mM NaCl, 0.05% (v/v) CHAPS, 10% (v/v) glycerol. Lysis was done by passing three times the homogenized cells through an Emulsiflex-C3 (Avestin, USA) high-pressure apparatus, at 1500 psi. The supernatant fraction, which contains His-Ub-AEP-FL (SEQ ID NO:12) and Ub-AEP-FL (SEQ ID NO:15) was further purified by metal affinity using a Ni-NTA column (Bio-Rad). His tag-containing proteins bound to the column were eluted using a linear imidazole gradient from 0 to 500 mM in a buffer containing 50 mM Tris-HCl, pH 8.0, 150 mM NaCl, 0.05% (v/v) CHAPS, 10% (v/v) glycerol. Ni-NTA elution fractions containing the protein were diluted and loaded onto two 5 ml HiTrap Q Sepharose high performance columns connected in series (GE Healthcare; 2 ml sample per ml of resin). Bound proteins were eluted using a continuous salt gradient of 0-30% of buffer B: 20 mM Bis-Tris propane, 2 M NaCl, pH 7. Finally, the protein was purified through a SEC column that had been pre-equilibrated in PBS buffer.

To self-activate OaAEP1, 1 mM EDTA and 0.5 mM Tris (2-carboxyethyl) phosphine hydrochloride were added to the immature protein and the pH of the solution was adjusted to 4 with glacial acetic acid. Fractions containing the protein (as analyzed by SDS-PAGE) were pooled and then incubated for 3 to 16 hours at room temperature or 37° C. Protein precipitation at this pH allowed removal of the bulk of the contaminating proteins by centrifugation. Activated proteins were concentrated by ultracentrifugation using a 50 kDa cutoff concentrator (Sartorius) and stored at −80° C.

Wild type and mutant ubiquitin (containing the additional "NGL" sequence at its C-terminal end) and SNAP tag (New England Biolabs) were cloned into pET47b vector and expressed in BI21(DE3) *E. coli* cells. Purification was done by metal affinity using Ni-NTA as described above. This was followed by precision protease (GE healthcare) digestion to remove the N-terminal hexa-histidine tag and SEC purification. Mutagenesis was performed using Kapa-Hifi polymerase (Kapa Biosystems) and two primers far away from each other with opposite directions.

Cys247Ala mutant was obtained through mutagenesis PCR of using primer AEP-C247A-Mut:

(SEQ ID NO: 16)
CACCACCGAAAGCAGCTGGGCCTACTATTGCCCGGCGC.

Peptides and Peptide Cyclization Assay

Native and modified amino acids were purchased from Sigma-Aldrich (USA). All peptides used in this manuscript were synthesized in-house using the solid-phase method and HPLC purified. Cyclization assays were performed in 50-μl reaction mixtures containing 20 mM phosphate buffer, ligases (5 to 700 nM) and peptide substrates (10 to 300 μM). Each reaction was performed in triplicate at 37° C. and quenched by adding 5 μl of 1 M HCl solution. The peptides were separated by using a reversed-phase C18 analytical column (150×2.1 mm, Vydac) with a linear gradient from 10% to 50% acetonitrile over 15 min on a Nexera UHPLC system (Shimadzu). For kinetic analysis, the concentrations of WT OaAEP1, mutant OaAEP1, and butelase 1 were fixed at 700 nM, 50 nM, and 20 nM, respectively. The cyclization velocities were calculated by converting the HPLC-peak areas of remained linear precursors or the cyclized products into concentrations. The identity of each HPLC peak was analyzed by MALDI-TOF MS (ABI 4800 MALDI TOF/TOF). The velocities were input into GraphPad Prism (GraphPad Software, San Diego) to obtain the Michaelis-Menten curve and the kinetic parameters (kcat and Km). Comparison for the cyclization efficiency of various OaAEP1 mutants were performed in a volume of 20 μl of the reaction mixture and analyzed by MALDI-TOF MS after 10 mins or 1 hour ligation reaction.

For quick assessment of the substrate specificity of quicklase, 100 μM peptide substrate (Xaa$^1$Xaa$^2$YRRGRLYRRNXaa$^3$Xaa$^4$, (SEQ ID NO:17) were used, with 50 nM Quicklase, reacted for 5 mins at room temperature, under neutral pH (pH 7.4) standard reaction buffer. The % of self-ligated (cyclized) peptides could be used as qualitative indications of Kcat. In each screen, only one of the residue is modified, and the default amino acid at Xaa$^1$ position is Gly, at Xaa$^2$ position is Leu, and at Xaa$^3$ position is Gly, and at the Xaa$^4$ position is Leu, in this screen (FIG. 11).

List of Sequence ID NOs and Detailed Amino Acid Sequences Described Herein

1. SEQ ID NO:1
Common Name: OaAEP1 Cys247Ala (Quicklase)
Source: *Ovaloparmena affinis*
Sequence:

MVRYLAGAVLLLVVLSVAAAVSGARDGDYLHLPSEVSRFFRPQETNDDHG
EDSVGTRWAVLIAGSKGYANYRHQAGVCHAYQILKRGGLKDENIVVFMYD
DIAYNESNPRPGVIINSPHGSDVYAGVPKDYTGEEVNAKNFLAAILGNKS
AITGGSGKVVDSGPNDHIFIYYTDHGAAGVIGMPSKPYLYADELNDALKK
KHASGTYKSLVFYLEACESGSMFEGILPEDLNIYALTSTNTTESSWAYYC
PAQENPPPPEYNVCLGDLFSVAWLEDSDVQNSWYETLNQQYHHVDKRISH
ASHATQYGNLKLGEEGLFVYMGSNPANDNYTSLDGNALTPSSIVVNQRDA
DLLHLWEKFRKAPEGSARKEEAQTQIFKAMSHRVHIDSSIKLIGKLLFGI
EKCTEILNAVRPAGQPLVDDWACLRSLVGTFETHCGSLSEYGMRHTRTIA
NICNAGISEEQMAEAASQACASIP

2. SEQ ID NO:2
Common Name: critical structural motif responsible for efficient protein ligation at the positions corresponding to residues 247-264 of SEQ ID NO:1;
Source: Based on structural analysis of this application
Sequence:

(G/A/S/C)$^{247}$-X-Y-C$^{250}$-P-X-X-X-X-P-P-P-E-Y-X-X-C$^{264}$

*X means any amino acids that do not disrupt the structural fold of the remaining conserved amino acids.
**Small amino acids (Gly, Ala, Ser or Cys) at position 247 of this structural motif allows efficient protein ligation. An Cys disulfide bond between Cys250 and Cys264 stabilize this structural motif.

3. SEQ ID NO:3
Common Name: wild type OaAEP1
Source: *Ovaloparmena affinis*
Sequence:

MVRYLAGAVLLLVVLSVAAAVSGARDGDYLHLPSEVSRFFRPQETNDDHG
EDSVGTRWAVLIAGSKGYANYRHQAGVCHAYQILKRGGLKDENIVVFMYD
DIAYNESNPRPGVIINSPHGSDVYAGVPKDYTGEEVNAKNFLAAILGNKS
AITGGSGKVVDSGPNDHIFIYYTDHGAAGVIGMPSKPYLYADELNDALKK
KHASGTYKSLVFYLEACESGSMFEGILPEDLNIYALTSTNTTESSWCYYC
PAQENPPPPEYNVCLGDLFSVAWLEDSDVQNSWYETLNQQYHHVDKRISH
ASHATQYGNLKLGEEGLFVYMGSNPANDNYTSLDGNALTPSSIVVNQRDA
DLLHLWEKFRKAPEGSARKEEAQTQIFKAMSHRVHIDSSIKLIGKLLFGI
EKCTEILNAVRPAGQPLVDDWACLRSLVGTFETHCGSLSEYGMRHTRTIA
NICNAGISEEQMAEAASQACASIP

4. SEQ ID NO:4
Common Name: AEP1 from *Clitoria ternatea*, Butelase1
Source: *Clitoria ternatea*
Sequence:

IRDDFLRLPSQASKFFQADDNVEGTRWAVLVAGSKGYVNYRHQADVCHAY
QILKKGGLKDENIIVFMYDDIAYNESNPHPGVIINHPYGSDVYKGVPKDY
VGEDINPPNFYAVLLANKSALTGTGSGKVLDSGPNDHVFIYYTDHGGAGV
LGMPSKPYIAASDLNDVLKKKHASGTYKSIVFYVESCESGSMFDGLLPED
HNIYVMGASDTGESSWVTYCPLQHPSPPPEYDVCVGDLFSVAWLEDCDVH
NLQTETFQQQYEVVKNKTIVALIEDGTHVVQYGDVGLSKQTLFVYMGTDP
ANDNNTFTDKNSLGTPRKAVSQRDADLIHYWEKYRRAPEGSSRKAEAKKQ
LREVMAHRMHIDNSVKHIGKLLFGIEKGHKMLNNVRPAGLPVVDDWDCFK
TLIRTFETHCGSLSEYGMKHMRSFANLCNAGIRKEQMAEASAQACVSIPD
NPWSSLHAGFSV

5. SEQ ID NO:5
Common Name: uncharacterized AEP from coffee [CDP08231.1]
Source: *Coffea canephora*
Sequence:

MMRYATAALLLLALSIIAVAEARDNFLKLPSEIADFFHPKERSDAGGDSV
GTRWAVLIAGSNGYWNYRHQADVCHAYQILKRGGLKDENIVVFMYDDIAY
NEENPRPGVIINSPHGADVYQGVPKDYTGDDVNAKNFLAAILGDKTAITG
GSGKVVDSGPNDHIFIYYTDHGGPGVLGTPSGPYLYADDLNEVLKKKHAS
GTYKSLVFYLEACESGSIFEGLLPEDLNIYATTASNAEESSWGTYCPGEY
PSPPPEYETCLGDLYSVAWMEDSEIHNLHTETLKQQYHLVKKRTSSSNSA
YGSHVMQYGDLKLSLEDLFLYMGTNPANDNYTFVDENSLRPSSKAVNQRD
ADLLHFWDKFRKAPEGSARKVEAQKQVVEAMSHRMHIDNSVKLIGKLLFG
IEKGSEILNSVRPAGHPLADDWDCLKSLVRTFETHCGSLSQYGMKHMRSI
ANICNAGIKKDQMAEAAAQACVSLPSNSWSSLHRGFSA

6. SEQ ID NO:6
Common Name: uncharacterized enzyme [XP_017229093.1]
Source: *Daucus carota* subsp. sativus
Sequence:

MVRYLAGAVALLVVVSISAVVESRRDIVGDVLKLPSEVSSFFRPVAEEED

SVGTRWAVLIAGSNGYWNYRHQADICHAYQLLRRGGVKEENIVVFMYDDI

AYDEENPRPGVIINSPHGSDVYKGVPKDYTGEDVTVNNVFAAILGDKSAT

TGGSGKVVDSGPNDHIFIYYSDHGGPGVLGMPTNPYMYAGDLVDVLKKKH

ASGTYKSMVFYLEACESGSIFEGLLPEGLNIYATTASNAYESSWGTYCPG

EYPSPPPEYETCLGDLYSVAWMEDSDIHNLRTETLRQQYQQVKKRTSNDN

SGWGSHVMQYGDLKLSTEELFMYMGTNPANDNFTFVDDNSLRLSSSKAVN

QRDADLLHFWDKYRKAPEGSDRKIAAQKQFSEAMSHRMHLDNSIQLIGKL

LFGIDTASEVLTTVRPSGQPLVDDWLCLKKLVRTFETYCGSLSQYGMKHM

RSIANICNAGISEEQMSEASAQACVTFPSNPWSSVNKGFTA

7. SEQ ID NO:7
Common Name: Peptidase C13, legumain [OMO66906.1]
Source: *Corchorus capsularis*
Sequence:

MTRLVAGVILLLLSVTGIVSAGRDATGDVLRLPSEASRFFRPSDDDEVGT

RWAVLIAGSNGYWNYRHQADVCHAYQLLKKGGLKDENIIVFMYDDIAYNY

ENPRQGIIINSPHGDDVYQGVPKDYTGEEVTVHNFLAAILGNKTAITGGS

GKVVDSGPNDHIFIYYTDHGGPGVLGMPTYPYLYADELIDTLKKKHASGT

YKSLVFYLEACESGSIFEGLLPEGLNIYATTASNADESSWGTYCPGEYPS

PPPEYETCLGDLYSVAWMEDSDLHNLRTETLHQQYELVKRRTLNGNSAYG

SHVMQYGDVGLAKEHLFLYLGTNPANDNFTFIDENSLQPPAKAVNQRDAD

LVHFWDKYRKAPDGSARKVEAQKQVVEAMSHRMHVDNSIQLIGKLLFGIE

RGADVLKTVRPAGQPLVDDWKCLKSMVRTFETHCGSLAQYGMKHMRSIAN

ICNAGIQTEQIAEASAQACVSIPSGQWSSIQKGFSA

8. SEQ ID NO:8
Common Name: Peptidase C13, legumain [OMO86616.1]
Source: *Corchorus olitorius*
Sequence:

MTRLVAGVILLLLSVTGIASAGRDATGDVLRLPSEASRFFRPSDDDEVGT

RWAVLIAGSNGYWNYRHQADVCHAYQLLKKGGLKDENIIVFMYDDIAFNY

ENPRQGIIINSPHGDDVYQDVPKDYTGEEVTVHNFLAAILGNKTAIKGGS

GKVVDSGPNDHIFIYYTDHGGPGVLGMPTYPYLYADELIDTLKKKHASGT

YKSLVFYLEACESGSIFEGLLPEGLNIYATTASNADESSWGTYCPGEYPS

PPPEYETCLGDLYSVAWMEDSDLHNLRTETLHQQYELVKRRTLNGNSAYG

SHVMQYGDVGLAKEHLFLYLGTNPANDNFTFIDENSLQPPAKAVNQRDAD

LVHFWDKYRKAPDGSVRKVEAQKQVVEAMSHRMHVDNSIQLIGKLLFGIE

RGADVLKTVRPAGQPLVDDWKCLKSMVRTFETHCGSLAQYGMKHMRSIAN

ICNAGIQTEQMAEASSQACVSIPSGQWSSIQKGFSA

9. SEQ ID NO:9
Common Name: vacuolar-processing enzyme [XP_012077326.1]
Source: *Jatropha curcas*
Sequence:

MTRLATGVILLLLALCVVSSAGSRDIVGDVLRLPSEASRFFRPGGAHVAK

EDDSTGTRWAILIAGSNGYWNYRHQADVCHAYQLLKKGGLKDENIIVFMY

DDIAFNKENPRPGVIINNPYGEDVYKGVPKDYTGEDVNVNNFFAAILGNK

TAITGGSGKVVDSGPNDHIFIYYTDHGGPGVLGMPTNPYLYANDLIDVLI

KKHASGTYKSLVFYLEACESGSIFEGLLPEGLNIYATTAANAEESSWGTY

CPGEYPSPPPEYETCLGDLYSVAWMEDSDVHNLQTETLRQQYQLVKRRTA

NGNSAYGSHVMQYGDVGLSKDNLFLYMGTNPANENYTFVDENSLRPPSKA

VNQRDADLVHFWDKYRKAPDGSTRKIQAQKQFVEAMSHRMHLDHSMKLIG

KLLFGIGKGSEVLNAIRPAGQPLVDDWVCLKTLVRTFETHCGSLSQYGMK

HMRSLANLCNAGIREDQMAEASAQACVSIPSGPWSSLHKGFSA

10. SEQ ID NO:10
Common Name: uncharacterized enzyme [AGC94758.1]
Source: *Malus hupehensis*
Sequence:

MTRLASAVVLLFLASVLASAAGSRDLIGDVLRLPSEASRFFGRGDDAPDQ

QDDGTVGTRWAVLIAGSNGYWNYRHQADICHAYQLLKKGGLKDENIVVFM

YDDIAYNEENPRQGVIINSPHGSDVYEGVPKDYTGEDVTVNNFFAAILGN

KTALTGGSGKVVDSGPNDHIFIYYTDHGGPGILGMPTSPYIYANDLIEVL

KKKHAAGTYRSLVFYLEACESGSIFEGLLPEGLNIFATTASNAEESSWGT

YCPGEYPSPPPEYDTCLGDLYSVAWMEDSDVHNLRSETLHQQYELVKTRA

ANDNSGSGSHVMQYGDVGLSKNNLFVYMGTNPANDNYTFLGENSLRPSSK

AVNQRDADLLHFWHKYRKAPEGSARKIQAQKDFVEAMSHRMHIDQTMKLI

GKLLFGIEKGPQVLNAVRPAGQPLVDDWDCLKTMVRSFETHCGSLSQYGM

KHMRSLANICNAGMTQEQMAEASAQACVSAPSGRWSSLHRGFSA

11. SEQ ID NO:11
Common Name: vacuolar-processing enzyme-like [XP_009361606.1]
Source: *Pyrus x bretschneideri*
Sequence:

MTRFAGAVVLLFLASVLASAAGSRDLIGDVLRLPSEASRFFGRGDDAPDQ

QDDGTVGTRWAVLIAGSNGYWNYRHQADICHAYQLLKKGGLKDENIVVFM

YDDIAYNEENPRQGVIINNPQGSDVYEGVPKDYTGEDVTVNNFFAAILGN

KTALTGGSGKVVDSGPNDHIFIYYTDHGGPGVLGMPTSPYIYANDLIEVL

KKKHAAGTYKSLVFYLEACESGSIFEGLLPEGLNIFATTASNAEESSWGT

YCPGEYPSPPPEYETCLGDLYSVAWMEDSDIHNLRSETLHQQYELVKTRT

-continued

ANDNYGFGSHVMQYGDVGLSKNNLFVYMGTNPANDNYTFLGENSLRPSSK

AVNQRDADLLHFWHKYRKAPEGSARKVQAQKDFVEAMSHRMHIDQTMKLI

GKLLFGIEKGPQVLNAVRPAGQPLVDDWDCLKTMVRSFETHCGSLSQYGM

KHMRSLANICNAGMTQEQMAEASAQACVSAPSSRWSSLHRGFSA

12. SEQ ID NO:12

Common Name: wild type OaAEP1 (SEQ ID NO:3) Construct for recombinant expression Sequence:

MGMAHHHHHHMQIFVKTLTGKTITLEVEPSDTIENVKAKIQDKEGIPPDQ

QRLIFAGKQLEDGRTLSDYNIQKESTLHLVLRLRGGARDGDYLHLPSEVS

RFFRPQETNDDHGEDSVGTRWAVLIAGSKGYANYRHQAGVCHAYQILKRG

GLKDENIVVFMYDDIAYNESNPRPGVIINSPHGSDVYAGVPKDYTGEEVN

AKNFLAAILGNKSAITGGSGKVVDSGPNDHIFIYYTDHGAAGVIGMPSKP

YLYADELNDALKKKHASGTYKSLVFYLEACESGSMFEGILPEDLNIYALT

STNTTESSWCYYCPAQENPPPPEYNVCLGDLFSVAWLEDSDVQNSWYETL

NQQYHHVDKRISHASHATQYGNLKLGEEGLFVYMGSNPANDNYTSLDGNA

LTPSSIVVNQRDADLLHLWEKFRKAPEGSARKEEAQTQIFKAMSHRVHID

SSIKLIGKLLFGIEKCTEILNAVRPAGQPLVDDWACLRSLVGTFETHCGS

LSEYGMRHTRTIANICNAGISEEQMAEAASQACASIP

13. SEQ ID NO:13

Common Name: Hexa-His tag (recombinant)

Sequence:

MGMAHHHHHH

14. SEQ ID NO:14

Common Name: Ubiquitin tag for assisting recombinant protein expression (recombinant)

Sequence:

MQIFVKILTGKTITLEVEPSDTIENVKAKIQDKEGIPPDQQRLIFAGKQL

EDGRTLSDYNIQKESTLHLVLRLRGG

15. SEQ ID NO:15

Common Name: pre-activation form of wild type OaAEP1 (construct being crystalized in this application, PDB code: 5H0I)

Sequence:

ARGDYLHLPSEVSRFFRPQETNDDHGEDSVGTRWAVLIAGSKGYANYRHQ

AGVCHAYQILKRGGLKDENIVVFMYDDIAYNESNPRPGVIINSPHGSDVY

AGVPKDYTGEEVNAKNFLAAILGNKSAITGGSGKVVDSGPNDHIFIYYTD

HGAAGVIGMPSKPYLYADELNDALKKKHASGTYKSLVFYLEACESGSMFE

GILPEDLNIYALTSTNTTESSWCYYCPAQENPPPPEYNVCLGDLFSVAWL

EDSDVQNSWYETLNQQYHHVDKRISHASHATQYGNLKLGEEGLFVYMGSN

PANDNYTSLDGNALTPSSIVVNQRDADLLHLWEKFRKAPEGSARKEEAQT

QIFKAMSHRVHIDSSIKLIGKLLFGIEKCTEILNAVRPAGQPLVDDWACL

RSLVGTFETHCGSLSEYGMRHTRTIANICNAGISEEQMAEAASQACASIP

16. SEQ ID NO:16

Common Name: AEP-C247A-Mut, primer used for mutagenesis, converting Seq ID NO:3 to Seq ID NO:1.

Sequence:

CACCACCGAAAGCAGCTGGGCCTACTATTGCCCGGCGC

17. SEQ ID NO:17

Common Name: Peptide template used for characterizing recognition sequence specificity of Quicklase Sequence:

$Xaa^1Xaa^2YRRGRLYRRNXaa^3Xaa^4$

* In each screen, only one of the residue is modified, and the default amino acid at $Xaa^1$ position is Gly, at $Xaa^2$ position is Leu, and at $Xaa^3$ position is Gly, and at the $Xaa^4$ position is Leu, in this screen.

Example 1: Quicklase OaAEP1 Mediates Peptide Ligation

AEP-like plant peptide ligases share a conserved protein architecture also found in human legumain endopeptidase (hlegum) (Ishii, S., Methods Enzymol, 1994. 244: p. 604-15; Chen, J. M., et al., J Biol Chem, 1997. 272(12): p. 8090-8). Plant AEPs have an N-terminal signal sequence of ~20-30 amino acids that direct them to the plant vacuolar compartment, followed by an enzymatic core domain. At the C-terminus of the core domain, a ~130-residues "cap" or pro-domain entirely covers the active site, keeping the immature protein in an inactive zymogenic state. The core and pro-domain are connected by a "linker" defined as spanning residues 325-346 of the protein (FIG. 2A). Activation of plant AEP enzymatic activities requires proteolytic maturation at an acidic pH of about 3.7, at which the pro-domain is cleaved either in cis by the proteolytic activity of the core domain itself or in trans by activated Asx proteases present in the milieu, and released from the core domain. The precise cleavage site(s) within the linker and pro-domain, leading to the formation of a mature active plant AEP ligase remain poorly characterized. In the case of butelase 1, Asn383 was hypothesized to constitute the site of cap domain cleavage (Nguyen, G. K., et al., Nat Chem Biol, 2014. 10(9): p. 732-8), while several potential cleavage sites spanning region 328-351 of the protein were proposed for OaAEP1 (FIG. 2A and FIG. 7) (Harris, K. S., et al., Nat Commun, 2015. 6: p. 10199). Amino-acid sequence alignments of plant AEP-like ligases with AEP peptidases such as hlegum also reveal the presence of several evolutionary conserved residues in the catalytic pocket (FIG. 7) (Nguyen, G. K., et al., Nat Chem Biol, 2014. 10(9): p. 732-8; Harris, K. S., et al., Nat Commun, 2015. 6: p. 10199; Dall, E., et al., Angew Chem Int Ed Engl, 2015. 54(10): p. 2917-21; Dall, E. and H. Brandstetter, Biochimie, 2016. 122: p. 126-50; Saska, I., et al., J Biol Chem, 2007. 282(40): p. 29721-8). Therefore, what determines how these closely similar enzymes preferentially function either as ligase or protease remains elusive. Herein reported is a crystal structure of OaAEP1 in its zymogenic form revealing how the amide group of Gln347 a residue at the N-terminus of the pro-domain can be accommodated in the catalytic pocket. Based on the OaAEP1 structure, a series of OaAEP1 mutants was generated to better understand the activation mechanism and catalytic activities of plant AEP ligases. It was found that that the segment 346-351 plays a critical role for the maturation of OaAEP1b, because mutating Asx residues within this segment severely disrupts AEP ligase activation. A major determinant governing the efficiency of peptide ligation activities of OaAEP1 is the side chain at residue 247, which is located near the catalytic Cys217-His175 dyad: larger side-chains at this position completely abolish ligase enzymatic activities, while smaller side-chains allow ligation reactions to take place at a much faster rate. Accordingly, it was demonstrated that the single Cys247Ala mutant of OaAEP1 has peptide ligase catalytic activity ~160 times faster than the wild type OaAEP1 enzyme, comparable to the butelase 1 enzyme extracted from plant. It was also shown that Cys247Ala can efficiently catalyze the ligation of two well-folded proteins: ubiquitin and SNAP tag protein, using only sub-micro molar concentrations of the recombinant enzyme.

Figure 1:
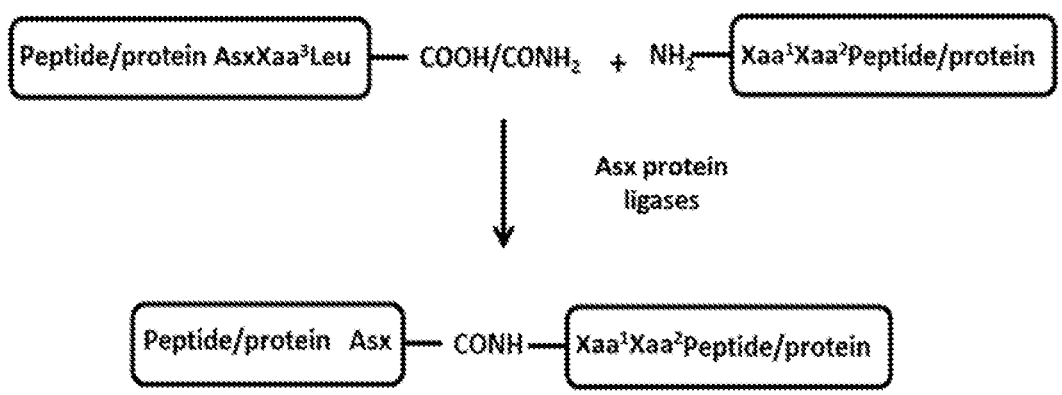
FIG. 1 shows a schematic illustration of (a) OaAEP1 Cys247Ala (SEQ ID NO:1)-mediated peptide ligation and (b) a preferred embodiment thereof.
Figure 1:
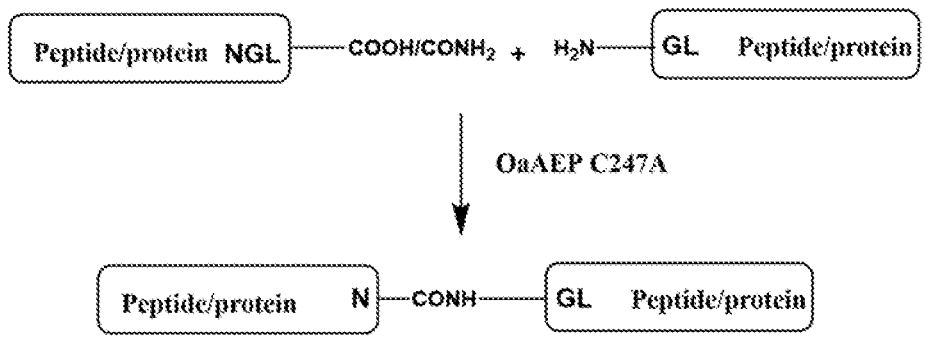
Figure 2:
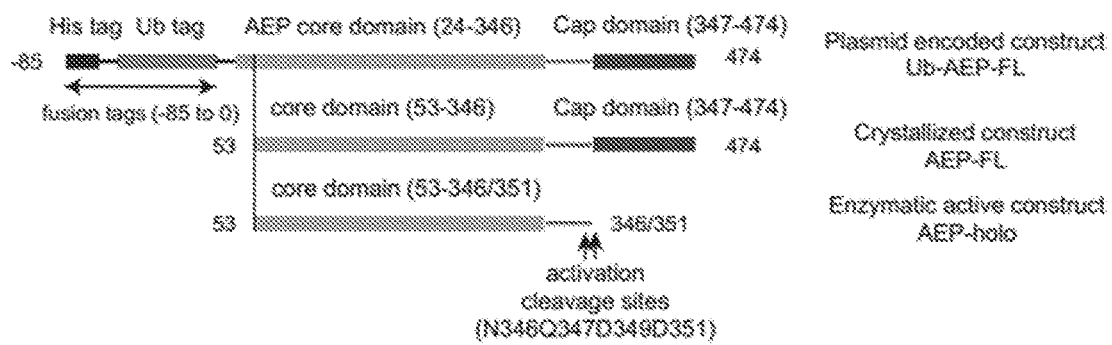
FIG. 2 shows purification and activation of OaAEP1b. (a) Schematic illustration of the His-Ub-OaAEP1 construct used with the boundaries of the three regions of the protein indicated and the deduced activation segment. 6-His tag and Ubiquitin tag followed by OaAEP1 (24-474) was synthesized and inserted into pET28b vector. After Ni-NTA affinity purification, about half of Ub-AEP-FL lost the N-terminal fusion tags and was purified in AEP-FL form (53-474), which was eventually crystallized. The enzymatic active form of OaAEP1b, AEP-holo (53-347/351) is the acidic induced self-cleavage product of AEP-FL, which lost the C-terminal auto inhibitory cap domain. (b) SDS PAGE analysis of fractions obtained over the course of chromatographic purification and of dissolved crystals. (c) Size-exclusion chromatography profiles of OaAEP1 before and after activation showing Ub-AEP-FL and AEP-FL heterodimer and the AEP-holo monomer. The elution volumes of standard proteins are indicated for comparison. (d) SDS PAGE analysis of OaAEP1 pH-dependent activation. The activation was performed for 3 hours, and the peak of activation is in between pH 3.4 to 4. (e) Trans activation/maturation of the inactive Cys217Ser active site mutant by the active recombinant mature OaAEP1 enzyme. The active site Cys217Ala mutant is devoid of self-activation activity. Addition of 5% AEP-FL wt enable trans-cleavage and activation of most of the AEP-FL Cys217Ala after 18 hours incubation at pH 3.7.
Figure 2:
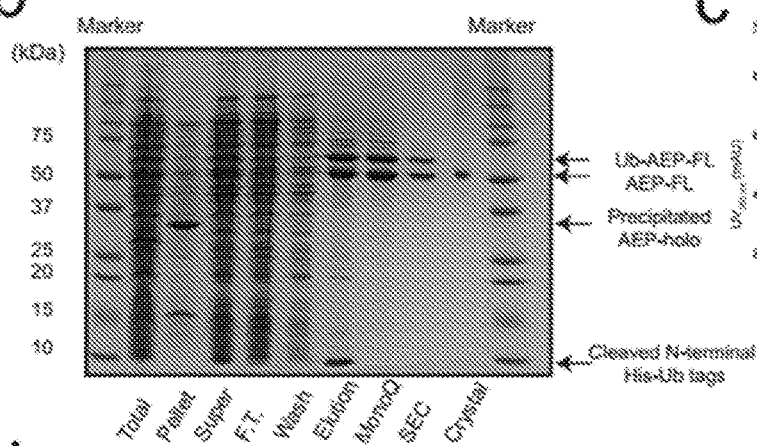
Figure 2:
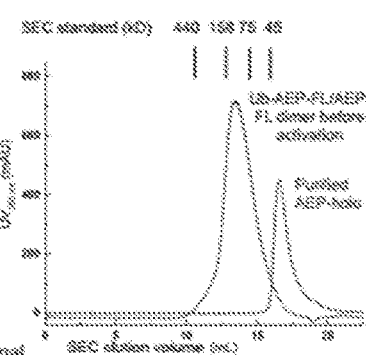
Figure 2:
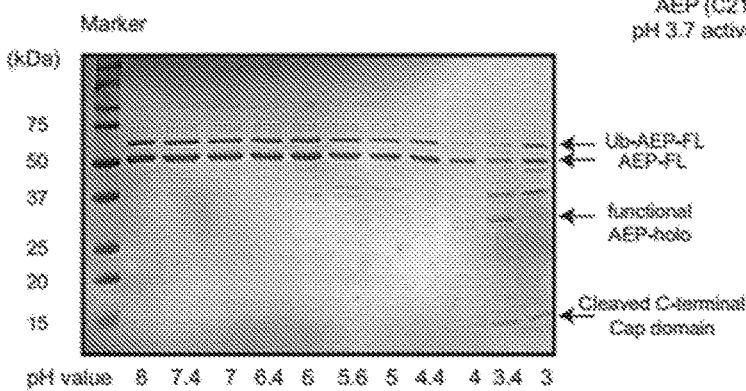
Figure 2:
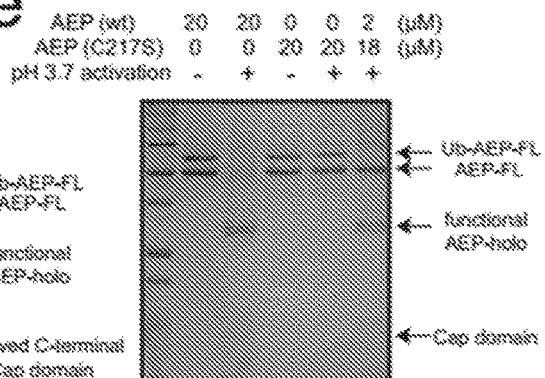

In more detail:

OaAEP1 was cloned and expressed in E. coli as an ubiquitin fusion protein as reported earlier (FIG. 2) (Harris, K. S., et al., Nat Commun, 2015. 6: p. 10199). Using ion exchange and size exclusion chromatography (SEC), sufficient amounts of pure protein suitable for enzymatic and structural analysis were obtained (FIG. 2B). At the neutral pH of purification (pH=7.4), OaAEP1 was mainly present as a heterodimer, where both monomers are in their zymogenic form, but only one monomer had retained in addition the ubiquitin and N-terminal His-tag, while the fusion moiety was cleaved in the other monomer (labeled as "His-Ub-AEP-FL" and "AEP-FL" in FIG. 2B and FIG. 2C). This heterodimer was subjected to crystallization trials for structural studies (see below). In agreement with reference (Harris, K. S., et al., Nat Commun, 2015. 6: p. 10199), activation of OaAEP1 was optimum for pH values in the range of 3.4-4.0 (FIG. 2D). Following activation, OaAEP1 converts to a monomer in solution according to SEC analysis ("AEP-holo" in FIG. 2C). To test the ability of the protein to be activated in trans, the catalytic residue Cys217 was mutated into Ser217. As anticipated, the Cys217Ser mutant only displayed background level activation and ligase activity (FIG. 2E). However, activation of the inactive mutant could be rescued in trans by addition of only 10% of wild type OaAEP1 to the inactive enzyme (FIG. 2E). This suggested that similar trans-cleavage processing events could also be at play during OaAEP1 activation and that Cys217 is the active site residue for both cis and trans-activation.

Figure 3:
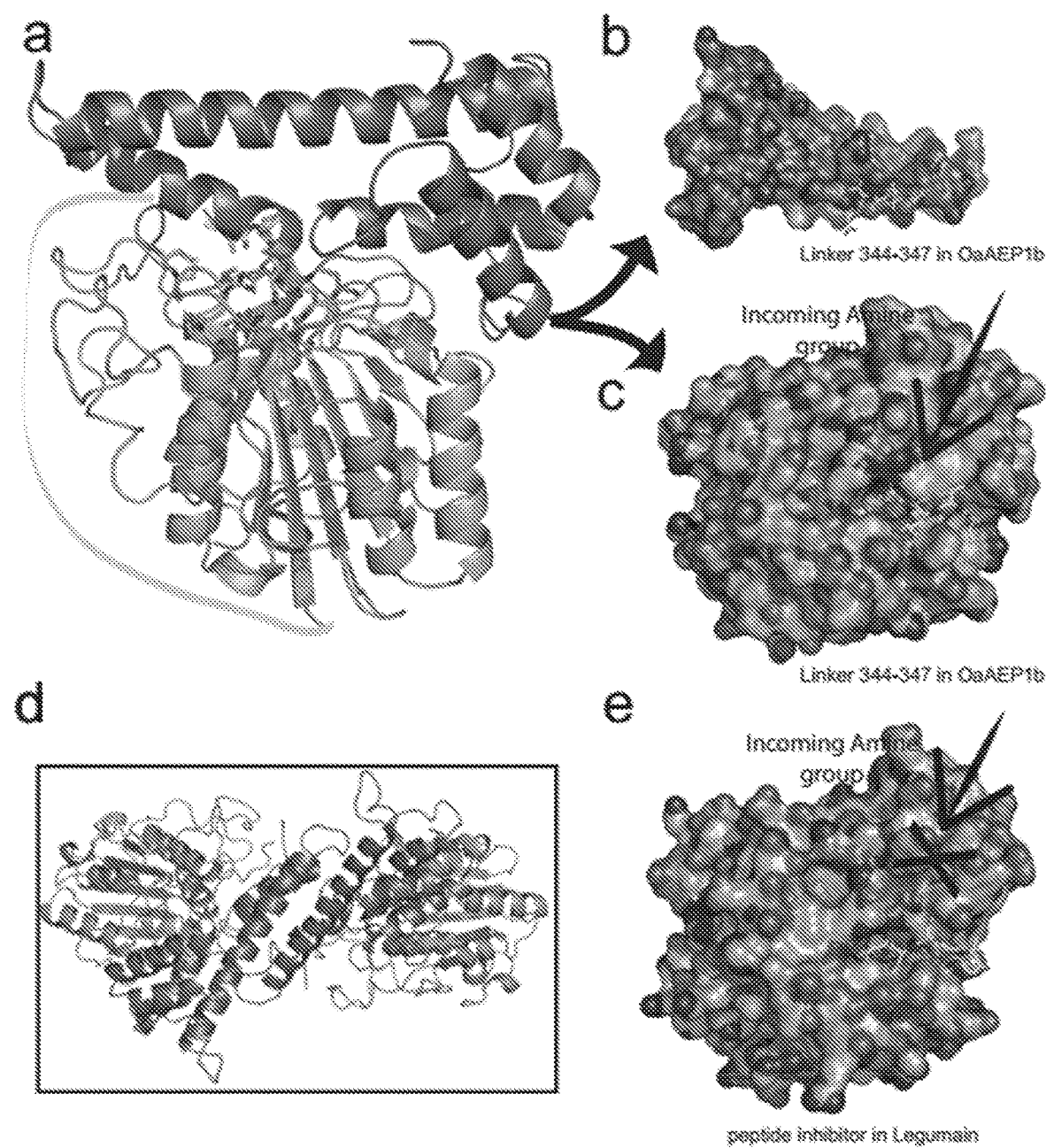
Figure 3F:
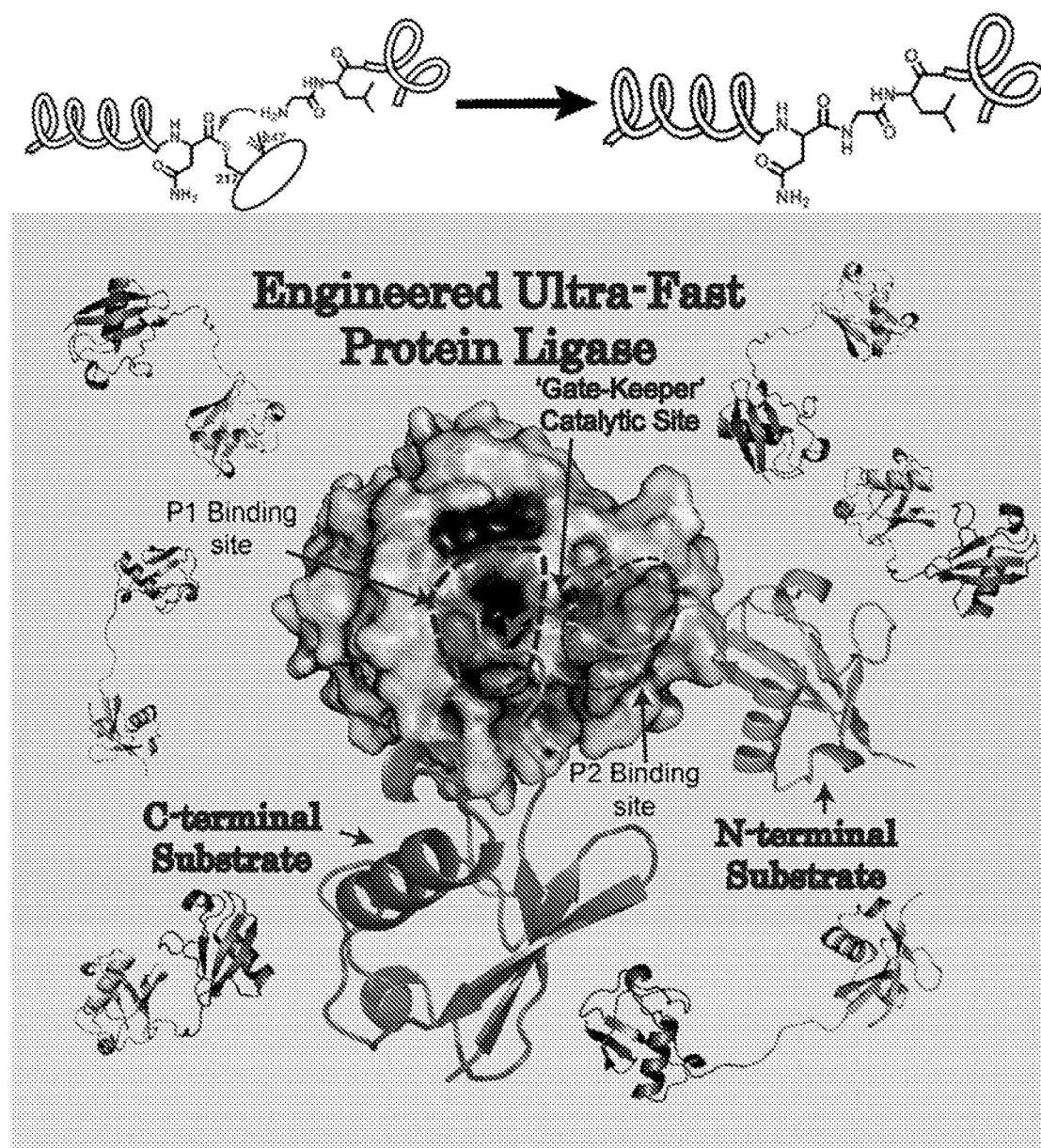

Crystals of OaAEP1 diffracting to a resolution of 2.56 Å at a $3^{rd}$ generation synchrotron source were obtained (Table 1 and FIG. 3). Although a OaAEP1 heterodimer was used as starting material, the crystal structure revealed a homodimer where both N-terminal $(His)_6$ tag and Ubiquitin fusion protein as well as the signal peptide sequence had been released from the two monomers present in the asymmetric unit, suggesting N-terminal proteolysis during crystallization (FIGS. 3A and D). The OaAEP1 dimer is stabilized by intermolecular interactions between the two cap domains (FIG. 3D). This is in agreement with SEC analysis (FIG. 2C) showing that the pre-activated form of the enzyme containing the cap region is dimeric at neutral pH, while the activated form, which is devoid of cap, is monomeric. Accordingly, SDS PAGE of dissolved OaAEP1 crystals (FIG. 2B) revealed the presence of both the enzymatic core and the C-terminal pro-domain with a total Mr of approximately 49.7 kDa, supporting the hypothesis that the crystallized enzyme is in an immature form. The OaAEP1 core is formed by a 6-stranded β-sheet surrounded by six α-helices at its periphery (Dail, E., et al., Angew Chem Int Ed Engl, 2015. 54(10): p. 2917-21; Dall, E. and H. Brandstetter, Proc Natl Acad Sci USA, 2013. 110(27): p. 10940-5; Zhao, L., et al., Cell Res, 2014. 24(3): p. 344-58). An overall view of the structure shown in FIG. 3A reveals that the α-helical cap domain (spanning residues 347-474) entirely covers the catalytic cleft and suggests that release of the cap is required to grant access to peptide or protein substrates. The OaAEP1 catalytic site contains several residues present in other AEPs including the Cys217-His175 catalytic dyad (Cys189-His148 in hlegum) and His73-Asp174 that superimpose with His45-Asp147 of hlegum bound to cystatin E (PDB code 4N60) (FIG. 4). A clear difference captured here between the zymogenic forms of hlegum (PDB code: 4NOK) and OaAEP1 resides within the linker region: in the case of the prolegumain structure, the linker is short and well ordered, whilst it is long and flexible in the present OaAEP1 structure (FIG. 3A): no electron density was present for the 19 residues between 325 to 343, although this segment is present in the crystallized protein (FIG. 2B).

TABLE 1

Data collection and refinement statistics

| | oAEP1b |
|---|---|
| Resolution range (Å) | 71.72-2.56 (2.70-2.56)* |
| Space group | C 2 |
| Unit cell dimensions a, b, c (Å) | 145.73 70.21 118.28 |
| Angles α, β, γ (°) | 90 117.14 90 |
| Measured reflections | 104,721 (14,189) |
| Unique reflections | 34,420 (5,029) |
| Multiplicity | 3.0 (2.8) |
| Completeness (%) | 99.7 (99.6) |
| Mean I/sigma(I) | 7.0 (1.7) |
| $R_{merge}^a$ | 0.095 (0.700) |
| $R_{pim}^b$ | 0.065 (0.501) |
| $R_{work}^c$ | 0.186 (0.212) |
| $R_{free}^d$ | 0.221 (0.212) |
| Number of non-hydrogen atoms | 6,498 |
| macromolecules | 6,200 |
| water | 298 |
| Protein residues | 851 |
| RMS (bonds, Å) | 0.010 |
| RMS (angles, °) | 1.19 |
| Ramachandran plot (%) | |
| favoured | 93.8 |
| allowed | 5.1 |
| outliers | 1.1 |
| Clash score | 6.37 |
| Average B-factor | |
| Monomer A, B | 71.8, 66.1 |
| solvent | 62.0 |

*The numbers in parentheses refer to the last (highest) resolution shell.

$^a R_{merge} = \Sigma |I_j - <I>|/\Sigma I_j$, where $I_j$ is the intensity of an individual reflection, and $<I>$ is the average intensity of that reflection.

$$^b R_{pim} = \frac{\sum_{hkl} \sqrt{\frac{1}{n-1} \sum_{j=1}^{n} |I_{hkl,j} - \langle I_{hkl}\rangle|}}{\sum_{hkl} \sum_j I_{hkl,j}}$$

$^c R_{work} = \Sigma ||F_o| - |F_c||/\Sigma |F_c|$, where $F_o$ denotes the observed structure factor amplitude, and $F_c$ the structure factor amplitude calculated from the model.
$^d R_{free}$ is as for $R_{work}$ but calculated with 5% (3044) of randomly chosen reflections omitted from the refinement.

While residues 325-343 of the linker region are not visible in the electron density map due to their flexibility, residues Val344-Val345-Asn346-Gln347 are trapped at the interface between the cap and the core domain (FIGS. 3C and 4A). Remarkably, their orientation closely overlaps with the Ac-Tyr-Val-Ala-Asp-chloromethylketone inhibitor that was covalently linked to the catalytic Cys189 of hlegum (FIG.

3E, PDB code: 4AWA) (Dail, E. and H. Brandstetter, Proc Natl Acad Sci USA, 2013. 110(27): p. 10940-5). Here however, residue Gln347 penetrates deeply into the S1 pocket such that its amide group occupies the position of the carboxylic group of the Asp residue in the Ac-Tyr-Val-Ala-Asp-CMK protease inhibitor that was covalently bound to hlegum and forming several interactions with the surrounding active site residues (FIGS. 4A and 4B). Thus the present crystal structure can serve as a useful model to picture a pre-ligation conformation, with linker residues 344-347 mimicking a N-terminal substrate acceptor bound to the active site.

Although in other AEPs, Asx is the most favored residue for processing at the P1 position, the carbonyl group of Gln347 lies at a distance of 5.2 Å from the attacking Cys217 sulfur center, suggesting that the segment 346-351 of the pro-protein might contain auto-cleavage sites used during maturation. Since the crystallization conditions are compatible with OaAEP1 activation, the present crystal structure is likely to have captured one of the conformational states occurring along the activation pathway. To determine whether Gln347 belongs to the segment recognized and cleaved during self-activation, mutagenesis experiments targeting region 346-351 of the OaAEP1 protein were performed (FIG. 4C). The role of Gln347 in OaAEP1 auto-activation was particularly assessed by mutating this residue to Ala, and whether enzyme activation was abolished was examined. Only little impact was found on the mutant enzyme activation (FIG. 4C). Residues Asn346, Asp349 and Asp351 that are next to Gln347 were then targeted. While the two OaAEP1 double mutants Asn346Ala-Gln347Ala and Asp349Ala-Asp351Ala and the Asn346Ala-Asp349Ala-Asp351Ala triple mutant can still be activated, the Asn346Ala-Gln347Ala-Asp349Ala-Asp351Ala had the most significantly impaired auto-activation activity (lane "A4" in FIG. 4C). Importantly, activation of the four-Ala mutant could not be rescued in trans when wild type enzyme was added to the reaction mixture. Thus, trans-activation requires the presence of at least one of the four Asx/Gln residues (with a slight preference for Asp349 or Asp351) found in this segment of the linker. Taken together, these data suggest that the present crystal structure represents an intermediate conformational state during which the linker region is trapped at the catalytic site, mimicking a substrate-bound pre-ligation complex.

The peptide cyclization activity of mature OaAEP1 was then analyzed using MS and the peptide substrate "GLPVSTKPVATRNGL" (SEQ ID NO: 18) (FIG. 5A). The turn-over rate ($k_{cat}$) for OaAEP1 is 0.052 s$^{-1}$, a value in good agreement with the previous report (Harris, K. S., et al., Nat Commun, 2015. 6: p. 10199). Likewise, the cyclization activity of butelase 1 extracted from plant was measured using the 15 residues peptide "GLPVSTKPVATRNHV" (SEQ ID NO: 19) (FIG. 5A) leading to a $k_{cat}$ about 90 times faster than OaAEP1 b.

The pre-ligation conformation of OaAEP1 captured in the present structure was then analyzed to identify several key features that could differentiate an AEP protease from an AEP-like ligase. A side-by-side comparison with a previously reported proteolytic AEP-inhibitor complex (PDB code: 4AWA) revealed interesting structural features unique to AEP-like ligases. In contrast to AEP proteases, the surface of OaAEP1 facing the catalytic Cys217 appears to be more widely open. Three cysteine residues (Cys247, Cys250, Cys264) are aligned along a shallow cleft at the surface of the enzyme (FIGS. 3C and 3E). Unlike the surface of AEP proteases that contains several bulges, both butelase 1 (using a homology model based on OaAEP1b) and OaAEP1 have residues with smaller side-chains along this patch. A disulfide bond is formed between Cys250 and Cys264, which are conserved in AEP-like ligases butelase 1 and OaAEP1b. This covalent bond is likely to stabilize the local structure and provide an adequate surface allowing the approach of an N-terminal amine incoming group. Conversely, the corresponding surface patch of AEP proteases (PDB: 4AWA) is lined with residues having bulky side-chains like Tyr (FIG. 3E) blocking this channel. It was therefore hypothesized that residue Cys247 which is located at the extremity of the substrate channel is likely to function as a final nucleophile filter (or "gate-keeper"), allowing attack from the N-terminal amine to complete the ligation reaction. To test the impact of various side chains on ligase behavior at the "gate keeper" position, a series of point mutagenesis was performed whereby Cys247 was mutated into Gly, Ala, Val, Ser, Thr, Met, Leu and Ile (FIG. 5). The activity of the corresponding mutant proteins revealed that the size of the side chain indeed plays a critical role on ligase activity. Remarkably, the Cys247Ala mutant displayed significantly improved enzymatic properties compared to WT OaAEP1 (FIG. 5D). This phenotype was attribute to the presence of a smaller side chain that is more appropriate to accommodate an incoming amine group, while the Cys247Gly mutation destabilizes the local conformation and negatively affects the ligase activity. Further investigations showed that Cys247Gly catalyzes peptide hydrolysis as alternative reaction, if the available N-terminal amine group was acetylated (FIG. 10). While in the case of Cys247Ala mutant, side chain ligation is more preferred if no available N-terminal amine is present, Ala is less hydrophilic which disfavors water entering the catalytic patch causing hydrolysis of the intermediate thio-ester bond. When the N-terminal amine is not protected, backbone ligation is much more favored than any of the alternative reactions.

Remarkably Cys247Ala demonstrated improved enzymatic properties over the parent wild-type OaAEP1 protein: its $k_{cat}$ approximately 160 times higher than WT OaAEP1b, makes it an attractive tool for a variety of challenging protein engineering and labeling applications. The ability of Cys247Ala to ligate ubiquitin with a peptide was first tested. The three residues"Asn-Gly-Leu" were added to the C-terminus of ubiquitin to make it recognizable by Cys247Ala. Another peptide having N-terminal residues GlyLeu was used as the add-on component. At a protein: peptide molar ratio of 1:5, Cys247Ala catalyzed the ligation of more than 90% ubiquitin with the peptide within 10 min (FIG. 6). An amount of 30 nM of Cys247Ala was enough for the reaction compared to 10-30 μM of sortase A typically required to perform productive ligations. To further demonstrate the potential of Cys247Ala, ligations between two well-folded proteins were also tested. Ubiquitin having the same "Asn-Gly-Leu" modification at its C-terminal end and a N-terminal modified SNAP (NEB) tag protein were used as substrates. Using 5 μM of SNAP tag protein and 8 μM ubiquitin, 100 nM Cys247Ala was able to ligate more than 60% of the individual substrate proteins into a ligated single polypeptide product, indicating that the catalyzed protein ligation is highly efficient and irreversible (FIG. 6). Protein ligation can be performed within minutes at neutral pH and at room temperature. Remarkably, the efficiency of Cys247Ala to catalyze the ligation of two folded proteins is comparable to its ability to ligate one protein with a peptide, suggesting that its open binding site can accommodate two bulky protein substrates without hindering the ligation process. Control ligation experiments showed that protein ligation activity could only be observed in the presence of the Cys247Ala protein, but not with the OaAEP1 wild type construct (FIG. 6). This further demonstrated the important role played by the gate-keeper residue in regulating access to protein substrate.

Both sortase A and butelase 1 have been used to perform peptide ligations. However, both enzymes suffered from several disadvantages. Sortase A requires $Ca^{2+}$, is slow and recognizes a longer—more flexible—C-terminal sequence (LPXTG). Although through extensive mutagenesis studies, several mutants were identified improving its kinetics, the catalysis was still quite inefficient in ligating two well-folded proteins (Chen, I., B. M. Dorr, and D. R. Liu, Proc Natl Acad Sci USA, 2011. 108(28): p. 11399-404). In contrast, butelase 1 extracted from plant, is extremely efficient and has a shorter recognition amino acids sequence (NHV) (Nguyen, G. K., et al., Nat Chem Biol, 2014. 10(9): p. 732-8). However, optimization and engineering of the recombinant construct of Butelase 1 still remains challenging because of the difficulty to produce an active recombinant enzyme. Here, to the knowledge of the inventors the first X-ray crystallographic structure of OaAEP1 was reported that can serve as a template to understand the family of plant AEP ligases and will facilitate the design of faster protein ligases with alternative substrate specificities. Our structure reveals the mode through which self-cleavage activation is achieved in AEP-like ligases and also points to key residues and structural features accounting for the functional divergence among AEP-like proteins: AEPs that act primarily as proteases lack the flat surface near the catalytic pocket conducive to ligation, while AEP-like proteins that are efficient ligases have a wide and open surface able to accommodate the incoming amine group. These structural observations led us to engineer a modified ligase Cys247Ala with improved biochemical properties, which can efficiently ligate proteins. Given its fast ligation catalytic kinetics, it is believed that the present Cys247Ala recombinant protein ligase can be employed to perform attractive biotechnological applications both for protein/peptide synthesis and specific protein labeling (Guimaraes, C. P., et al., Nat Protoc, 2013. 8(9): p. 1787-99; Swee, L. K., et al., Proc Natl Acad Sci USA, 2013. 110(4): p. 1428-33; Theile, C. S., et al., Nat Protoc, 2013. 8(9): p. 1800-7; Witte, M. D., et al., Nat Protoc, 2013. 8(9): p. 1808-19; Wagner, K., et al., Proc Natl Acad Sci USA, 2014. 111(47): p. 16820-5; Nguyen, G. K., et al., Angew Chem Int Ed Engl, 2015. 54(52): p. 15694-8; Nguyen, G. K., et al., J Am Chem Soc, 2015. 137(49): p. 15398-401).

Example 2: Quicklase OaAEP1 Homologues Identified by NCBI-BLAST

A Blast search of the amino acid sequence of SEQ ID NO:1 was carried out by submitting the sequence to the NCBI blast server using standard blast criteria. Top hits as displayed in FIG. 12 were selected for sequence analysis. All of them were found to contain the conserved structural motif of residues 247-264 of OaAEP1 b.

Example 3: AEP_C13C04 (SEQ ID NO:8) is a Peptide Ligase Having the Activity of OaAEP1 Cys247Ala (SEQ ID NO:1)

Based on the prediction of the sequence alignment, AEP_C13C04 contained the conserved structural motif identical to Quicklase (247-264). This indicated that AEP_C13C04 might be functional protein ligase. The cDNA of AEP_C13C04 was then subsequently synthesized and subcloned into pet28b in a similar way as Quicklase. This new potential ligase was then expressed, purified and activated in the same way as Quicklase, and exhibited both proteolytic and protein ligation activities. Although the wild type of AEP_C13C04 is not an ideal protein ligase, with much slower enzymatic catalytic efficiency as Quicklase, and having significant byproducts of proteolytic reactions (FIG. 13), it appears to a good starting point for further engineering of an alternative protein ligase.

Example 4: QuicklaseOaAEP1-Catalyzed Peptide Dimerization, Oligomerization, and Multimerization In relation to the schemes illustrated in FIG. 14, the following exemplary experiments were carried out:

FIG. 14 (*a*):

The branched 2-mer linker peptide was synthesized based on standard Fmoc-Solid Phase Peptide Synthesis (SPPS) chemistry on Rink Amide MBHA resin (GL Biochem, Shanghai, China). The branch was introduced by incorporation of Fmoc-L-Lys(Fmoc)-OH. After removing of Fmoc groups at both α- and ε-amino groups, the remaining amino acids (GLGG) were introduced according to the standard Fmoc-SPPS procedure.

For one-step homodimerization reaction, 50 μM of C-terminal NGL-tagged Protein of Interest (POI-NGL), Ub-AA-NGL in this case, was reacted with various concentrations of 2-mer linker ranging from 0-200 μM catalyzed by 0.5 μM of AEP at room temperature. The reaction was monitored by SDS-PAGE after 1 h.

FIG. 14(*b*):

For two-step heterodimerization strategy, the first step was the enzyme (0.5 μM) catalyzed reaction between POIA-NGL (50 μM) with excessive amount of 2-mer linker (200 μM) to enable only one branch of the dimer linker was labelled. After reaction, the POIA-linker was isolated by removing 2-mer linker peptide through buffer exchange with 3500 MW cut off concentrator.

For the second ligation step, POIB-NGL (100, 200 μM) was reacted with POIA-linker (50 μM) catalyzed by 0.5 μM of AEP to get the final heterodimer product.

FIG. 14(*c*):

To generate the 4-mer linker, the 2-mer linker was dimerized through crosslinking of the C-terminal cysteine residue. See figure g for the reaction detail.

One-step protein tetramerization was achieved by AEP catalyzed reaction between POI-NGL and the 4-mer linker. With ubiquitin as an example, to optimize the ligation reaction, 20 μM of Ub-AA-NGL (POI-NGL) was ligated with various concentrations (0-80 μM) of 4-mer linker in the presence of 0.5 μM of AEP at pH 7.4, room temperature. After 1 h, the reaction was analyzed by SDS-PAGE, which indicated that maximal amount of Ub-tetramer was yielded when 2.5-5 μM of 4-mer linker was used.

FIG. 14(*d*):

To achieve protein ultra-oligomerization, the oligomer peptide platform was first synthesized via two steps: i) a peptide containing multiple cysteine residues which were separated by flexible spacer of 7-8 amino acids was synthesized directly or through native chemical ligation; ii) the cysteine residues in the peptide was then alkylated by a bromoacetyl peptide with a free N-terminal GL residues for AEP catalyzed ligation later. After producing the oligomer linker, AEP catalyzed reaction between POI-NGL and the oligomer linker was performed to generated the protein ultra-oligomer.

FIG. 14(e, f):

Schemes for the generation of 2-mer-NGL linker used for protein head-to-head dimerization: The synthesis of 2-mer-NGL liner was achieved via S-alkylation of the N-terminal acetylated cysteine residue of the monomer-NGL peptide by either 1,3-dichloroacetone or m-Xylylene dibromide (Sigma-aldrich). Briefly, monomer-NGL peptide was dissolved in a buffer containing 20 mM TrisHCl, 150 mM NaCl, 5 mM TCEP, pH 8.0 at a final concentration of 1 mg/mL. 1 eq. of 1,3-dichloroacetone or m-Xylylene dibromide was added into the solution. After 3 h reaction under dark condition, the desired 2-mer-NGL linker was isolated by HPLC purification with C18-reverse phase column.

FIG. 14(g):

Schemes for the generation of GL-tetramer linker used for protein tail-to-tail tetramerization:

The synthesis of GL-tetramer linker was achieved via S-alkylation of the C-terminal cysteine residue of the GL-dimer linker peptide by either 1,3-dichloroacetone or m-Xylylene dibromide. Briefly, GL-dimer peptide was dissolved in a buffer containing 20 mM TrisHCl, 150 mM NaCl, 5 mM TCEP, pH 8.0 at a final concentration of 1 mg/mL. 1 eq. of 1,3-dichloroacetone or m-Xylylene dibromide was added into the solution. After 3 h reaction under dark condition, the desired GL-tetramer linker was isolated by HPLC purification with C18-reverse phase column.

FIG. 14(h):

Scheme for the generation of NGL-oligomer linker used for protein head-to-head oligomerization: NGL-oligomer linker platform was synthesized via the S-alkylation reaction between a peptide containing multiple cysteine residues which were separated by flexible spacer of 7-8 amino acids and another N-terminal bromoacetyl peptide with C-terminal NGL residues for AEP catalyzed ligation later. For the alkylation reaction, briefly, 1 mg/mL of cysteinyl peptide was reacted with 1.5 mg/mL of bromoacetyl peptide in buffer containing 20 mM Tris.HCl, 150 mM NaCl, 5 mM TCEP, pH 8.0, at room temperature avoid of light. After 2 hours, the desired NGL-oligomer linker was isolated by HPLC purification with C18-reverse phase column.

FIG. 14(i):

Scheme for the generation of GL-oligomer linker used for protein tail-to-tail oligomerization: GL-oligomer linker platform was synthesized via the S-alkylation reaction between a peptide containing multiple cysteine residues which were separated by flexible spacer of 7-8 amino acids and another bromoacetyl peptide (bromoacetyl attached to lysine side chain) with N-terminal GL residues for AEP catalyzed ligation later. For the alkylation reaction, briefly, 1 mg/mL of cysteinyl peptide was reacted with 1.5 mg/mL of bromoacetyl peptide in buffer containing 20 mM Tris.HCl, 150 mM NaCl, 5 mM TCEP, pH 8.0, at room temperature avoid of light. After 2 hours, the desired GL-oligomer linker was isolated by HPLC purification with C18-reverse phase column.

Example 5: QuicklaseOaAEP1-Catalyzed Cell Surface Labeling

In relation to FIG. 15, the following exemplary experiments were carried out:

0.1 to 1 μM of OaAEP1 Cys247Ala was added to cellular culture in standard cell culture conditions. 1-20 μM labeling protein tags were added to the reaction afterwards, and incubated for 30-45 mins at 37° C. and standard culturing condition, before both excess enzymes and labelling tags were washed away. Triple washed cellular fractions were harvested to perform the fluorescent SDS-PAGE analysis to determine the labelling efficiency.

In the case of imaging analysis, the images were acquired using Nikon Ti microscope or equivalent (Nikon) with the laser source X-Cite 120 (Excelitas), or equivalent, and digital camera C11440 (Hamamatsu), or equivalent. The programme with which cells were viewed and photographed was MetaMorph (Molecular Devices) or equivalent. Images were compiled using Image J, or equivalent.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A method of forming a peptide of Formula (1)

$$P^1\text{-Asx-Xaa}^1\text{-Xaa}^2\text{-}P^2 \quad (I),$$

wherein the method comprises:
ligating a first peptide of Formula (II $$P^1\text{-Asx-Xaa}^3\text{-Leu-COOH/CONH}_2 \quad (II)$$

to a second peptide of Formula (III)

$$H_{2N}\text{-Xaa}^1\text{-Xaa}^2\text{-}P^2 \quad (III),$$

wherein $P^1$ and $P^2$ are each independently any peptide, modified or unmodified; wherein Asx is Asp or Asn; wherein $Xaa^1$ is any naturally occurring amino acid; wherein $Xaa^2$ is any naturally occurring amino acid with the exception of Pro; and wherein $Xaa^3$ is any naturally occurring amino acid;
enzymatically cleaving the bond between "Asx" and "$Xaa^3$" in the first peptide of Formula (I); and
ligating the fragment $P^1$-Asx of the first peptide via its C-terminus to the N-terminus of the second peptide of Formula (III) to form a ligated peptide of Formula (1), wherein the enzymatic cleavage between "Asx" and "$Xaa^3$" and the ligation reaction of the fragment $P^1$-Asx are catalyzed by a peptide ligase having the activity of *Oldenlandia affinis* asparaginyl endopeptidase 1 (OaAEP1) Cys247Ala (SEQ ID NO:1) under conditions suitable for said cleavage and ligation reaction, wherein the peptide ligase having the activity of OaAEP1 Cys247Ala (SEQ ID NO:1) comprises or consists of:

(a) the amino acid sequence set forth in SEQ ID NO:1;
(b) an amino acid sequence that shares at least 80% sequence identity with, the amino acid sequence as set forth in SEQ ID NO:1, provided that said peptide ligase comprises the amino acid sequence set forth in SEQ ID NO:2 at the positions corresponding to residues 247-264 of SEQ ID NO:1 and the amino acid at position 247 is alanine:
(c) a functional fragment of (a) or (b) provided that said functional fragment comprises the amino acid sequence set forth in SEQ ID NO: 2 at the positions corresponding to residues 247-264 of SEQ ID NO:1 and the amino acid at position 247 is alanine; or
(d) a polypeptide sequence containing the functional fragment of (c), wherein said peptide ligase is not the wild-type OaAEP1 having the amino acid sequence set forth in SEQ ID NO:3 or butelase 1 having the amino acid sequence set forth in SEQ ID NO: 4.

2. The method of claim 1, wherein one or more of the following are selected from the group consisting of:
   (a) Asx is Asn or Asp;
   (b) Xaa$^1$ is any naturally occurring amino acids;
   (c) Xaa$^2$ is Leu or Ile;
   (d) Xaa$^3$ is selected from the group consisting of His, Ala, Ser, Cys, Asn, Gly, Arg, Met, Lys, Gln, Leu, and Glu; and
   (e) combinations thereof.

3. The method of claim 2, wherein two or more of features (a)-(e) are met.

4. The method of claim 1, wherein Asx is Asn, wherein Xaa$^1$ is any naturally occurring amino acid, wherein Xaa$^2$ is Leu, and wherein Xaa$^3$ is His, Ser, Cys, Gly, or Ala.

5. The method of claim 1, wherein Asx is Asn, wherein Xaa$^1$ is Arg or Gly, wherein Xaa$^2$ is Leu, and wherein Xaa$^3$ is His, Ala, or Gly.

6. The method of claim 1, wherein the first and second peptides are termini of the same peptide (i.e. P$^1$ and P$^2$ combine to form a single core peptide sequence); and wherein the method further comprises cyclizing said peptide.

7. The method of claim 1, wherein the peptide ligase having the activity of OaAEP1 Cys247Ala (SEQ ID NO:1) comprises or consists of an amino acid sequence that shares at least 90% sequence identity with, the amino acid sequence as set forth in SEQ ID NO: 1, provided that said peptide ligase comprises the amino acid sequence set forth in SEQ ID NO: 2 at the positions corresponding to residues 247-264 of SEQ ID NO:1 and the amino acid at position 247 is alanine.

8. The method of claim 1, wherein the peptide ligase having the activity of OaAEP1 Cys247Ala (SEQ ID NO:1) comprises or consists of
   the amino acid sequence set forth in SEQ ID NO:1.

9. The method of claim 1, wherein the first peptide and/or the second peptide further comprises one or more labelling moieties.

10. The method of claim 9, wherein the one or more labelling moieties is an affinity tag, therapeutic agent, detectable label, scaffold molecule, or combinations thereof.

11. The method of claim 1, wherein the first peptide and/or the second peptide is coupled to a solid support material.

12. The method of claim 1, wherein the first peptide and/or the second peptide is a cellular surface protein; and wherein the method further comprises modifying or tagging of the cellular surface protein.

* * * * *

UNITED STATES PATENT AND TRADEMARK OFFICE
CERTIFICATE OF CORRECTION

PATENT NO. : 11,795,488 B2
APPLICATION NO. : 16/336023
DATED : October 24, 2023
INVENTOR(S) : Bin Wu et al.

Page 1 of 1

It is certified that error appears in the above-identified patent and that said Letters Patent is hereby corrected as shown below:

In the Claims

Column 65, Claim 1, Line 61:
"Formula (I); and" should read: --Formula (II); and--.

Column 67, Claim 2, Lines 3 and 4:
Delete "(a) Asx is Asn or Asp;
(b) $Xaa^1$ is any naturally occurring amino acids;".

Column 67, Claim 2, Line 5:
"(c) $Xaa^2$ is Leu or Ile;" should read: --(a) $Xaa^2$ is Leu or Ile;--.

Column 67, Claim 2, Line 6:
"(d) $Xaa^3$ is selected" should read: --(b) $Xaa^3$ is selected--.

Column 67, Claim 2, Line 9:
"(e) combinations thereof." should read: --(c) combinations thereof.--.

Column 67, Claim 3, Line 11:
"(a)-(e) are met." should read: --(a)-(c) are met.--.

Column 67, Claim 4, Lines 12-13:
"The method of claim 1, wherein Asx is Asn, wherein $Xaa^1$ is any naturally occurring amino acid, wherein $Xaa^2$ is" should read: --The method of claim 1, wherein $Xaa^2$ is--.

Signed and Sealed this
Fourteenth Day of January, 2025

Derrick Brent
*Acting Director of the United States Patent and Trademark Office*